United States Patent
Loewke et al.

(10) Patent No.: US 9,482,659 B2
(45) Date of Patent: Nov. 1, 2016

(54) APPARATUS, METHOD, AND SYSTEM FOR THE AUTOMATED IMAGING AND EVALUATION OF EMBRYOS, OOCYTES AND STEM CELLS

(75) Inventors: Kevin Loewke, Menlo Park, CA (US); Lisa Young, Menlo Park, CA (US); Edward Menard, Menlo Park, CA (US); Shehua Shen, Menlo Park, CA (US); Lissa Goldenstein, Menlo Park, CA (US); Farshid Moussavi, Menlo Park, CA (US); Eugene Tucker, Menlo Park, CA (US)

(73) Assignee: PROGYNY, INC., Menlo Park, CA (US)

( * ) Notice: Subject to any disclaimer, the term of this patent is extended or adjusted under 35 U.S.C. 154(b) by 239 days.

(21) Appl. No.: 13/823,704
(22) PCT Filed: Sep. 27, 2011
(86) PCT No.: PCT/US2011/053537
§ 371 (c)(1),
(2), (4) Date: Nov. 25, 2013
(87) PCT Pub. No.: WO2012/047678
PCT Pub. Date: Apr. 12, 2012

(65) Prior Publication Data
US 2014/0106389 A1   Apr. 17, 2014

Related U.S. Application Data

(60) Provisional application No. 61/386,765, filed on Sep. 27, 2010.

(51) Int. Cl.
*G01N 33/50* (2006.01)
*G02B 21/00* (2006.01)
(Continued)

(52) U.S. Cl.
CPC .......... *G01N 33/5005* (2013.01); *C12M 21/06* (2013.01); *C12M 41/14* (2013.01);
(Continued)

(58) Field of Classification Search
CPC ................. B01L 2200/026; B01L 2200/0647; B01L 2200/143; B01L 2300/024; B01L 2300/0893; B01L 3/5085; G01N 33/5005; G02B 21/0088; G02B 21/088; G02B 21/125; G02B 21/18; G02B 21/365; A61K 31/404
See application file for complete search history.

(56) References Cited

U.S. PATENT DOCUMENTS

| | | |
|---|---|---|
| 4,585,315 A | 4/1986 | Sincerebox et al. |
| 5,541,081 A | 7/1996 | Hardy et al. |

(Continued)

FOREIGN PATENT DOCUMENTS

| | | |
|---|---|---|
| CN | 101331500 A | 12/2008 |
| CN | 101495619 A | 7/2009 |

(Continued)

OTHER PUBLICATIONS

U.S. Appl. No. 61/236,085, filed Aug. 22, 2009, Wong et al.

(Continued)

*Primary Examiner* — Nathan Bowers
*Assistant Examiner* — Lydia Edwards
(74) *Attorney, Agent, or Firm* — Kilpatrick Townsend & Stockton LLP

(57) ABSTRACT

Apparatuses, methods, and systems for the automated imaging and evaluation of human embryos, oocytes, or pluripotent cells are described. An apparatus and method for automated dish detection and well occupancy determination are described. In addition, a multi-well culture dish and an illumination assembly for bimodal imaging are described. These inventions find use at least in identifying or in facilitating identification of embryos and oocytes in vitro that are most useful in treating infertility in humans.

9 Claims, 42 Drawing Sheets

(51) Int. Cl.
G02B 21/08 (2006.01)
G02B 21/12 (2006.01)
G02B 21/18 (2006.01)
G02B 21/36 (2006.01)
C12M 3/00 (2006.01)
C12M 1/00 (2006.01)
C12M 1/34 (2006.01)
C12M 1/36 (2006.01)
B01L 3/00 (2006.01)

(52) U.S. Cl.
CPC ............ *C12M 41/36* (2013.01); *C12M 41/48* (2013.01); *G02B 21/0088* (2013.01); *G02B 21/088* (2013.01); *G02B 21/125* (2013.01); *G02B 21/18* (2013.01); *G02B 21/365* (2013.01); *B01L 3/5085* (2013.01); *B01L 2200/026* (2013.01); *B01L 2200/0647* (2013.01); *B01L 2200/143* (2013.01); *B01L 2300/024* (2013.01); *B01L 2300/0893* (2013.01)

(56) References Cited

U.S. PATENT DOCUMENTS

| 5,837,543 | A | 11/1998 | Conway-Myers et al. |
| 5,882,928 | A | 3/1999 | Moses |
| 5,961,444 | A | 10/1999 | Thompson |
| 6,130,086 | A | 10/2000 | Nakazawa et al. |
| 6,166,761 | A | 12/2000 | Arav |
| 6,281,013 | B1 | 8/2001 | Grondahl |
| 6,610,543 | B2 | 8/2003 | Choay et al. |
| 7,268,939 | B1 | 9/2007 | McDowell |
| 7,879,539 | B2 | 2/2011 | Pribenszky et al. |
| 7,963,906 | B2 | 6/2011 | Wong et al. |
| 8,323,177 | B2 | 12/2012 | Wong et al. |
| 8,337,387 | B2 | 12/2012 | Wong et al. |
| 8,721,521 | B2 | 5/2014 | Wong et al. |
| 8,951,184 | B2 | 2/2015 | Wong et al. |
| 8,989,475 | B2 | 3/2015 | Wong et al. |
| 2003/0103662 | A1 | 6/2003 | Finkbeiner |
| 2003/0138942 | A1 | 7/2003 | Cecchi et al. |
| 2005/0051723 | A1 | 3/2005 | Neagle et al. |
| 2006/0099570 | A1 | 5/2006 | Damgaard et al. |
| 2007/0087321 | A1 | 4/2007 | Pribenszky et al. |
| 2008/0013073 | A1* | 1/2008 | Kobayashi ............ G03F 9/7003 356/73 |
| 2008/0032325 | A1 | 2/2008 | DiMarzio et al. |
| 2008/0081982 | A1* | 4/2008 | Simon ................ G06F 19/3437 600/407 |
| 2008/0247628 | A1 | 10/2008 | Ramsing et al. |
| 2009/0056649 | A1 | 3/2009 | Mackenzie |
| 2009/0141960 | A1 | 6/2009 | Yamamoto |
| 2009/0163764 | A1 | 6/2009 | Sher et al. |
| 2010/0041090 | A1 | 2/2010 | Ramsing et al. |
| 2011/0090147 | A1* | 4/2011 | Gervais ................. G06F 3/017 345/157 |
| 2011/0092762 | A1* | 4/2011 | Wong ................. C12N 5/0604 600/34 |
| 2011/0105834 | A1 | 5/2011 | Wong et al. |
| 2011/0111447 | A1 | 5/2011 | Ramsing et al. |
| 2011/0165609 | A1 | 7/2011 | Ramsing et al. |
| 2011/0183367 | A1 | 7/2011 | Ottosen et al. |
| 2011/0189648 | A1 | 8/2011 | Pribenszky et al. |
| 2012/0040849 | A1 | 2/2012 | Simon Valles et al. |
| 2012/0094326 | A1 | 4/2012 | Wong et al. |
| 2012/0095287 | A1 | 4/2012 | Wong et al. |
| 2012/0123193 | A1 | 5/2012 | Posillico et al. |
| 2012/0140056 | A1 | 6/2012 | Pribenszky et al. |
| 2013/0023041 | A1 | 1/2013 | Greenberger et al. |
| 2013/0165745 | A1 | 6/2013 | Wong et al. |
| 2013/0337487 | A1 | 12/2013 | Loewke et al. |
| 2014/0017717 | A1 | 1/2014 | Loewke et al. |

FOREIGN PATENT DOCUMENTS

| EP | 882225 A1 | 12/1998 |
| EP | 941305 A1 | 9/1999 |
| EP | 1455643 A1 | 9/2004 |
| EP | 1542154 A2 | 6/2005 |
| EP | 1579209 A2 | 9/2005 |
| EP | 1667517 A1 | 6/2006 |
| EP | 1949297 A1 | 7/2008 |
| EP | 2035548 A2 | 3/2009 |
| EP | 2173853 A2 | 4/2010 |
| EP | 2282210 A1 | 2/2011 |
| EP | 2315823 A2 | 5/2011 |
| EP | 2333107 A1 | 6/2011 |
| EP | 2348318 A1 | 7/2011 |
| EP | 2452222 A2 | 5/2012 |
| EP | 2453738 A1 | 5/2012 |
| JP | 2009-512037 A | 3/2009 |
| JP | 2009-539387 A | 11/2009 |
| WO | 97/19345 A1 | 5/1997 |
| WO | 98/21309 A1 | 5/1998 |
| WO | 03/055385 A1 | 7/2003 |
| WO | 03/077552 A1 | 9/2003 |
| WO | 2004/005665 A2 | 1/2004 |
| WO | 2004/056265 A2 | 7/2004 |
| WO | 2005/022996 A1 | 3/2005 |
| WO | 2007/042044 A1 | 4/2007 |
| WO | 2007/144001 A2 | 12/2007 |
| WO | 2008/149055 A1 | 12/2008 |
| WO | 2009/003487 A2 | 1/2009 |
| WO | 2009/125219 A2 | 10/2009 |
| WO | 2009/146335 A1 | 12/2009 |
| WO | 2010/003423 A2 | 1/2010 |
| WO | 2010/010201 A1 | 1/2010 |
| WO | 2010/010213 A1 | 1/2010 |
| WO | 2011/004208 A2 | 1/2011 |
| WO | 2011/008932 A1 | 1/2011 |
| WO | 2011/071551 A1 | 6/2011 |
| WO | 2011/089240 A1 | 7/2011 |
| WO | 2012/042228 A2 | 4/2012 |
| WO | 2012/163363 A1 | 12/2012 |

OTHER PUBLICATIONS

U.S. Appl. No. 61/332,651, filed May 7, 2010, Wong et al.
"Human embryo which gave a vital pregnancy. Embryo Cleavage Rating (ECR)". Video uploaded to youtube.com by HlinkaDaniel on Apr. 14, 2010 (http://www.youtube.com/watch?v=6lnr4HWiz9M), 2 pages.
"Guide to Publication Policies of the Nature Journals—Editorial Policies—Nature Journals' Policies on Publication Ethics," 20 pages (Last updated Feb. 13, 2012).
"Guide to the Authors," Nature Biotechnology, 9 pages (Revised Feb. 29, 2012).
3rd Party Submission for European Application No. 10748194.4 (dated Oct. 18, 2011).
Abeydeera, L. R., "In Vitro Production of Embryos in Swine," Theriogenology, 57:257-273 (2002).
Aboulghar, M. M. et al., "Pregnancy rate is not improved by delaying embryo transfer from days 2 to 3," European Journal of Obstetrics & Gynecology and Reproductive Biology, 107:176-179 (2003).
Adachi et al., "Analysis of Physiological Process in Early Stage of Human Embryos after ICSI using Time-lapse Cinematography," J. Mamm. Ova. Res. 22:64-70 (2005).
Alikani, M. et al., "Cleavage anomalies in early human embryos and survival after prolonged culture in-vitro," Hum. Reprod., 15(12):2634-2643 (2000).
Alikani, M. et al., "Cytoplasmic fragmentation in activated eggs occurs in the cytokinetic phase of the cell cycle, in lieu of normal cytokinesis, and in response to cytoskeletal disorder," Mol. Hum. Reprod., 11(5):335-344 (2005).
Alikani, M. et al., "Human embryo fragmentation in vitro and its implications for pregnancy and implantation," Fertil. Steril., 71(5):836-842 (1999).

(56) References Cited

OTHER PUBLICATIONS

Alpha Scientists, "The Istanbul concensus workshop on embryo assessment: proceedings of an expert meeting," Human Reproduction, 26(6):1270-1283 (2011).

Altman amd Royston, "What do we man by validating a prognostic model?" Stat. Med. 19:453-473 (2000).

Alvarez, C. et al., "Zygote score and status 1 or 2 days after cleavage and assisted reproduction outcome," Int. J. Gynecol. Obstet., 101:16-20 (2008).

Ambartsumyan, G. et al., "Aneuploidy and early human embryo development," Human Molecular Genetics, 17(1):R10-R15 (2008).

American Journal of Obstetrics & Gynecology's website regarding Mio (2008) (2012), 2 pages.

Andersen, A. N. et al., "Assisted reproductive technology in Europe, 2004: results generated from European registers by ESHRE," Hum. Reprod., 23(4):756-771 (2008).

Anoraganingrum, D., "Cell segmentation with median filter and mathematical morphology operation," Proceedings of International Conference on Image Analysis and Processing, pp. 1043-1046 (1999).

Antczak, M. et al., "Oocyte influences on early development: the regulatory proteins leptin and STAT3 are polarized in mouse and human oocytes and differentially distributed within the cells of the preimplantation stage embryo," Mol. Hum. Reprod., 3(12):1067-1086 (1997).

Antczak, M. et al., "Temporal and spatial aspects of fragmentation in early human embryos: possible effects on developmental competence and association with the differential elimination of regulatory proteins from polarized domains," Human Reprod., 14:429-447 (1999).

Aprysko, V. P. et al., "Noninvasive selection of euploid embryos with high implantation potential based on synchronism of blastomere cleavage," Abstracts of the $26^{th}$ Annual Meeting of ESHRE, P-206:i196-i197 (2010).

Arav, A., "Prediction of embryonic developmental competence by time-lapse observation and shortest-half analysis," Reproductive Biomedicine Online, 17(5):669-675, Article 3412 (Sep. 30, 2008).

ASRM Website, http://www.asrm.org/; Copyright 1996-2012 ASRM, American Society for Reproductive Medicine.

Atasoy, S. et al., "A Global Approach for Automatic Fibroscopic Video Mosaicing in Minimally Invasive Diagnosis," Proceedings of MICCAI, pp. 850-857 (2008) (contains duplicate pages for figure clarity).

Baart, E. B. et al., "Fluorescence in situ hybridization analysis of two blastomeres from day 3 frozen-thawed embryos followed by analysis of the remaining embryo on day 5," Hum. Reprod., 19(3):685-693 (2004).

Baart, E. B. et al., "Preimplantation genetic screening reveals a high incidence of aneuploidy and mosaicism in embryos from young women undergoing IVF," Hum Reprod., 21(1):223-233 (2006).

Bahceci, M. et al., "Efficiency of changing the embryo transfer time from day 3 to day 2 among women with poor ovarian response: A prospective randomized trial," Fertility and Sterility, 86(1):81-85 (2006).

Balaban, B. et al., "Effect of oocyte morphology on embryo development and implantation," Reproductive BioMedicine Online, 12(5):608-615 (2006).

Baltaci, V. et al., "Relationship between embryo quality and aneuploidies," Reprod. BioMed. Online, 12(1):77-82 (2006).

Barbash-Hazan, S. et al., "Preimplantation aneuploid embryos undergo self-correction in correlation with their developmental potential," Fertil. Steril., 92(3):890-896 (2009).

Basile, N. et al., "Time lapse technology: evaluation of embryo quality and new markers for embryo selection," Expert Rev. Obstet. Gynecol., 7(2):175-190 (2012).

Basille et al., "Preimplantation genetic diagnosis: State of the art," Eur. J. Obstet. Gynecol. Reprod. Biol. 145:9-13 (2009).

Bavister, B. D. et al., "Duration and temperature of culture medium equilibration affect frequency of blastocyst development," Reprod. BioMed. Online, 10(1):124-129 (2004).

Bavister, B., "The role of animal studies in supporting human assisted reproductive technology," Reprod. Fertil. Dev., 16:719-728 (2004).

Baxter Bendus, A. E. et al., "Interobserver and intrabserver variation in day 3 embryo grading," Fertility and Sterility, 86(6):1608-1615 (2006).

Becker, V. et al., "High-resolution miniprobe-based confocal microscopy in combination with video mosaicing," Gastrointestinal Endoscopy, 66(5):1001-1007 (2007).

Beddington, R. S. P. et al., "An assessment of the developmental potential of embryonic stem cells in the midgestation mouse embryo," Development, 105:733-737 (1989).

Behr, B. et al., "Metebolomic profile of human oocyte is predictive to embryo development and viability," Abstracts of the $24^{th}$ Meeting of the ESHRE, O-205:i83 (2008).

Ben-Yosef, D. et al., "Prospective Randomized Comparison of Two Embryo Culture Systems: P1 Medium by Irvine Scientific and the Cook IVF Medium," J. Assist. Reprod. Genet., 21(8):291-295 (2004).

Bischoff, M. et al., "Formation of the embryonic-abembryonic axis of the mouse blastocyst: relationships between orientation of early cleavage divisions and pattern of symmetric/asymmetric divisions," Development, 135:953-962 (2008).

Boiso et al., (2002) "Fundamentals of Human Embryonic Growth in vitro and the selection of high-quality embryos for transfer" Reproductive BioMedicine Online, 5(3):328-350.

Booth, P. J. et al., "Prediction of Porcine Blastocyst Formation Using Morphological, Kinetic, and Amino Acid Depletion and Appearance Criteria Determined During the Early Cleavage of In Vitro-Produced Embryos," Biology of Reproduction, 77:765-779 (2007).

Bos-Mikich et al., (2001) "Early cleavage of human embryos: an effective method for predicting successful IVF/ICSI outcome," Human Reprod. 16(12):2658-2661.

Brezinova, et al. (2009) "Evaluation of day one embryo quality and IVF outcome—a comparison of two scoring systems," Reproductive Biology and Endocrinology, 7:9-14.

Brison, D. R. et al., "Predicting human embryo viability: the road to non-invasive analysis of the secretome using metabolic footprinting," Reprod. BioMed. Online, 15(3):296-302 (2007).

Bromer, J. G. et al., "Assessment of embryo viability in assisted reproductive technology: shortcomings of current approaches and the emerging role of metabolomics," Curr. Opin. Obstet. Gynecol., 20:234-241 (2008).

Chavez et al., "Dynamic blastomere behaviour reflects human embryo ploidy by the four-cell stage," Nature Commun. 3, Article No. 1251 (2012) doi:10.1038/ncomms2249.

Chenouard, N. et al., "Improving 3D tracking in microscopy by joint estimation of kinetic and image models," MICCAI Workshop on MIAAB (2008).

Clinic Summary Report, All SART Member Clinics, The Society of Assisted Reproductive Technology ("SART") 2010 statistics as published on the SART website (2012), 1 page.

Coy, P. et al., "In vitro production of pig embryos: a point of view," Reprod. Fertil. Dev., 14:275-286 (2002).

Cruz, M. et al., "Embryo quality, blastocyst and ongoing pregnancy rates in oocyte donation patients whose embryos were monitored by time-lapse imaging," J. Asssit. Reprod. Genet., 28:569-573 (2011).

Cruz, M. et al., "Timing of cell divisions in human cleavage-stage embryos correlates with blastocyst formation and quality," Reprod. BioMed. Online, Accepted Manuscript:26 pages. (2012).

Cummins, et al. (1986) "A formula for scoring human embryo growth rates in in vitro fertilization: Its value in predicting pregnancy and in comparison with visual estimates of embryo quality," Journal of In Vitro Fertilization and Embryo Transfer, 3(5):284-295.

De Los Santos, J. M. et al., "Development of tripronucleated ICSI-derived embryos using real time assessment," Abstracts of the $26^{th}$ Annual Meeting of ESHRE, P-196:i192 (2010).

De Los Santos, M. J. et al., "Implantation Rates after Two, Three, or Five Days of Embryo Culture," Placenta, 24:S13-S19 (2003).

Declaration of Prof. Markus Montag Under 37 C.F.R. § 1.132 (dated Oct. 13, 2011).

(56) References Cited

OTHER PUBLICATIONS

Desai, N. et al., "Granulocyte-macrophage colony stimulating factor (GM-CSF) and co-culture can affect post-thaw development and apoptosis in cryopreserved embryos," J. Assist. Reprod. Genet., 24:215-222 (2007).
Dominko, T. et al., "Dynamic Imaging of the Metaphase II Spindle and Maternal Chromosomes in Bovine Oocytes: Implications for Enucleation Efficiency Verification, Avoidance of Parthenogenesis, and Successful Embryogenesis," Biology of Reproduction, 62:150-154 (2000).
Dumoulin, J. C. et al., "Effect of in vitro culture of human embryos on birthweight of newborns," Hum. Reprod., 25(3):605-612 (2010).
Dykstra, B. et al., "High-resolution video monitoring of hematopoietic stem cells cultured in single-cell arrays identifies new features of self-renewal," PNAS, 103(21):8185-8190 (2006).
Ebner, T. et al., "Embryo fragmentation in vitro and its impact on treatment and pregnancy outcome," Fertil. Steril., 76(2):281-285 (2001).
Edwards, B. et al., "Initial differentiation of blastomeres in 4-cell human embryos and its significance for early embryogenesis and implantation," Reprod. BioMed. Online, 11(2):206-218 (2005).
Edwards, R. G. et al., "Early Stages of Fertilization in vitro of Human Oocytes Matured in vitro," Nature, 221:632-635 (1969).
El-Toukhy et al., (2009) "A multi-centre randomised controlled study of pre-IVF outpatient hysteroscopy in women with recurrent IVF implantation failure: Trial of Outpatient Hysteroscopy—[TROPHY] in IVF," Reprod. Health, 6:20 (7 pages). doi: 10.1186/1742-4755-6-20. Epub Dec. 3, 2009.
Email from the managing editor of Fertility and Sterility (Aug. 1, 2012), 1 page.
European Search Report, 7 pages, EP appl. No. 13152098.3 (Jun. 19, 2013).
Fancsovits, et al., (2006) "Examination of Early Cleavage and its Importance in IVF Treatment," Journal Reproduktionsmed Endokrinol, 3(6):367-372.
Fancsovits, P. et al., "Early pronuclear breakdown is a good indicator of embryo quality and viability," Fertil. Steril., 84(4):881-887 (2005).
Fauque, P. et al., "Pregnancy outcome and live birth after IVF and ICSI according to embryo quality," J. Assist. Reprod. Genet., 24:159-165 (2007).
Fenwick, et al., (2002) "Time from insemination to first cleavage predicts developmental competence of human preimplantation embryos in vitro," Human Reproduction, 17(2):407-412.
Fisch, et al. (2001) "The graduateed embryo score (GES) predicts blastocyst formation and pregnancy rate from cleavage stage embryos" Hum. Reprod. 16(9):1970-1975.
Fotos et al., "Automated time-lapse microscopy and high-resolution tracking of cell migration," Cytotechnology 51:7-19 (2006).
Fragouli, E. et al., "Comparative genomic hybridization analysis of human oocytes and polar bodies," Hum. Reprod., 21:2319-2328 (2006).
Fragouli, E. et al., "Comprehensive chromosome screening of polar bodies and blastocysts from couples experiencing repeated implantation failure," Fertil. Steril., 94(3):875-887 (2010).
Fragouli, E. et al., "Increased susceptibility to maternal aneuploidy demonstrated by comparative genomic hybridization analysis of human MII oocytes and first polar bodies," Cytogenetic and Genome Res., 114:30-38 (2006).
Frumkin, T. et al., "Elucidating the origin of chromosomal aberrations in IVF embryos by preimplantation genetic analysis," Mol. Cell. Endocrinol., 282:112-119 (2008).
Gardner, D. K. et al., "Assessment of Embryo Viability: The Ability to Select a Single Embryo for Transfer—a Review," Placenta, 24:S5-S12 (2003).
Gardner, D. K. et al., "Textbook of Assisted Reproduction Techniques," Preface, Introduction, Chapter 2, Chapter 10, and Chapter 16 (2001).
Gardner, R. L., "Specification of embryonic axes begins before cleavage in normal mouse development," Development, 128:839-847 (2001).
Gardner, R. L., "The early blastocyst in bilaterally symmetrical and its axis of symmetry is aligned with the animal-vegetal axis of the zygote in the mouse," Development, 124:289-301 (1997).
Geber, S. et al., "Proliferation of blastomeres from biopsied cleavage stage human embryos in vitro: an alternative to blastocyst biopsy for preimplantation diagnosis," Hum. Reprod., 10:1492-1496 (1995).
Giorgetti, C. et al., "Early cleavage: an additional predictor of high implantation rate following elective single embryo transfer," Reprod. BioMed. Online, 14(1):85-91 (2007).
Gonzales, D. S. et al., "Prediction of the developmental potential of hamster embryos in vitro by precise timing of the third cell cycle," J. Reprod. Fertil., 105(1):1-8 (1995).
Gonzales, D. S. et al., "Trophectoderm projections: a potential means for locomotion, attachment and implantation of bovine, equine and human blastocysts," Hum. Reprod., 11(12):2739-2745 (1996).
Gray, D. et al., "First Cleavage of the Mouse Embryo Responds to Change in Egg Shape at Fertilization," Current Biology, 14:397-405 (2004).
Grisart, B. et al., "Cinematographic analysis of bovine embryo development in serum-free oviduct-conditioned medium," J. Reprod. Fertil., 101(2):257-264 (1994).
Guerif, et al. (2002) "Parameters guiding selection of best embryos for transfer after cryopreservation: a reappraisal," Human Reprod. 17(5):1321-1326.
Guerif, et al. (2007) "Limited value of morphological assesment at days 1 and 2 to predict blastocyst development potential: A prospective study based on 402 embryos," Human Reprod. 22(7):1973-1981.
Guerif, F. et al., "Single Day 2 embryo versus blastocyst-stage transfer: a prospective study integrating fresh and frozen embryo transfers," Human Reproduction, 24(5):1051-1058 (2009).
Hahnel, D. et al., "An Extension of the ICP Algorithm for Modeling Nonrigid Objects with Mobile Robots," Proc. of IJCAI-03, pp. 915-920 (2003).
Handyside, A. H., "Pregnancies from biopsied human preimplantation embryos sexed by Y-specific DNA amplification," Nature, 344:768-770 (1990).
Handyside, A. H., "Time of commitment of inside cells isolated from preimplantation mouse embryos," J. Embryol. Exp. Morphol., 45:37-53 (1978).
Hardarson, T. et al., "Human embryos with unevenly sized blastomeres have lower pregnancy and implantation rates: indications for aneuploidy and multinucleation," Human Reproduction, 16(2):313-318 (2001).
Hardarson, T. et al., "Internalization of cellular fragments in a human embryo: time-lapse recordings," Reprod. BioMed. Online, 5(1):36-38 (2002).
Hardy, K. et al., "From cell death to embryo arrest: Mathematical models of human preimplantation embryo development," PNAS, 98(4):1655-1660 (2001).
Hardy, K. et al., "Human preimplantation development in vitro is not adversely affected by biopsy at the 8-cell stage," Hum. Reprod., 5(6):708-714 (1990).
Hardy, K. et al., "Maintenance of the Inner Cell Mass in Human Blastocysts from Fragmented Embryos," Biol. Reprod., 68:1165-1169 (2003).
Hardy, K. et al., "The human blastocyst: cell number, death and allocation during late preimplantation development in vitro," Development, 107:597-604 (1989).
Harrell Jr. et al., "Tutorial in Biostatistics. Multivariable Prognostic Models: Issues in Developing Models, Evaluating Assumptions and Adequacy, and Measuring and Reducing Errors," Sta. Med. 15:361-387 (1996).
Hashimoto, S. et al., "Selection of high-potential embryos by culture in poly(dimethylsiloxane) microwells and time-lapse imaging," Fert. and Steril., 97(2):332-337 (2012).

(56) References Cited

OTHER PUBLICATIONS

Heid, P. J. et al., "3D-DIASemb: A Computer-Assisted System for Reconstructing and Motion Analyzing in 4D Every Cell and Nucleus in a Developing Embryo," Developmental Biology, 245:329-347 (2002).
Heindryckx, B. et al., "Embryo development after successful somatic cell nuclear transfer to in vitro matured human germinal vesicle oocytes," Hum. Reprod., 22(7):1982-1990 (2007).
Hesters et al., "Impact of early cleaved zygote morphology on embryo development and in vitro fertilization-embryo transfer outcome: a prospective study," Fertil. Steril. 89(6):1677-1684 (2008).
Hiiragi, T. et al., "First cleavage plane of the mouse egg is not predetermined but defined by the topology of the two apposing pronuclei," Nature, 430:360-364 (2004).
Hinkins et al., "Expression of Polycomb-group genes in human ovarian follicles, oocytes and preimplantation embryos," Reproduction 130:883-888 (2005).
Hiraoka, L. et al., "Spindle-Pole Organization during Early Mouse Development," Devel. Biol., 133:24-36 (1989).
Hlinka et al., "Time-Lapse Cleavage Rating Predicts Human Embryo Viability," Physiol. Res. 61:513-525 (2012).
Hlinka, D. et al., "Permanent embryo monitoring and exact timing of early cleavages allow reliable prediction of human embryo viability," Abstracts of the 26$^{th}$ Annual Meeting of ESHRE, P-176:i184-i185 (2010).
Hnida, C. et al., "Computer-controlled, multilevel, morphometric analysis of blastomere size as biomarker of fragmentation and multinuclearity in human embryos," Human Reproduction, 19(2):288-293 (2004).
Hnida, C. et al., "Total Cytoplasmic Volume as Biomarker of Fragmentation in Human Embryos," Journal of Assisted Reproduction and Genetics, 21(9):335-340 (2004).
Hnida, C. et al., "Traditional detection versus computer-controlled multilevel analysis of nuclear structures from donated human embryos," Human Reproduction, 20(3):665-671 (2005).
Hogan, B. et al., "In vitro development of inner cell masses isolated immunosurgically from mouse blastocysts. I. Inner cell masses from 3.5- to 4.0-day p. c. blastocysts incubated for 24 h before immunosurgery," J. Embryol. Exp. Morphol., 45:107-121 (1978).
Holm, et al. (1998) " Developmental kinetics of the first cell cyles of bovine in vitro produced embryos in relation to their in vitro viability and sex," Theriogenology 50:1285-1299.
Holm, P. et al., "In vivo versus in vitro produced bovine ova: similarities and differences relevant for practical application," Reprod. Nutr. Dev., 38:579-594 (1998).
Holm, P. et al., "Kinetics of early in vitro development of bovine in vivo- and in vitro-derived zygotes produced and/or cultured in chemically defined or serum-containing media," Reproduction, 123:553-565 (2002).
Honda, H. et al., "Computer simulation of emerging asymmetry in the mouse blastocyst," Development, 135:1407-1414 (2008).
International Preliminary Report on Patentability for International Application No. PCT/US2010/046343, 7 pages (issued Feb. 28, 2012).
International Search Report from PCT Application No. PCT/US2011/053537, dated Apr. 6, 2012 (4 pages).
International Search Report, PCT appl. No. PCT/US2012/026328, 4 pages (Aug. 3, 2012).
International Search Report, PCT appl. No. PCT/US2013/043639, 3 pages (Nov. 22, 2013).
Jang, M-S. et al., "Shape Recognition of the Embryo Cell Using Deformable Template for Micromanipulation," R. Orchard et al. (Eds.): IEA/AIE 2004, LNAI 3029, pp. 463-472 (2004).
Janssens, Ronny, "Standardisation of embryo evaluation", http://www.fertaid.com/Presentations/embryoevalstand.pdf, 2007 (39 pages).
Johnson, D. S. et al., "Preclinical validation of a microarray method for full molecular karyotyping of blastomeres in a 24-h protocol," Hum. Reprod., 25(4):1066-1075 (2010).
Johnson, M. H. et al., "Cell Interactions Influence the Fate of Mouse Blastomeres Undergoing the Transition from 16- to the 32-Cell Stage," Devel. Biol., 95:211-218 (1983).
Johnson, M. H. et al., "Lineage allocation and cell polarity during mouse embryogenesis," Sem. Cell. Devel. Biol., 15:583-597 (2004).
Jones, G. M. et al., "Novel strategy with potential to identify developmentally competent IVF blastocysts," Hum. Reprod., 23(8):1748-1759 (2008).
Jun, et al (2008) "Defining human embryo phenotypes by cohort-specific prognostic factors," PlosOne 3(7):284-290.
Justice et al., "Assessing the Generalizability of Prognostic Information," Ann. INtern. Med. 130:515-524 (1999).
Katz-Jaffe, M. G. et al., "A proteomic analysis of mammalian preimplantation embryonic development," Reproduction, 130:899-905 (2005).
Katz-Jaffe, M. G. et al., "Analysis of protein expression (secretome) by human and mouse preimplantation embryos," Fertility and Sterility, 86(3):678-685 (2006).
Katz-Jaffe, M. G. et al., "Proteomic analysis of individual human embryos to identify novel biomarkers of development and viability," Fertility and Sterility, 85(1):101-107 (2006).
Katz-Jaffe, M. G. et al., "Relationship between cleavage stage morphology and comprehensive chromosome constitution," Abstracts of the 26$^{th}$ Annual Meeting of ESHRE, P-146:i172 (2010).
Katz-Jaffe, M. G. et al., "Symposium: Innovative techniques in human embryo viability assessment—Can proteomics help to shape the future of human assisted conception?," Reprod. BioMed. Online, 17(4):497-501 (2008).
Katz-Jaffe, M. G. et al., "The role of proteomics in defining the human embryonic secretome," Molecular Human Reproduction, 15(5):271-277 (2009).
Keltz, M. D. et al., "Predictors of embryo fragmentation and outcome after fragment removal in in vitro fertilization," Fertility and Sterility, 86(2):321-324 (2006).
Kidder, G. M. et al., "Timing of Transcription and Protein Synthesis Underlying Morphogenesis in Preimplantation Mouse Embryos," Devel. Biol., 112:265-275 (1985).
Kiessling, A. A., "Timing is everything in the human embryo," Nature Biotechnology, 28:1025-1026 (2010).
Kirkegaard, K. et al., "Human embryonic development after blastomere removal: a time-lapse analysis," Hum. Reprod., 27:97-105 (2012).
Kirkegaard, K. et al., "Time-lapse monitoring as a tool for clinical embryo assessment," Human Reproduction, 27(5):1277-1285 (2012).
Kuo, H-C. et al., "Chromosomal mosaicism in cleavage-stage human embryos and the accuracy of single-cell genetic analysis," J. Assist. Reprod. Genet., 15(5):276-280 (1998).
Kurimoto, K. et al., "An improved single-cell cDNA amplification method for efficient high-density oligonucleotide microarray analysis," Nucleic Acids Research, 34(5):e42 (2006), 17 pages.
Kurotaki, Y. et al., "Blastocyst Axis Is Specified Independently of Early Cell Lineage But Aligns with the ZP Shape," Science 316:719-723 (2007).
Langenberg, T. et al., "Imaging Brain Development and Organogensis in Zebrafish Using Immobilized Embryonic Explants," Developmental Dynamics, 228:464-474 (2003).
Lathi, R. B. et al., "Pregnancy after trophectoderm biopsy of frozen-thawed blastocyst," Fertility and Sterility, 91(5):1938-1940 (2009).
Lavoir, M. et al., "Poor development of human nuclear transfer embryos using failed fertilize oocytes," Reprod. BioMed. Online, 11(6):740-744 (2005).
Lawson, K., "Fate mapping the mouse embryo," Int. J. Dev. Biol., 43:773-775 (1999).
Le Gac, S. et al., "Development of integrated microfluidic chips for single embryo physiology studies," Abstracts of the 26$^{th}$ Annual Meeting of ESHRE, P-159:i177 (2010).
Lechniak et al., "Timing of the first zygotic cleavage as a marker of developmental potential of mammalian embryos," Reprod. Biol. 8(1):23-42 (2008).

(56) References Cited

OTHER PUBLICATIONS

Lee, S. G. et al., "Comparision of with or without early cleavage assessment for elective single embryo transfer on day 3," Abstracts of the 26$^{th}$ Annual Meeting of ESHRE, P-167:i180-i181 (2010).

Lemmen et al., "Kinetic markers of human embryo quality using time-lapse recordings of IVF/ICSI-fertilized oocytes," Reprod. Biomed. Online 17:385-391 (2008).

Lequarre, et al., (2003) "Cell cycle duration at the time of maternal zygotic transition for in vitro produced bovine embryos: effect of oxygen tension and transcription inhibition," Biology of Reproduction, 69:1707-1713.

Lewin, et al. (1994) "Embryo growth rate in vitro as an indicator of embryo quality in IVF cycles," Journal of Assisted Reproduction and Genetics, 11(10):500-503.

Lewis, W.H. et al., "Cinematographs of living developing rabbit-eggs," Science, 69(1782):226-229 (1929).

Li, K. et al., "Cell population tracking and lineage construction with spatiotemporal context," Medical Image Analysis, 12:546-566 (2008).

Li, K. et al., "Online Tracking of Migrating and Proliferating Cells Imaged with Phase-Contrast Microscopy," Proceedings of the 2006 Conference on Computer Vision and Pattern Recognition Workshop, IEEE, 8 pages (2006).

Liebermann, J. et al., "Blastocyst development after vitrification of multipronuclear zygotes using the Flexipet denuding pipette," Reproductive BioMedicine Online, 4(2):146-150 (2002).

Liu, L. et al., "A reliable, noninvasive technique for spindle imaging and enucleation of mammalian oocytes," Nature Biotechnology, 18:223-225 (2000).

Loewke, K. E. et al., "In Vivo Micro-Image Mosaicing," IEEE Transactions on Biomedical Engineering, 58(1):159-171 (2011).

Loewke, K. E. et al., "Real-Time Image Mosaicing for Medical Applications," Proceedings of MMVR, 15:304-309 (2007).

Loewke, K. et al., "Real-time image mosaicing with a hand-held dual-axes confocal microscope," Proc. of SPIE, 6851:68510F-1-68510F-8 (2008).

Louvet-Vallee, S. et al., "Mitotic Spindles and Cleavage Planes Are Oriented Randomly in the Two-Cell Mouse Embryo," Current Biology, 15:464-469 (2005).

Lundin, et al, (2001) "Early embryo cleavage is a strong indicator of embryo quality in human IVF," Human Reproduction, 16(12):2652-2657.

Magli, M. C. et al., "Chromosomal abnormalities in embryos," Mol. Cell. Endocrinol., 183:S29-S34 (2001).

Manipalviratn et al., "Imprinting disorders and assisted reproductive technology," Fertil Steril., Feb. 2009, 91(2):305-315.

Marhuenda-Egea, F. C. et al., "Improving human embryos selection in IVF: non-invasive metabolomic and chemometric approach," Metabolomics, 7(2):247-256 (2011).

Massip, A. et al., "The behaviour of cow blastocyst in vitro: cinematographic and morphometric analysis," J. Anat., 134(2):399-405 (1982).

Massip, A. et al., "Time-lapse cinematographic analysis of hatching of normal and frozen-thawed cow blastocysts," J. Reprod. Fertil., 58:475-478 (1980).

Mastenbroek, S. et al., "In Vitro Fertilization with Preimplantation Genetic Screening," N. Engl. J. Med., 357(1):9-17 (2007).

Mauhin, "International Search Report," 7 pages, from PCT Application No. PCT/US2010/046343, European Patent Office, Rijswijk, The Netherlands (mailed Nov. 15, 2010).

Mauhin, "Written Opinion of the International Searching Authority," 6 pages, from PCT Application No. PCT/US2010/046343, European Patent Office, Rijswijk, The Netherlands (mailed Nov. 15, 2010).

McCarthy, E. K. et al., "Asymmetric spindle positioning," Current Opinion in Cell Biology, 18:79-85 (2006).

McKiernan, S. H. et al., "Timing of development is a critical parameter for predicting successful embryogenesis," Human Reproduction, 9(11):2123-2129 (1994).

Menezes, J. et al., "Video observations on human blastocyst hatching," Reprod. BioMed. Online, 7(2):217-218 (2003).

Meng et al., "Remote Monitoring and Evaluation of Early Human Embryo Development by a Robotic-Operated Culture-Imaging System," Fertil. Steril. 91(3) Supplement; p. S7 (2009).

Meseguer, M. et al., "The use of morphokinetics as a predictor of embryo implantation," Hum. Reprod., 26(10):2658-2671 (2011) [Published online Aug. 9, 2011; pp. 1-14].

Miles, H. L., "In Vitro Fertilization Improves Childhood Growth and Metabolism," J. Clin. Endocrinol. Metab., 92(9):3441-3445 (2007).

Milki, A. A. et al., "Accuracy of day 3 criteria for selecting the best embryos," Fertility and Sterility, 77(6):1191-1195 (2002).

Milki, A. A. et al., "Comparison of blastocyst transfer with day 3 embryo transfer in similar patient populations," Fertility and Sterility, 73(1):126-129 (2000).

Milki, A. A. et al., "Elective single blastocyst transfer," Fertility and Sterility, 81(6):1697-1698 (2004).

Mio and Maeda, "Time-lapse cinematography of dynamic changes occurring during in vitro development of human embryos," Am. J. Obstet. Gynecol. I99:660.el-660.e5 (2008).

Mio, "Morphological analysis of human embryonic development using time-lapse cinematography," J. Mamm. Ova. Res. 23:27-35 (2006).

Mitalipov, S. M. et al., "Monozygotic Twinning in Rhesus Monkeys by Manipulation of In Vitro-Derived Embryos," Biol. Reprod., 66:1449-1455 (2002).

Montag, et al. (2008) "Symposium: Innovative techniques in human embryo viability assesment. Oocyte assessment and embryo viability prediction: birefringence imaging," Reprod. BioMed. Online, 17(4):454-460.

Montag, M. et al., "Significance of the number of embryonic cells and the state of the zona pellucida for hatching of mouse blastocysts in vitro versus in vivo," Biol. Reprod., 62:1738-1744 (2000).

Montag, M. et al., "Which morpohological scoring system is relevant in human embryo development," Placenta, 32:S252-S256 (2011).

Mottla, G. L. et al., "Lineage tracing demonstrates that blastomeres of early cleavage-stage human pre-embryos contribute to both trophectoderm and inner cell mass," Human Reproduction, 10(2):384-391 (1995).

Mtango, N. R. et al., "Oocyte Quality and Maternal Control of Development," Int. Rev. Cell. Mol. Biol., 268:223-290 (2008).

Munne, S. et al., "Improved implantation after preimplantation genetic diagnosis of aneuploidy," Reprod. Biomed. Online, 7(1):91-97 (2003).

Munne, S. et al., "Self-correction of chromosomally abnormal embryos in culture and implications for stem cell production," Fertil. Steril., 84(5):1328-1334 (2005).

Nagy, Z. P. et al., "Metabolomic assessment of oocype viability," Reproductive BioMedicine Online,18(2):219-225 (2008).

Nagy, Z. P. et al., "Symposium: Innovative techniques in human embryo viability assessment. Non-invasive assessment of embryo viability by metabolomic profiling of culture media ('metabolomics')," Reproductive BioMedicine Online, 17(4):502-507 (2008).

Nagy, Z. P. et al., "Time-course of oocyte activation, pronucleus formation and cleavage in human oocytes fertilized by intracytoplasmic sperm injection," Human Reproduction, 9(9):1743-1748 (1994).

Nakahara, T. et al., "Evaluation of the safety of time-lapse observations for human embryos," J. Assist. Reprod. Genet., 27:93-96 (2010).

National Summary Report, The Centers for Disease Control and Prevention ("CDC") ART 2010 statistics as published on the CDC's website (2012).

Nomura, et al. (2007) "Preferable correlation to blastocyt development and pregnancy rates with a new embryo grading system specific for day 3 embryos" J. Assisted Reprod. Genet. 24:24-28.

Office Action for European Patent Application No. 10748195.4 (dated Jun. 6, 2012).

Office Action for Inter Partes Reexamination Application 95/001,785 (mailed Jun. 11, 2012).

Office Action for U.S. Appl. No. 13/302,908 (mailed Apr. 20, 2012).

(56) References Cited

OTHER PUBLICATIONS

Office Action for U.S. Appl. No. 13/302,914 (mailed Apr. 26, 2012).
Ogilvie, C.M., "Review," Obstetrician & Gynaecol., 10:88-92 (2008).
Oh, S.J. et al., "Light intensity and wavelength during embryo manipulation are important factors for maintaining viability of preimplantation embryos in vitro," Fert. Steril., 88(Suppl. 2):1150-1157 (2007).
Olsen, N. H., "Morphology and Optics of Human Embryos from Light Microscopy," Ph.D. Thesis from IT University of Copenhagen; defended Mar. 24, 2003 (2003).
Opposition to EP-B-2430454, filed at the EPO on Feb. 18, 2013, 21 pages.
Ottosen, L. D. et al., "Light exposure of the ovum and preimplantation embryo during ART procedures," J. Assist. Reprod. Genet., 24:99-103 (2007).
Ottosen, L. D. et al., "Murine pre-embryo oxygen consumption and developmental competence," J. Assist. Reprod. Genet., 24:359-365 (2007).
Pantos, K. et al., "Comparison of embryo transfer on day 2, day 3, and day 6: a prospective randomized study," Fertility and Sterility, 81(2):454-455 (2004).
Park, A., "Predicting IVF Success," The Top 10 Everything of 2010, Top 10 Medical Breakthroughs, Time Magazine, Dec. 9, 2010, as published on Time Magazine's website (2012).
Payne et al., "Relationship between pre-embryo pronuclear morphology (zygote score) and standard day 2 or 3 embryo morphology with regard to assisted reproductive technique outcomes," Fertil. Steril. 84(4):900-909 (2005).
Payne, D. et al., "Preliminary observations on polar body extrusion and pronuclear formation in human oocytes using time-lapse video cinematography," Human Reproduction, 12(3):532-541 (1997).
Pearce, "Stanford University's patent on embryo selection is not excluded under European patent law," Reprod. BioMed. Online (2013), doi: http://dx.doi.org/10.1016/j.rbmo.2013.11.001.
Pedersen, U. D. et al., "A multiphase variational level set approach for modelling human embryos," ICCV Workshop on VGLSMCV (2003).
Pedersen, U. D. et al., "Modeling Human Embryos Using a Variational Level Set Approach," Ph.D. Thesis from IT University of Copenhagen (2004).
Pennetier et al., "Spatio-Temporal Expression of the Germ Cell Marker Genes MATER, ZAR1, GDF9, BMP15, and VASA in Adult Bovine Tissues, Oocytes, and Preimplantation Embryos," Biol. Reprod. 71:1359-1366 (2004).
Petersen, et al. (2001) "Embryo seletion by the first cleavage parameter between 25 and 27 hours after ICSI," J. Assisted Reprod and Genetics 18(4):209-212.
Piotrowska, K. et al., "Blastomeres arising from the first cleavage division have distinguishable fates in normal mouse development," Development, 128:3739-3748 (2001).
Piotrowska, K. et al., "Early patterning of the mouse embryo—contributions of sperm and egg," Development, 129:5803-5813 (2002).
Piotrowska, K. et al., "Role the sperm in spatial patterning of the early mouse embryo," Nature, 409:517-521 (2001).
Piotrowska-Nitsche, K. et al., "Four-cell stage mouse blastomeres have different developmental properties," Development, 132:479-490 (2004).
Piotrowska-Nitsche, K. et al., "Spatial arrangement of individual 4-cell stage blastomeres and the order in which they are generated correlate with blastocyst pattern in the mouse embryo," Mechanisms of Development, 122:487-500 (2005).
Plusa, B. et al., "The first cleavage of the mouse zygote predicts the blastocyst axis," Nature, 434:391-395 (2005).
Prados, N. et al., "Improved human embryo quality in days 3 and 5 with a low oxigen closed culture system," Abstracts of the $26^{th}$ Annual Meeting of ESHRE, P-191:i190 (2010).

Pribensky et al., "Prediction of in-vitro developmental competence of early cleavage-stage mouse embryos with compact time-lapse equipment," Reprod. BioMed., 20:371-379 (2010).
Qian, Y-L. et al., "Accuracy of a combined score of zygote and embryo morphology for selecting the best embryos for IVF," J. Zhejiang Univ. Sci. B, 9(8):649-655 (2008).
Quinlan, G. A. et al., "Lineage Allocation During Early Embryogenesis—Mapping of the Neural Primordia and Application to the Analysis of Mouse Mutants," Methods in Molecular Biology, 158:227-250 (2001).
Racowsky, C. et al., "Day 3 and day 5 morphological predictors of embryo viability," Reprod. BioMed. Online, 6(3):323-331 (2003).
Racowsky, C., "High rates of embryonic loss, yet high incidence of multiple births in human ART: is this paradoxical?", Theriogenology, 57:87-96 (2002).
Ralston, A. et al., "Cdx2 acts downstream of cell polarization to cell-autonomously promote trophectoderm fate in the early mouse embryo," Devel. Biol., 313:614-629 (2008).
Ramsing and Callesen, (2006) "Automated image analysis quantifies blastomere activity in time-lapse images to detect onset and duration of cell division during embryo development," Abstracts of the $22^{nd}$ Annual Meeting of the ESHRE, Prague, Czech Republic, Jun. 18-21, 2006.
Ramsing, N. B. et al., "Detecting timing and duration of cell divisions by automatic image analysis may improve selection of viable embryos," Fertility and Sterility, P-153:S189 (2006).
Ramsing, N.B. et al., "Automated detection of cell division and movement in time-lapse images of developing bovine embryos can improve selection of viable embryos," Fertil. Steril., 88:S38 (2007).
Ramsing, N.B. et al., "Morphokinetic analysis of embryo development," Unisense FertiliTech, Version 027, pp. 1-14 (Jun. 15, 2011).
Ramsing, N.B. et al., "Morphokinetic analysis of embryo development," Unisense FertiliTech, Version F7.797.4, pp. 1-15 (Nov. 16, 2011).
Ramunas, J. et al., "True Monolayer Cell Culture in a Confined 3D Microenvironment Enables Lineage Informatics," Cytometry Part A, 69A:1202-1211 (2007).
Rawe, V. Y. et al., "Cytoskeletal organization defects and abortive activation in human oocytes after IVF and ISCI failure," Mol. Human. Reprod., 6:510-516 (2000).
Redacted email received by Dr. Reijo-Pera, 1 page (dated Nov. 21, 2010).
Redline comparison between "Ramsing, N.B. et al., 'Morphokinetic analysis of embryo development,' Unisense FertiliTech, Version 027, pp. 1-14 (Jun. 15, 2011)" and "Ramsing, N.B. et al., 'Morphokinetic analysis of embryo development,' Unisense FertiliTech, Version F7.797.4, pp. 1-15 (Nov. 16, 2011)," 17 pages, (2012).
Request for Inter Partes Reexamatintion (dated Oct. 14, 2011), Certification (dated Jun. 8, 2012) and Office Action (dated Jun. 11, 2012) for U.S. Appl. No. 95/001,785.
Response to Inter Partes Reexamination Office Action (dated Sep. 11, 2012).
Rienzi, L. et al., "Significance of morphological attributes of the early embryo," Reprod. BioMed. Online, 10(5):669-681 (2005).
Rijinders, P. M. et al., "The predictive value of day 3 embryo morphology regarding blastocyst formation, pregnancy, and implantation rate after day 5 transfer following in vitro fertilization or intracytoplasmic sperm injection," Human Reproduction, 13(10):2869-2873 (1998).
Rosenbusch, B. E., "Mechanisms giving rise to triploid zygotes during assisted reproduction," Fertility and Sterility, 90(1):49-55 (2008).
Rossant, J. et al., "Lineage allocation and asymmetries in the early mouse embryo," Phil. Tran. R. Soc. Lond., 358:1341-1348 (2003).
Safran, et al. (2000) "Blastocyst Culture in Evaluating Embryos of Reduced Quality," Reproductive Techologies, 10(3):154-157.
Sakkas, D. et al., "Early cleavage of human embryos to the two-cell stage after intracytoplasmic sperm injection as an indicator of embryo viability," Hum. Reprod., 13(1):182-187 (1998).
Salumets, et al. (2001) "The predictive value of pronuclear morphology of zygotes in the assessment of human embryro quality," Hum. Reprod. 16(10):2177-2181.

(56) References Cited

OTHER PUBLICATIONS

Sathananthan, A. H. et al., "Development of the human dispermic embryo," Human Reproduction Update, 5(5):553-560 (1999).
Schatten et al. (2005) "The significance of mitochondria for embryo developmen in cloned farm animals," Mitochondrion, 5(5):303-321.
Scott, L. et al., "Symposium: Innovative techniques in human embryo viability assessment. Human oocyte respiration-rate measurement-potential to improve oocyte and embryo selection?" Reprod. BioMed. Online, 17(4):461-469 (2008).
Seli, E. et al., "OMICS in assisted reproduction: possibilities and pitfalls," Mol. Hum. Reprod., 16(8):513-530 (2010).
Selman (1982) "Determination of the first two cleavage furrows in developing eggs of *Triturus alpestris* compared with other forms," Develop. Growth and Differ. 24(1):1-6.
Sepulveda, S. et al., "In vitro development and pregnancy outcomes for human embryos cultured in either a single medium or in a sequential media system," Fertil. Steril., 91(5):1765-1770 (2009).
Shahine, L. K. et al., "Day 2 versus day 3 embryo transfer in poor responders: a prospective randomized trial," Fertility and Sterility, 95(1):330-332 (2011).
Shen, S. et al., "Day 2 transfer improves pregnancy outcome in in vitro fertilization cycles with few available embryos," Fertility and Sterility, 86(1):44-50 (2006).
Shi, J. et al., "Good features to track," Proceedings of CVPR, pp. 593-600 (1994) (contains duplicate pages for figure clarity).
Shoukir et al., "Early cleavage of in-vitro fertilized human embryos to the 2-cell stage: a novel indicator of embryo quality and viability," Hum. Reprod. 12(7):1531-1536 (1997).
Sifer, C. et al., "An auto-controlled prospective comparison of two embryos culture media (G III series versus ISM) for IVF and ICSI treatments," J. Assist. Reprod. Genet., 26:575-581 (2009).
Squirrell, et al. (2003) "Imaging Mitochondrial Organization in Living Primate Oocytes and Embyros Using Multiphoton Microscopy," Microsc. Microanal. 9:190-201.
Squirrell, J. M. et al., "Long-term two-photon fluorescence imaging of mammalian embryos without compromising viability," Nat. Biotech., 17:763-767 (1999).
Sterckx et al., "Patenting time-lapse microscopy: the European story," Reprod. BioMed. Online (2013), doi: http://dx.doi.org/10.1016/j.rbmo.2013.09.018.
Sterckx et al., "Stanford University's patent on embryo selection should be excluded under European patent law," Reprod. BioMed. Online (2013), doi: http://dx.doi.org/10.1016/j.rbmo.2013.11.002.
Stojkovic, M. et al., "Derivation of a human blastocyst after heterologous nuclear transfer to donated oocytes," Reprod. BioMed. Online, 11(2):226-231 (2005).
Taft, R. E., "Virtues and limitations of the preimplantation mouse embryo as a model system," Theriogenology, 69:10-16 (2008).
Takenaka, M. et al., "Effects of light on development of mammalian zygotes," PNAS, 104(36):14289-14293 (2007).
Tam, P. P. L. et al., "Gene function in mouse embryogenesis: get set for gastrulation," Nature Reviews, 8:368-381 (2007).
Tam, P. P. L. et al., "The Allocation of Epiblast Cells to Ectodermal and Germ-Line Lineages is Influenced by the Position of the Cells in the Gastrulating Mouse Embryo," Devel. Biol., 178:124-132 (1996).
Tarin, J. J. et al., "Origin and ploidy of multipronuclear zygotes," Reprod. Fertil. and Devel., 11:273-279 (1999).
Tarkowski, A. K. et al., "Experiments on the development of isolated blastomeres of mouse eggs," Nature, 184:1286-1287 (1959).
Terriou, P. et al., "Relationship between even early cleavage and day 2 embryo score and assessment of their predictive value for pregnancy," Reprod. Biomed. Online, 14(3):294-299 (2007).
Third Party Observations for European Application No. 10748195.4, dated Aug. 31, 2012, 28 pages.
Third Party Requestor's comments to Patent Owner's Response (dated Oct. 11, 2012) for Inter Partes Reexamination Application 95/001,785.

Tokura, et al. (1993) "Sequential observation of mitochondrial distribution in mouse oocytes and embryos," J. Assisted Reprod. and Genet. 10(6):417-426.
Trounson et al., "Maturation of human oocytes in vitro and their developmental competence," Reproduction 121:51-75 (2001).
Trounson, A., "Comparative embryo transfer in Australia," Theriogenology, 19(1):17-29 (1983).
Ugajin, T. et al., "Aberrant behavior of mouse embryo development after blastomere biopsy as observed through time-lapse cinematography," Fertil. Steril., 93(8):2723-2728 (2010).
Vajta, G. et al., "Rapid growth and elongation of bovine blastocysts in vitro in a three-dimensional gel system," Theriogenology, 62:1253-1263 (2004).
Van Blerkom, et al. (2001) "A microscopic and biochemical study of fragmentation phenotypes in stage appropriate human embryos," Human Reprod. 16(4):719-729.
Van Blerkom, J. et al., "Differential mitochondrial distribution in human pronuclear embryos leads to disproportionate inheritance between blastomeres: relationship to microtubulor organization, ATP content and competence," Human Reproduction, 15(12):2621-2633 (2000).
Van De Velde, H. et al., "The four blastomeres of a 4-cell stage human embryo are able to develop individually into blastocysts with inner cell mass and trophectoderm," Hum. Reprod., 23(8):1742-1747 (2008).
Van Langendonckt, A. et al., "Comparison of G1.2/G2.2 and Sydney IVF cleavage/blastocyst sequential media for the culture of human embryos: a prospective, randomized, comparative study," Fertil. Steril., 76(5):1023-1031 (2001).
Van Mootfoort, et al. (2004) "Early cleavage is a valuable addition to existing embryo selection parameters: a study using single embryo transfers," Human Reprod. 19(9):2103-2108.
Van Voorhis, B. J., "In vitro fertilization," The New England Journal of Medicine, 356(4):379-386 (2007).
Vanderwall, D. K., "Early embryonic development and evaluation of equine embryo viability," Vet. Clin. North Am. Equine. Pract., 12(1):61-83 (1996) (Abstract Only).
Vanneste, E. et al., "Chromosome instability is common in human cleavage-stage embryos," Nature Medicine, 15(5):577-583 (2009).
Veeck, L. L., Atlas of the Human Oocyte and Early Conceptus, 2:121-149 (1991).
Vejlsted, M. et al., "Post-hatching development of the porcine and bovine embryo—defining criteria for expected development in vivo and in vitro," Theriogenology, 65:153-165 (2006).
Wagner et al., "Hematopoietic Progenitor Cells and Cellular Microenvironment: Behavioral and Molecular Changes upon Interaction," Stem Cells 23:1180-1191 (2005).
Wale, P. L. et al., "Time-lapse analysis of mouse embryo development in oxygen gradients," Reprod. BioMed. Onine, 21:402-410 (2010).
Weitzman et al., "Predictive value of embryo grading for embryos with known outcomes," Fertil. Steril. 93(2):658-662 (2010).
Wells, D. et al., "Association of abnormal morphology and altered gene expression in human preimplantation embryos," Fertility and Sterility, 84(2):343-355 (2005).
Wiley, L. M. et al., "Morphology of mouse egg cylinder development in vitro: a light and electron microscopic study," J. Exp. Zool., 200:389-402 (1977).
Windt, et al. (2004) "Comparative analysis of pregnancy rates after the transfer of early dividing embryos versus slower dividing embryos," Human Reprod. 19(5):1155-1162.
Wong et al., "Non-invasive imaging of human embryos before embryonic genome activation predicts development to the blastocyst stage," Nat. Biotechnol. 28:1115-1121 (2010).
Wong et al., "Non-invasive imaging of human embryos before embryonic genome activation predicts development to the blastocyst stage," Nat. Biotechnol. 28:1115-1121 (2010) supplemental data.
Written Opinion from PCT Application No. PCT/US2011/053537, dated Apr. 6, 2012 (10 pages).
Written Opinion of the International Searching Authority, PCT appl. No. PCT/US2012/026328, 8 pages (Aug. 3, 2012).

(56) References Cited

OTHER PUBLICATIONS

Written Opinion of the International Searching Authority, PCT appl. No. PCT/US2013/043639, 8 pages (Nov. 22, 2013).
Yamagata et al., "Long-term, six-dimensional live-cell imaging for the mouse preimplantation embryo that does not affect full-term development," J. Reprod. Dev., 55(3):343-350 (2009).
Yang, X. et al., "Nuclear reprogramming of cloned embryos and its implications for therapeutic cloning," Nature Genetics, 39(3):295-302 (2007).
Yu and Omholt (1999) "Early developmental processes in the fertilised honybee (*Apis mellifera*) oocyte," J. Insect Physiology 45:763-767.
Zeiss, Carl. "Cells Need the Perfect Climate" Carl Zeiss MicroImaging GmbH, Feb. 2008, pp. 1-42. retrieved on Aug. 14, 2014 from internet URL https://www.micro-shop.zeiss.com/index.php.
Zernicka-Goetz, M. et al., "Making a firm decision: multifaceted regulation of cell fate in the early mouse embryo," Nature Reviews, Genetics, 10:467-477 (2009) (contains duplicate pages for figure clarity).
Zernicka-Goetz, M., "Cleavage pattern and emerging asymmetry of the mouse embryo," Nature Reviews Mol. Cell Bio., 6:919-928 (2005).
Zernicka-Goetz, M., "First Cell fate decisions and spatial patterning in the early mouse embryo," Seminars in Cell Dev. Bio., 15:563-572 (2004).
Zernicka-Goetz, M., "Patterning of the embryo: the first spatial decisions in the life of a mouse," Development, 129:815-829 (2002).
Zernicka-Goetz, M., "The first cell-fate decisions in the mouse embryo: destiny is a matter of both chance and choice," Curr. Opin. Genet. Dev. 16:406-412 (2006).
Zhang, J. Q. et al., "Reduction in exposure of human embryos outside the incubator enhances embryo quality and blastulation rate," Reprod. Biomed. Online, 20:510-515 (2010).
Zheng and Dean, "Oocyte-Specific Genes Affect Folliculogenesis, Fertilization, and Early Development," Semin. Reprod. Med. 25(4):243-251 (2007).
Zhong, X., "High-resolution 3D reconstruction of the surface of live early-stage toad embryo," Project Report, (2005).
Ziebe, et al. (1997) "Embryo morphology or cleavage stage: how to select the best embryos for transfer after in vitro fertilization," Human Reprod. 12(7):1545-1549.
Ziebe, S. et al., "FISH analysis for chromosomes 13, 16, 18, 21, 22, X and Y in all blastomeres of IVF pre-embryos from 144 randomly selected donated human oocytes and impact on pre-embryo morphology," Human Reproduction, 18(12):2575-2581 (2003).
Zimmer, C. et al., "Segmentation and Tracking of Migrating Cells in Videomicroscopy with Parametric Active Contours: A Tool for Cell-Based Drug Testing," IEEE Transactions on Medical Imaging, 21(10):1212-1221 (2002).
Zollner, K. P. et al., "Comparison of two media for sequential culture after IVF and ICSI shows no differences in pregnancy rates: a randomized trial," Med. Sci. Monit., 10:CR1-CR7 (2004).
Zucker, R. M. et al., "Confocal Laser Scanning Microscopy of Apoptosis in Organogenesis-Stage Mouse Embryos," Cytometry, 33:348-354 (1998).

\* cited by examiner

FIG. 37

| Pt Name | Pt ID | Pt DOB | Start Date/Time | Status |
|---|---|---|---|---|
| Jane Doe | 1234567890123456 | 1985-Jul-01 | 2011-Jul-18 11:00 | Scope 1 |
| Elizabeth Jones | 2345678901234561 | 1984-Jun-30 | 2011-Apr-23 06:45 | Complete |
| Mary Smith | 3456789012345612 | 1990-Feb-28 | 2011-Jul-19 08:32 | Scope 2 |
| Abigail Young | 4567890123456123 | 1987-Nov-12 | 2011-Jul-19 09:14 | Complete |
| Rachel Thomas | 5678901234561234 | 1986-Mar-09 | 2011-May-25 08:12 | Complete |
| Misty Edwards | 6789012345612345 | 1988-Jun-17 | 2011-Jul-18 09:14 | Scope 4 |
| Julia Childs | 7890123456123456 | 1988-Jul-12 | 2011-Feb-19 09:22 | Complete |
| Abigail VanBuren | 8901234561234567 | 1982-Jan-04 | 2011-Jul-20 07:32 | Scope 5 |
| Stacey Lewis | 9012345612345678 | 1983-Dec-31 | 2011-Jun-12 15:22 | Complete |
| Carrie Fisher | 0123456123456789 | 1987-May-23 | 2011-Jul-18 13:23 | Complete |

FIG. 40

APPARATUS, METHOD, AND SYSTEM FOR THE AUTOMATED IMAGING AND EVALUATION OF EMBRYOS, OOCYTES AND STEM CELLS

CROSS-REFERENCE TO RELATED APPLICATION

The present application claims the benefit of U.S. Provisional Application No. 61/386,765, filed on Sep. 27, 2010, the disclosure of which is incorporated herein by reference in its entirety.

FIELD OF THE INVENTION

This invention relates to the field of biological and clinical testing, and particularly the imaging and evaluation of zygotes, embryos, oocytes, and stem cells from both humans and animals.

BACKGROUND OF THE INVENTION

Infertility is a common health problem that affects 10-15% of couples of reproductive-age. In the United States alone in the year 2006, approximately 140,000 cycles of in vitro fertilization (IVF) were performed (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

Traditionally in IVF clinics, human embryo viability has been assessed by simple morphologic observations such as the presence of uniformly-sized, mononucleate blastomeres and the degree of cellular fragmentation (Rijinders P M, Jansen C A M. (1998) Hum Reprod 13:2869-73; Milki A A, et al. (2002) Fertil Steril 77:1191-5). More recently, additional methods such as extended culture of embryos (to the blastocyst stage at day 5) and analysis of chromosomal status via preimplantation genetic diagnosis (PGD) have also been used to assess embryo quality (Milki A, et al. (2000) Fertil Steril 73:126-9; Fragouli E, (2009) Fertil Steril June 21 [EPub ahead of print]; El-Toukhy T, et al. (2009) Hum Reprod 6:20; Vanneste E, et al. (2009) Nat Med 15:577-83). However, potential risks of these methods also exist in that they prolong the culture period and disrupt embryo integrity (Manipalviratn S, et al. (2009) Fertil Steril 91:305-15; Mastenbroek S, et al. (2007) N Engl J Med. 357:9-17).

Recently it has been shown that time-lapse imaging can be a useful tool to observe early embryo development. Some methods have used time-lapse imaging to monitor human embryo development following intracytoplasmic sperm injection (ICSI) (Nagy et al. (1994) Human Reproduction. 9(9):1743-1748; Payne et al. (1997) Human Reproduction. 12:532-541). Polar body extrusion and pro-nuclear formation were analyzed and correlated with good morphology on day 3. However, no parameters were correlated with blastocyst formation or pregnancy outcomes. Other methods have looked at the onset of first cleavage as an indicator to predict the viability of human embryos (Fenwick, et al. (2002) Human Reproduction, 17:407-412; Lundin, et al. (2001) Human Reproduction 16:2652-2657). However, these methods do not recognize the importance of the duration of cytokinesis or time intervals between early divisions.

Other methods have used time-lapse imaging to measure the timing and extent of cell divisions during early embryo development (WO 2007/144001). However, these methods disclose only a basic and general method for time-lapse imaging of bovine embryos, which are substantially different from human embryos in terms of developmental potential, morphological behavior, molecular and epigenetic programs, and timing and parameters surrounding transfer. For example, bovine embryos take substantially longer to implant compared to human embryos (30 days and 9 days, respectively). (Taft, (2008) Theriogenology 69(1):10-16. Moreover, no specific imaging parameters or time intervals are disclosed that might be predictive of human embryo viability.

More recently, time-lapse imaging has been used to observe human embryo development during the first 24 hours following fertilization (Lemmen et al. (2008) Reproductive BioMedicine Online 17(3):385-391). The synchrony of nuclei after the first division was found to correlate with pregnancy outcomes. However, this work concluded that early first cleavage was not an important predictive parameter, which contradicts previous studies (Fenwick, et al. (2002) Human Reproduction 17:407-412; Lundin, et al. (2001) Human Reproduction 16:2652-2657).

Finally, no studies have validated the imaging parameters through correlation with the molecular programs or chromosomal composition of the embryos. Methods of human embryo evaluation are thus lacking in several respects, including their inability to conduct the imaging and evaluation in an automated fashion.

It is against this background that a need arose to develop the apparatus, method, and system for the automated imaging and evaluation of embryos, oocytes, and stem cells described herein.

SUMMARY OF THE INVENTION

Apparatuses, methods, and systems for automating the imaging and evaluation of one or more embryos or pluripotent cells are provided. These apparatuses, methods, and systems find use at least in identifying embryos and oocytes in vitro that have a good developmental potential, i.e., the ability or capacity to develop into a blastocyst, which are thus useful in methods of treating infertility in humans, and the like.

In one embodiment, an apparatus for automated imaging and evaluation of human embryos, oocytes, or pluripotent cells for use with an incubator includes: (1) at least one housing; (2) at least one time-lapse microscope placed inside the housing and having at least one light source and at least one imaging camera; (3) at least one loading platform extending outward from the housing, the loading platform for securing a multi-well culture dish holding a plurality of human embryos or pluripotent cells; (4) a computer for storing images from the at least one imaging camera and programmed for analyzing image sequences over time; and (5) at least one touch screen panel coupled to the computer and displaying a graphical user interface for controlling the at least one time-lapse microscope.

In one embodiment, a method for the automated imaging and evaluation of human embryos, oocytes, or pluripotent cells includes: (1) placing at least one human embryo or pluripotent cell in a multi-well culture dish; (2) loading the multi-well culture dish in a loading platform of an imaging system having at least one time-lapse microscope inside a housing; (3) if needed, adjusting the loading of the multi-well culture dish into the loading platform to verify a position and orientation of the multi-well culture dish; (4) acquiring time-lapse images of the multi-well culture dish; (5) displaying the images captured by the at least one time-lapse microscope in a graphical user interface accessible by a touch-screen panel; and (6) analyzing the time-lapse images of the multi-well culture dish to determine a development potential of the at least one human embryo or pluripotent cell.

In one embodiment, an apparatus for automated imaging of human embryos, oocytes, or pluripotent cells includes: (1) a culture chamber configured to incubate a multi-well culture dish, the culture chamber having an upper surface including a first window and a lower surface including a second window; (2) a time-lapse microscope including a light source and an imaging camera configured to generate images of the multi-well culture dish inside the culture chamber based on light from the light source passing through the first window and the second window, where the culture chamber and the time-lapse microscope are integrated in a common housing; and (3) a touch-screen panel configured to display a graphical user interface for controlling the time-lapse microscope.

In one embodiment, a system for automated imaging and evaluation of human embryos, oocytes, or pluripotent cells for use with an incubator includes: (1) a plurality of imaging microscopes, each of the plurality of imaging microscopes being located inside a corresponding one of a plurality of housings and including at least one light source and at least one imaging camera, where each of the plurality of housings is located inside the incubator; (2) a loading platform extending outward from each of the plurality of housings, the loading platform for securing a multi-well culture dish holding a plurality of human embryos or pluripotent cells; (3) a controller electrically connected to each of the plurality of imaging microscopes, where the controller is located outside of the incubator and controls the at least one light source; and (4) a computer for storing images from the at least one imaging camera and programmed for analyzing image sequences over time, where the computer is electrically connected to each of the plurality of imaging microscopes via the controller.

In one embodiment, a method for automated evaluation and display of human embryos, oocytes, or pluripotent cells includes: (1) collecting images of a plurality of multi-well culture dishes, each of the plurality of multi-well culture dishes including a plurality of micro-wells, at least one of the plurality of micro-wells containing at least one of a human embryo or a pluripotent cell; (2) analyzing the images of the plurality of multi-well culture dishes; and (3) concurrently displaying status information associated with each of the plurality of multi-well culture dishes.

In one embodiment, a system for automated imaging and evaluation of human embryos, oocytes, or pluripotent cells includes: (1) a plurality of time-lapse microscopes, each of the plurality of time-lapse microscopes being located inside a corresponding plurality of housings and including at least one light source and at least one imaging camera, where each of the plurality of housings is located inside the incubator; (2) a loading platform extending outward from each of the plurality of housings, the loading platform for securing at least one multi-well culture dish holding a plurality of human embryos or pluripotent cells; (3) a computer electrically connected to the plurality of time-lapse microscopes; and (4) a server configured to communicate with the computer over a network, and configured to display a graphical user interface that provides status information and parameters determined based on analysis of images of a human embryo or pluripotent cell contained in the at least one multi-well culture dish. The status information is associated with each of the plurality of time-lapse microscopes, and at least one of the images is generated by each of the plurality of time-lapse microscopes.

An apparatus and method for automated dish detection and well occupancy determination are also provided. The apparatus and method find use at least in facilitating identification of embryos and oocytes in vitro that are most useful in treating infertility in humans.

In one embodiment, an apparatus for automated dish detection and well occupancy determination includes: (1) a dish detection module configured to detect presence of a multi-well culture dish in an image detected by an imaging camera; (2) a well location determination module configured to determine a position of each of a plurality of micro-wells included in the multi-well culture dish; (3) a well occupancy determination module configured to determine occupied micro-wells included in the plurality of micro-wells based on the position of the each of the plurality of micro-wells; and (4) a display module configured to display at least the occupied micro-wells. At least one of the dish detection module, the well location determination module, the well occupancy determination module, or the display module are implemented in at least one of a memory or a processing device.

In one embodiment, a method for automated dish detection and well occupancy determination includes: (1) detecting presence of a multi-well culture dish in an image detected by an imaging camera; (2) determining the position of each of a plurality of micro-wells included in the multi-well culture dish; (3) determining occupied micro-wells included in the plurality of micro-wells based on the position of the each of the plurality of micro-wells; and (4) displaying at least the occupied micro-wells.

A multi-well culture dish is also provided. The multi-well culture dish finds use at least in facilitating identification of embryos and oocytes in vitro that are most useful in treating infertility in humans.

In one embodiment, a multi-well culture dish includes: (1) a ring disposed on a lower surface of the culture dish, the ring defining a cavity and having an upper surface, an outer lateral surface, and an inner lateral surface, the cavity having a cavity bottom; and (2) a plurality of micro-wells defined by the cavity bottom, each micro-well configured to hold a human embryo or a pluripotent cell. The inner lateral surface of the ring is disposed between the outer lateral surface and the plurality of micro-wells, and extends from the upper surface of the ring to the cavity bottom. The inner lateral surface of the ring slopes toward the plurality of micro-wells such that a first width of the ring at the lower surface of the culture dish is greater than a second width of the ring at the upper surface of the ring.

In one embodiment, a multi-well culture dish includes: (1) a ring disposed on a lower surface of the culture dish, the ring defining a cavity and having an upper surface, an outer lateral surface, and an inner lateral surface, the cavity having a cavity bottom; and (2) a plurality of micro-wells defined by the cavity bottom, each micro-well configured to hold a human embryo or a pluripotent cell. A lower surface of at least one of the plurality of micro-wells is curved or conical.

An illumination assembly for bimodal imaging is also provided. The illumination assembly for bimodal imaging finds use at least in facilitating identification of embryos and oocytes in vitro that are most useful in treating infertility in humans.

In one embodiment, an illumination assembly for bimodal imaging includes: (1) a first light source; (2) a condenser lens; (3) a darkfield aperture having a first surface configured to block light and having a second surface opposite to the first surface, the darkfield aperture defining at least one opening; and (4) a second light source attached to the second surface of the darkfield aperture. In a first mode of the illumination assembly, the first light source generates light that traverses the at least one opening in the darkfield aperture and the condenser lens prior to reaching a sample, and the second light source does not generate light. In a second mode of the illumination assembly, the second light source generates light that reaches the sample without traversing the at least one opening in the darkfield aperture, and the first light source does not generate light.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 37-40 illustrate various display screens of a graphical user interface (GUI) for use with the dashboard of FIG. 36, according to an embodiment of the invention.

DETAILED DESCRIPTION OF THE INVENTION

Figure 1:
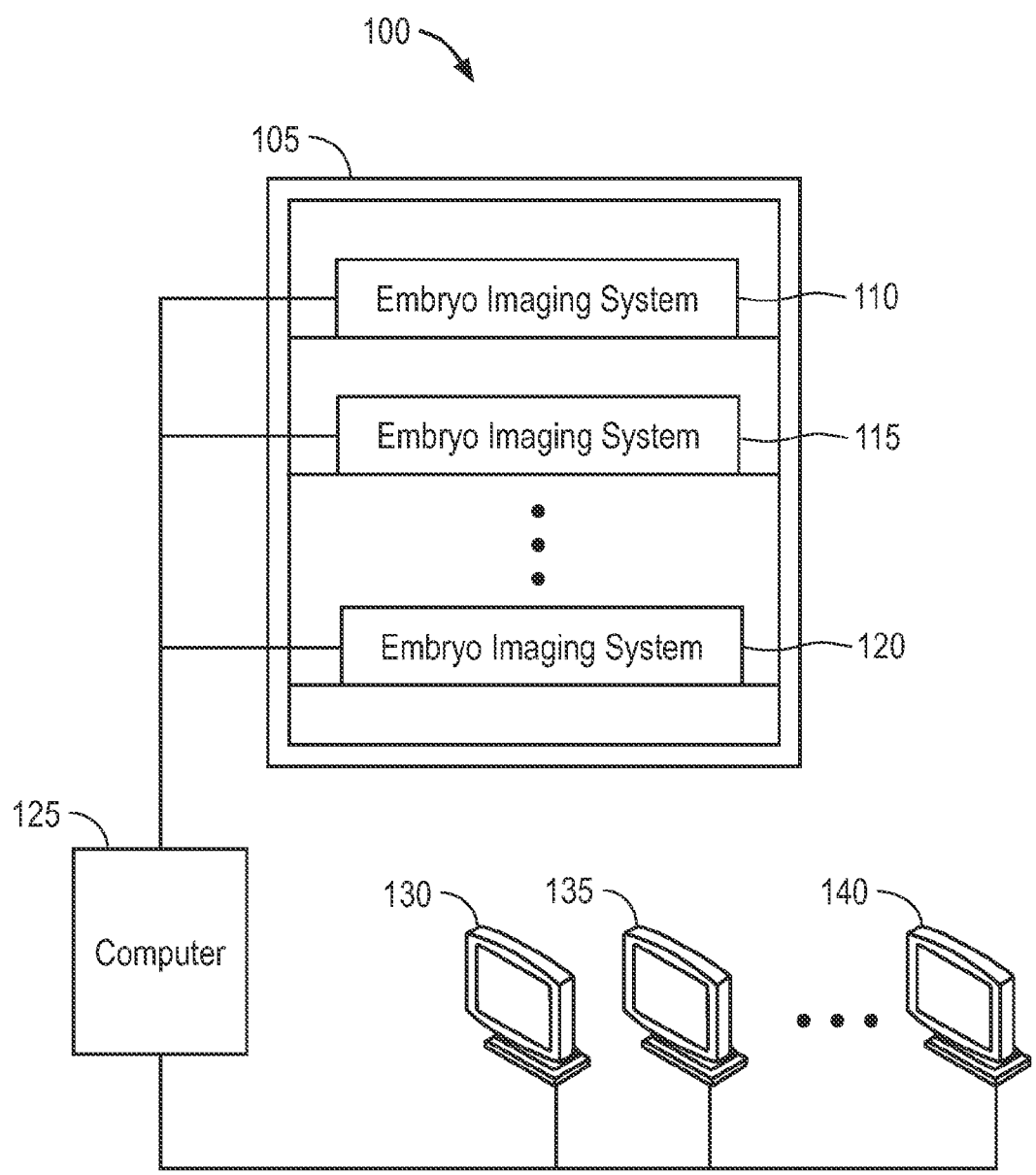
FIG. 1 illustrates a schematic diagram of an apparatus, according to an embodiment of the invention.

Before the present apparatuses, systems, and methods are described, it is to be understood that this invention is not limited to particular apparatus, system, or method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a computer" includes a plurality of such computers known to those skilled in the art, and so forth.

Any publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "developmental potential" and "developmental competence" are used herein to refer to the ability or capacity of a healthy embryo or pluripotent cell to grow or develop.

The term "embryo" is used herein to refer both to the zygote that is formed when two haploid gametic cells, e.g., an unfertilized secondary oocyte and a sperm cell, unite to form a diploid totipotent cell, e.g., a fertilized ovum, and to the embryo that results from the immediately subsequent cell divisions, i.e. embryonic cleavage, up through the morula, i.e. 16-cell stage and the blastocyst stage (with differentiated trophoectoderm and inner cell mass).

The term "pluripotent cell" is used herein to mean any cell that has the ability to differentiate into multiple types of cells in an organism. Examples of pluripotent cells include stem cells oocytes, and 1-cell embryos (i.e. zygotes).

The term "stem cell" is used herein to refer to a cell or a population of cells which: (a) has the ability to self-renew, and (b) has the potential to give rise to diverse differentiated cell types. Frequently, a stem cell has the potential to give rise to multiple lineages of cells. As used herein, a stem cell may be a totipotent stem cell, e.g. a fertilized oocyte, which gives rise to all of the embryonic and extraembryonic tissues of an organism; a pluripotent stem cell, e.g. an embryonic stem (ES) cell, embryonic germ (EG) cell, or an induced pluripotent stem (iPS) cell, which gives rise to all of embryonic tissues of an organism, i.e. endoderm, mesoderm, and ectoderm lineages; a multipotent stem cell, e.g. a mesenchymal stem cell, which gives rise to at least two of the embryonic tissues of an organism, i.e. at least two of endoderm, mesoderm and ectoderm lineages, or it may be a tissue-specific stem cell, which gives rise to multiple types of differentiated cells of a particular tissue. Tissue-specific stem cells include tissue-specific embryonic cells, which give rise to the cells of a particular tissue, and somatic stem cells, which reside in adult tissues and can give rise to the cells of that tissue, e.g. neural stem cells, which give rise to all of the cells of the central nervous system, satellite cells, which give rise to skeletal muscle, and hematopoietic stem cells, which give rise to all of the cells of the hematopoietic system.

The term "oocyte" is used herein to refer to an unfertilized female germ cell, or gamete. Oocytes of the subject application may be primary oocytes, in which case they are positioned to go through or are going through meiosis I, or secondary oocytes, in which case they are positioned to go through or are going through meiosis II.

By "meiosis" it is meant the cell cycle events that result in the production of gametes. In the first meiotic cell cycle, or meiosis I, a cell's chromosomes are duplicated and partitioned into two daughter cells. These daughter cells then divide in a second meiotic cell cycle, or meiosis II, that is not accompanied by DNA synthesis, resulting in gametes with a haploid number of chromosomes.

By a "mitotic cell cycle", it is meant the events in a cell that result in the duplication of a cell's chromosomes and the division of those chromosomes and a cell's cytoplasmic matter into two daughter cells. The mitotic cell cycle is divided into two phases: interphase and mitosis. In interphase, the cell grows and replicates its DNA. In mitosis, the cell initiates and completes cell division, first partitioning its nuclear material, and then dividing its cytoplasmic material and its partitioned nuclear material (cytokinesis) into two separate cells.

By a "first mitotic cell cycle" or "cell cycle 1" it is meant the time interval from fertilization to the completion of the first cytokinesis event, i.e. the division of the fertilized oocyte into two daughter cells. In instances in which oocytes are fertilized in vitro, the time interval between the injection of human chorionic gonadotropin (HCG) (usually administered prior to oocyte retrieval) to the completion of the first cytokinesis event may be used as a surrogate time interval.

By a "second mitotic cell cycle" or "cell cycle 2" it is meant the second cell cycle event observed in an embryo, the time interval between the production of daughter cells from a fertilized oocyte by mitosis and the production of a first set of granddaughter cells from one of those daughter cells (the "leading daughter cell", or daughter cell A) by mitosis. Upon completion of cell cycle 2, the embryo consists of 3 cells. In other words, cell cycle 2 can be visually identified as the time between the embryo containing 2-cells and the embryo containing 3-cells.

By a "third mitotic cell cycle" or "cell cycle 3" it is meant the third cell cycle event observed in an embryo, typically the time interval from the production of daughter cells from a fertilized oocyte by mitosis and the production of a second set of granddaughter cells from the second daughter cell (the "lagging daughter cell" or daughter cell B) by mitosis. Upon completion of cell cycle 3, the embryo consists of 4 cells. In other words, cell cycle 3 can be visually identified as the time between the embryo containing 3-cells and the embryo containing 4-cells.

By "first cleavage event", it is meant the first division, i.e. the division of the oocyte into two daughter cells, i.e. cell cycle 1. Upon completion of the first cleavage event, the embryo consists of 2 cells.

By "second cleavage event", it is meant the second set of divisions, i.e. the division of leading daughter cell into two granddaughter cells and the division of the lagging daughter cell into two granddaughter cells. In other words, the second cleavage event consists of both cell cycle 2 and cell cycle 3. Upon completion of second cleavage, the embryo consists of 4 cells.

By "third cleavage event", it is meant the third set of divisions, i.e. the divisions of all of the granddaughter cells. Upon completion of the third cleavage event, the embryo typically consists of 8 cells.

By "cytokinesis" or "cell division" it is meant that phase of mitosis in which a cell undergoes cell division. In other words, it is the stage of mitosis in which a cell's partitioned nuclear material and its cytoplasmic material are divided to produce two daughter cells. The period of cytokinesis is identifiable as the period, or window, of time between when a constriction of the cell membrane (a "cleavage furrow") is first observed and the resolution of that constriction event, i.e. the generation of two daughter cells. The initiation of the cleavage furrow may be visually identified as the point in which the curvature of the cell membrane changes from convex (rounded outward) to concave (curved inward with a dent or indentation). The onset of cell elongation may also be used to mark the onset of cytokinesis, in which case the period of cytokinesis is defined as the period of time between the onset of cell elongation and the resolution of the cell division.

By "first cytokinesis" or "cytokinesis 1" it is meant the first cell division event after fertilization, i.e. the division of a fertilized oocyte to produce two daughter cells. First cytokinesis usually occurs about one day after fertilization.

By "second cytokinesis" or "cytokinesis 2", it is meant the second cell division event observed in an embryo, i.e. the division of a daughter cell of the fertilized oocyte (the "leading daughter cell", or daughter A) into a first set of two granddaughters.

By "third cytokinesis" or "cytokinesis 3", it is meant the third cell division event observed in an embryo, i.e. the division of the other daughter of the fertilized oocyte (the "lagging daughter cell", or daughter B) into a second set of two granddaughters.

The term "fiduciary marker" or "fiducial marker," is an object used in the field of view of an imaging system which appears in the image produced, for use as a point of reference or a measure. It may be either something placed into or on the imaging subject, or a mark or set of marks in the reticle of an optical instrument.

The term "micro-well" refers to a container that is sized on a cellular scale, such as to provide for accommodating one or more eukaryotic cells.

DESCRIPTION OF EMBODIMENTS OF THE INVENTION

Referring to FIG. 1, a schematic diagram of an apparatus 100 according to an embodiment of the invention is described. The apparatus 100 includes a standard incubator 105 with one or more shelves for holding imaging systems 110-120, described in more detail hereinbelow. The imaging systems 110-120 have loading platforms and are placed inside the incubator 105 to image one or more embryos cultured in dishes mounted on their loading platforms.

The imaging systems 110-120 can be coupled to a computer 125, which may be mounted on or near the incubator 105. The computer 125 includes software for analyzing the images acquired by the imaging systems 110-120. In one embodiment, the computer 125 includes software for determining the developmental potential and/or the presence of chromosomal abnormalities in cultured embryos. The computer 125 is coupled to one or more touch-screen panels, e.g., touch-screen panels 130-140. The touch-screen panels 130-140 may be configured to enable users to control the operation of the imaging systems 110-120 with an easy-to-use graphical user interface ("GUI"). In one embodiment, multiple imaging systems, e.g., the systems 110-120, may be controlled from a single touch-screen panel, and multiple touch-screen panels may be controlled from a single computer, e.g., the computer 125.

Figure 2:
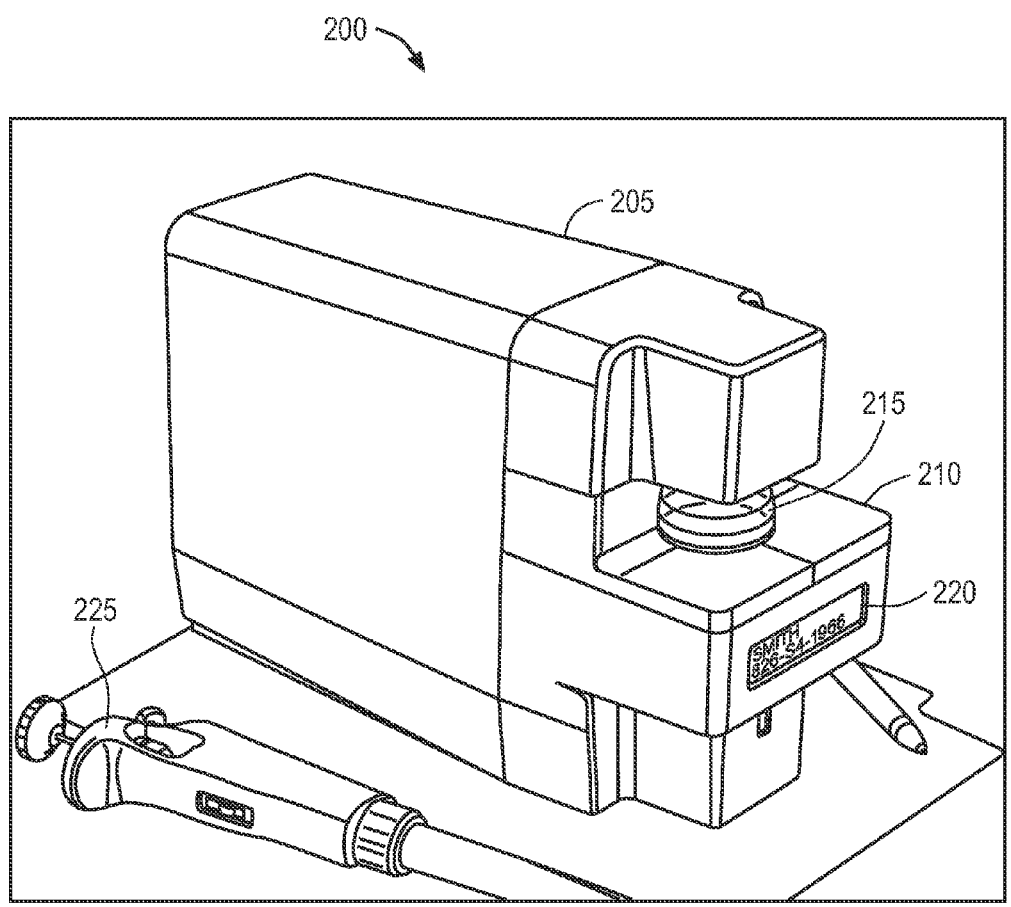
FIG. 2 illustrates a schematic diagram of an imaging system, according to an embodiment of the invention.

A schematic diagram of an imaging system 200 according to an embodiment of the invention is illustrated in FIG. 2. The imaging system 200 includes a single-channel or multi-channel microscope system including on-board electronics placed inside an outer housing 205. Referring to FIGS. 1 and 2, in one embodiment, the imaging system 200 may communicate with the computer 125. Alternatively, the imaging system 200 may communicate with a controller outside of the incubator 105 (see description with reference to FIG. 32) and may include a reduced set of on-board electronics. The remainder of the on-board electronics may be included in the controller. Housing 205 may be constructed of non-embryo-toxic materials, such as aluminum and plastics. In one embodiment, a loading platform 210 extending outward from the housing 205 allows for a multi-well culture dish 215 to be positioned for imaging by the microscope system. Alternatively, the multi-well culture dish 215 may be loaded in a culture chamber integrated in the housing 205 (see description with reference to FIG. 35). Embryos may be placed in dish 215 with pipette 225. In one embodiment, the microscope system includes software to monitor the loading of a dish 215 into loading platform 210 and make any adjustments necessary for the proper imaging of the embryos cultured in the dish.

It is appreciated that a single channel/microscope system may be used to image embryos for a single patient. It is also appreciated that imaging system 200 may be built as a single-channel microscope system as illustrated in FIG. 2, or it may be built as an integrated multi-channel microscope system. Accordingly, to facilitate the monitoring of embryos inside the incubator, a LCD display 220 may be placed outside the housing 205 for showing the patient name, ID number, and other patient information to help users identify which channel is assigned to each patient. Alternatively, a color code system or other identification mechanism may also be used to identify patients.

Figure 3:
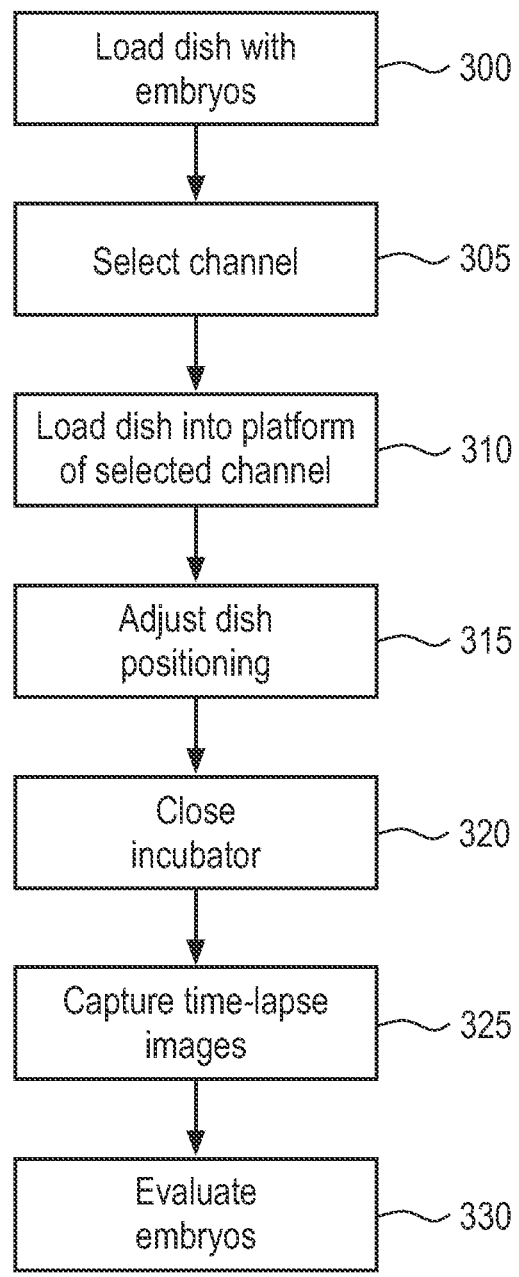
FIG. 3 illustrates a flow chart for operating an imaging system, according to an embodiment of the invention.

FIG. 3 illustrates a flow chart for operating an imaging system, according to an embodiment of the invention. The imaging system may be the imaging system 200 of FIG. 2, or other types of devices for imaging of embryos, oocytes, or pluripotent cells. A user loads a multi-well dish (such as the multi-well dish 215 of FIG. 2, the multi-well dish 900 of FIG. 9, or the multi-well dish 2600 of FIG. 26) with one or more embryos into loading platform 210 (300). Using a GUI on one of the touch-screen panels 130-140, the user selects a microscope channel in an imaging system to image the embryos (305). In doing so, the user inputs patient information (e.g., name, ID) in the GUI to facilitate patient's identification. The patient information can also be entered automatically using a bar-code scanner or other means. For example, a separate device such as a hand-held scanner could be used a priori to scan the bar-code on a multi-well dish. Then, when the dish is loaded into the imaging system 200, the bar-code can be scanned again (e.g., via a scanner built in to the imaging system or its platform) to identify the patient identification. The patient information can be displayed on an LCD screen on the imaging system, on the touch-screen panel outside the incubator, and elsewhere.

The multi-well dish can be placed on the loading platform of the selected channel in a given position and orientation (310), which may be adjusted by a software in the selected channel to ensure proper imaging of the embryos in the multi-well dish (315). In one embodiment, the software recognizes when the multi-well dish is loaded properly and alerts the user of its proper loading by a light emitting diode (LED) indicator or other alert mechanism. In addition, the dish may have a keying feature that allows loading of the dish in a single possible position and orientation.

After closing of the incubator door (320), the time-lapse imaging capture of the embryos can be initialized by first performing auto-focus and auto-exposure and verifying the quality of the acquired images (325). In one embodiment, images may be acquired at every given interval for a number of days. For example, images may be acquired every 1, 2, 3, 4, 5, 6, 7, 8, 9, 10, 15, 20, 25, or 30 minutes for 6 hours, 12 hours, 1 day, 2 days, 3 days, 4 days, 5 days, 6 days, 1 week, 2 weeks or 3 weeks.

Lastly, software in the selected channel and/or the computer 125 analyzes the captured images and measures predictive parameters to provide a prediction of which embryos will reach blastocyst and/or a ranking of embryo quality. The prediction performed enables the user to determine which embryos have development potential for human implantation.

Figure 4:
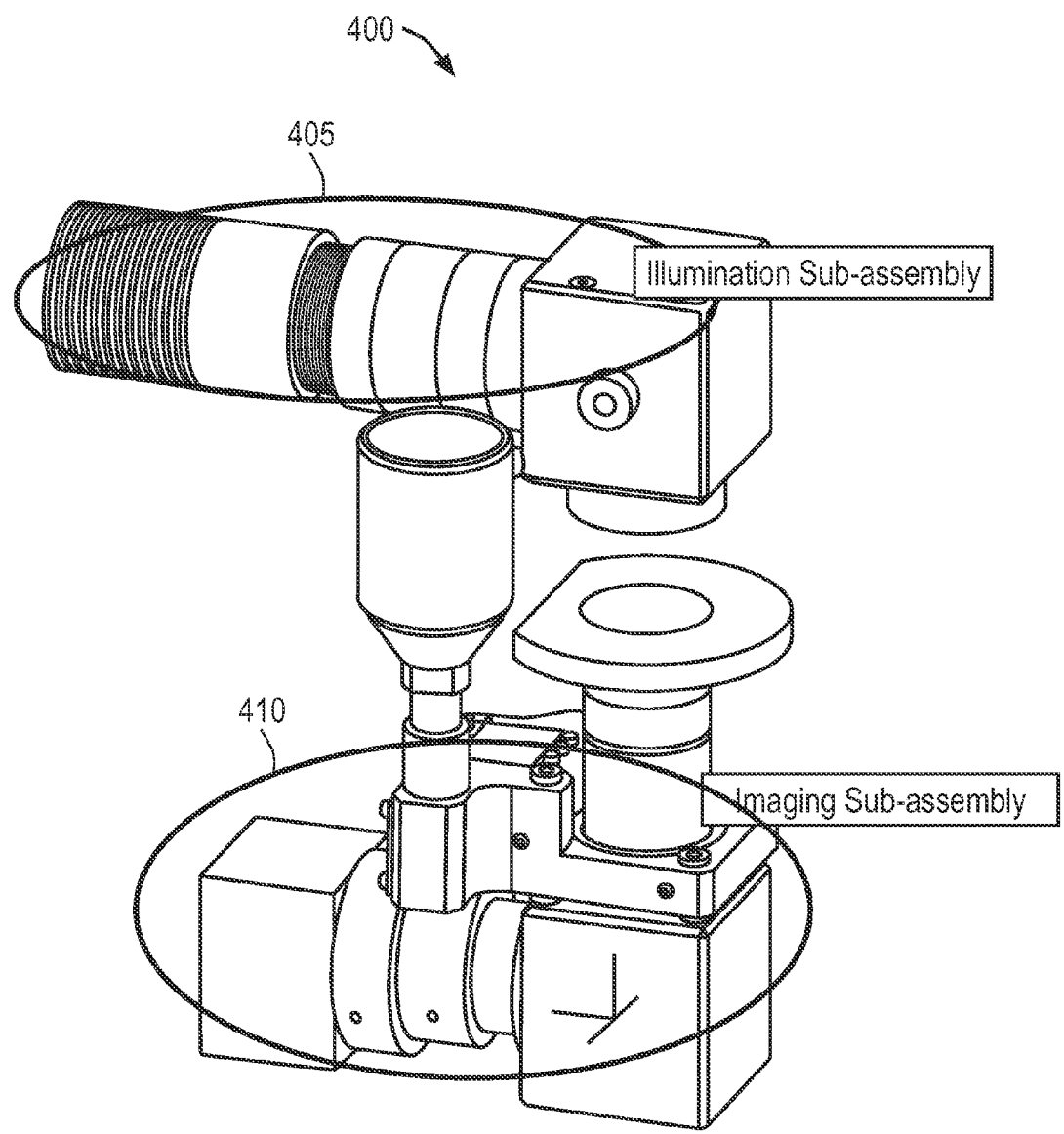
FIG. 4 illustrates a schematic diagram of a microscope placed inside an imaging system, according to an embodiment of the invention.

Referring now to FIG. 4, a schematic diagram of a microscope 400 placed inside an imaging system is described, according to an embodiment of the invention. The microscope 400 may be used with the imaging system 200 of FIG. 2, or other types of devices for imaging of embryos, oocytes, or pluripotent cells. The microscope 400 may be any computer-controlled microscope that is equipped for digital image storage and analysis. In one embodiment, the microscope 400 includes an illumination sub-assembly 405 and an imaging sub-assembly 410. In one embodiment, the illumination sub-assembly 405 provides darkfield illumination and may include a red LED, a collimating lens, a diffuser, a darkfield aperture, a right-angle mirror, and a condenser lens, among other optical components.

Imaging sub-assembly 410 may include an imaging objective lens (10×), a translation stage to focus the objective lens, a motor coupled to the translation stage to provide computer-controlled focus, a right-angle mirror, a 4× objective lens that acts as a high-quality tube lens, and a CMOS camera to capture images. It is appreciated that the field of view is large enough to view a set of micro-wells. It is also appreciated that some embodiments may use a light having a color other than red, a CCD camera, and different field of view, depth of field, optical layout, magnification objectives (e.g., 20×, 40×, etc.), motor, a positioning mechanism for moving a group of micro-wells under the field-of-view, and so on.

It is further appreciated that the microscope 400 may employ brightfield illumination, oblique brightfield, darkfield illumination, phase contrast, Hoffman modulation contrast, differential interference contrast, or fluorescence. In some embodiments, darkfield illumination may be used to provide enhanced image contrast for subsequent feature extraction and image analysis. Darkfield illumination can also be achieved using epi-illumination, where the illumination light comes up through the imaging objective and illuminates the sample from beneath, rather than from above.

Figure 5A:
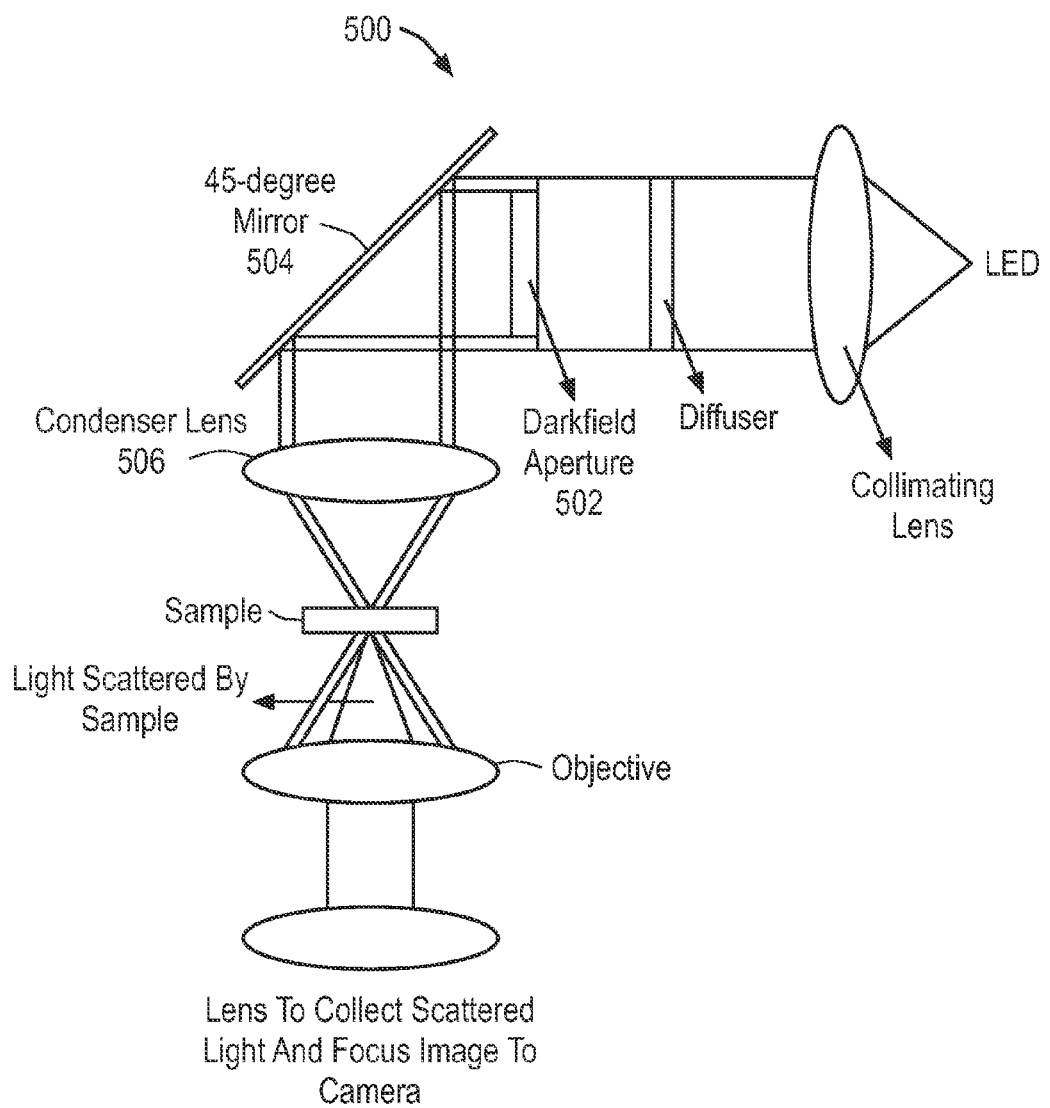
FIGS. 5A-C illustrate schematic views of examples of darkfield illumination systems that may be used by the microscope of FIG. 4, according to an embodiment of the invention.
Figure 5B:
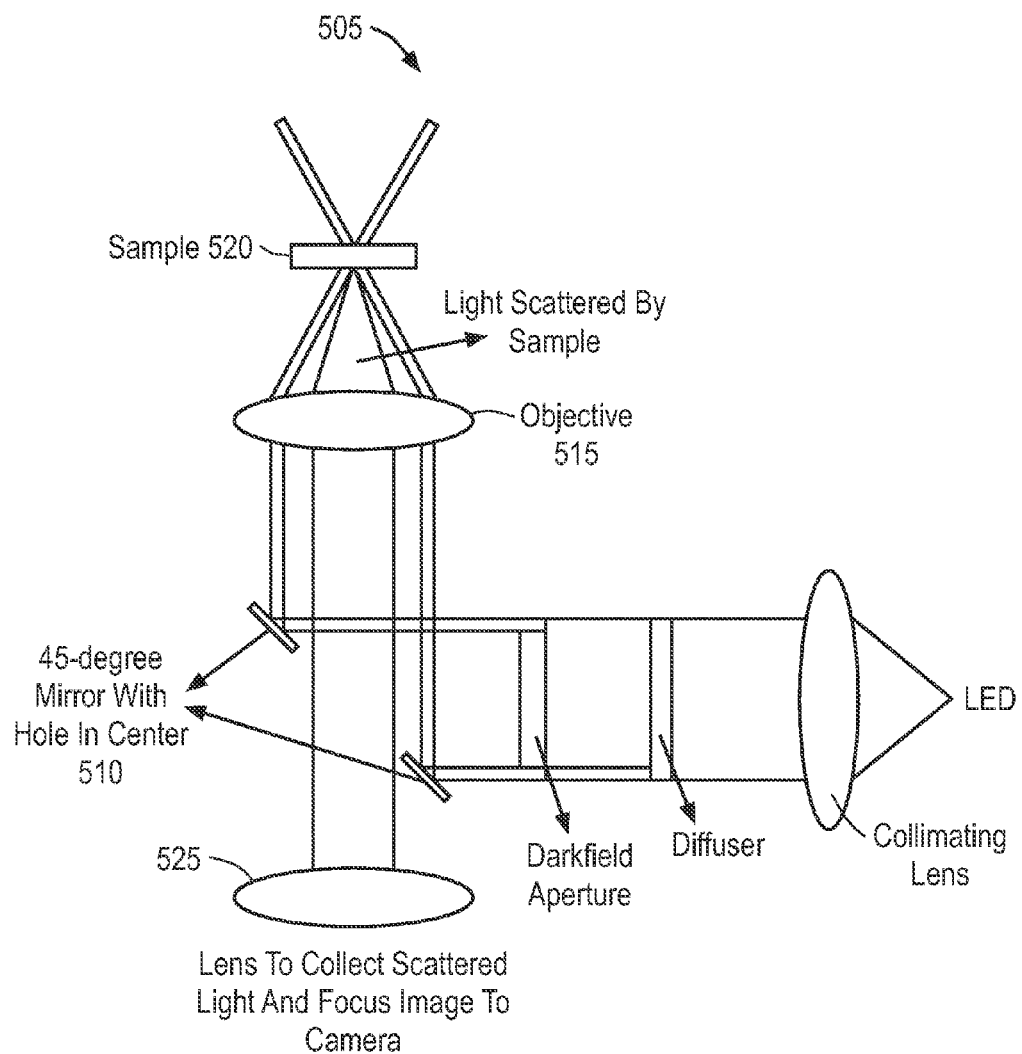
Figure 5C:
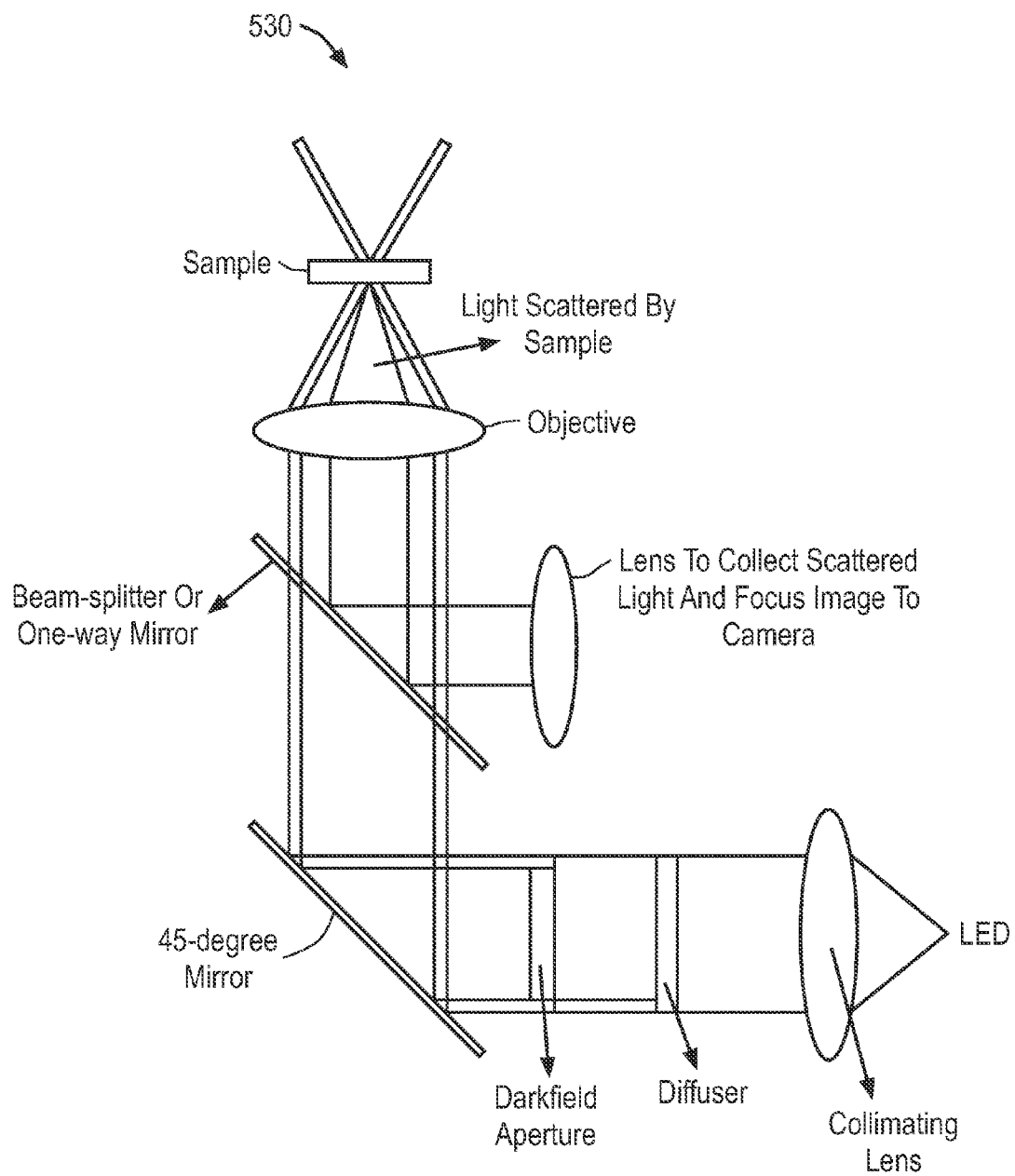

FIGS. 5A-C illustrate schematic views of examples of darkfield illumination systems that may be used by the microscope 400 of FIG. 4, according to an embodiment of the invention. Darkfield illumination system 500 of FIG. 5A illustrates an example of a traditional darkfield illumination approach for use with time-lapse microscopes such as the microscope 400, darkfield illumination system 505 of FIG. 5B illustrates an example of an approach using epi-illumination, and darkfield illumination system 530 of FIG. 5C illustrates another approach for epi-illuminated darkfield. In system 505, for example, a 45-degree mirror 510 with a circular hole in the middle can be placed under the imaging objective 515. A hollow cone of light is reflected off the mirror and up towards the imaging objective 515, where it gets focused to the sample 520. Light scattered by the sample 520 gets collected by the same imaging objective 515 and passes through the hole in the mirror 510 and towards a tube-lens and camera 525 for collecting the image. In addition, red or near-infrared light sources may be used to reduce phototoxicity and improve the contrast ratio between cell membranes and the inner portion of the cells. In other embodiments, images can be captured using one or more illumination wavelengths and the various images can be combined or used to provide additional information.

In one embodiment, a darkfield aperture 502 illustrated in FIG. 5A may be placed as shown. Alternatively, the darkfield aperture 502 may be placed in other configurations, such as between the 45-degree mirror 504 and the condenser lens 506, or after the condenser lens 506.

Images that are acquired by the microscope 400 may be stored either on a continuous basis, as in live video, or on an intermittent basis, as in time lapse photography, where a subject is repeatedly imaged in a still picture. In one embodiment, the time interval between images is between 1 to 30 minutes in order to capture significant morphological events as described below. In an alternative embodiment, the time interval between images can be varied depending on the amount of cell activity.

For example, during active periods images could be taken as often as every few seconds or every minute, while during inactive periods images could be taken every 10 or 15 minutes or longer. Real-time image analysis on the captured images could be used to detect when and how to vary the time intervals. It is appreciated that the light intensity for a time-lapse imaging system may be significantly lower than the light intensity typically used on an assisted reproduction microscope due to the low-power of the LEDs (for example, using a 1 W red LED compared to a typical 100 W Halogen bulb) and high sensitivity of the camera sensor. Thus, the total amount of light energy received by an embryo using the microscope 400 is comparable to or less than the amount of energy received during routine handling at an IVF clinic. For example, for 2 days of imaging, with images captured every 5 minutes at 0.5 seconds of light exposure per image, the total amount of low-level light exposure can be equivalent to roughly 30 seconds of exposure under a typical IVF inverted microscope.

Following image acquisition, the images are extracted and analyzed for different cellular parameters related to embryo, stem cell, and/or oocyte development, for example, cell size, thickness of the zona pellucida, degree of fragmentation, particle motion in the cytoplasm, symmetry of daughter cells resulting from a cell division, duration of first cytokinesis, time interval between cytokinesis 1 and cytokinesis 2, time interval between cytokinesis 2 and cytokinesis 3, and time intervals and durations of the first and second polar body extrusions.

Figure 30:
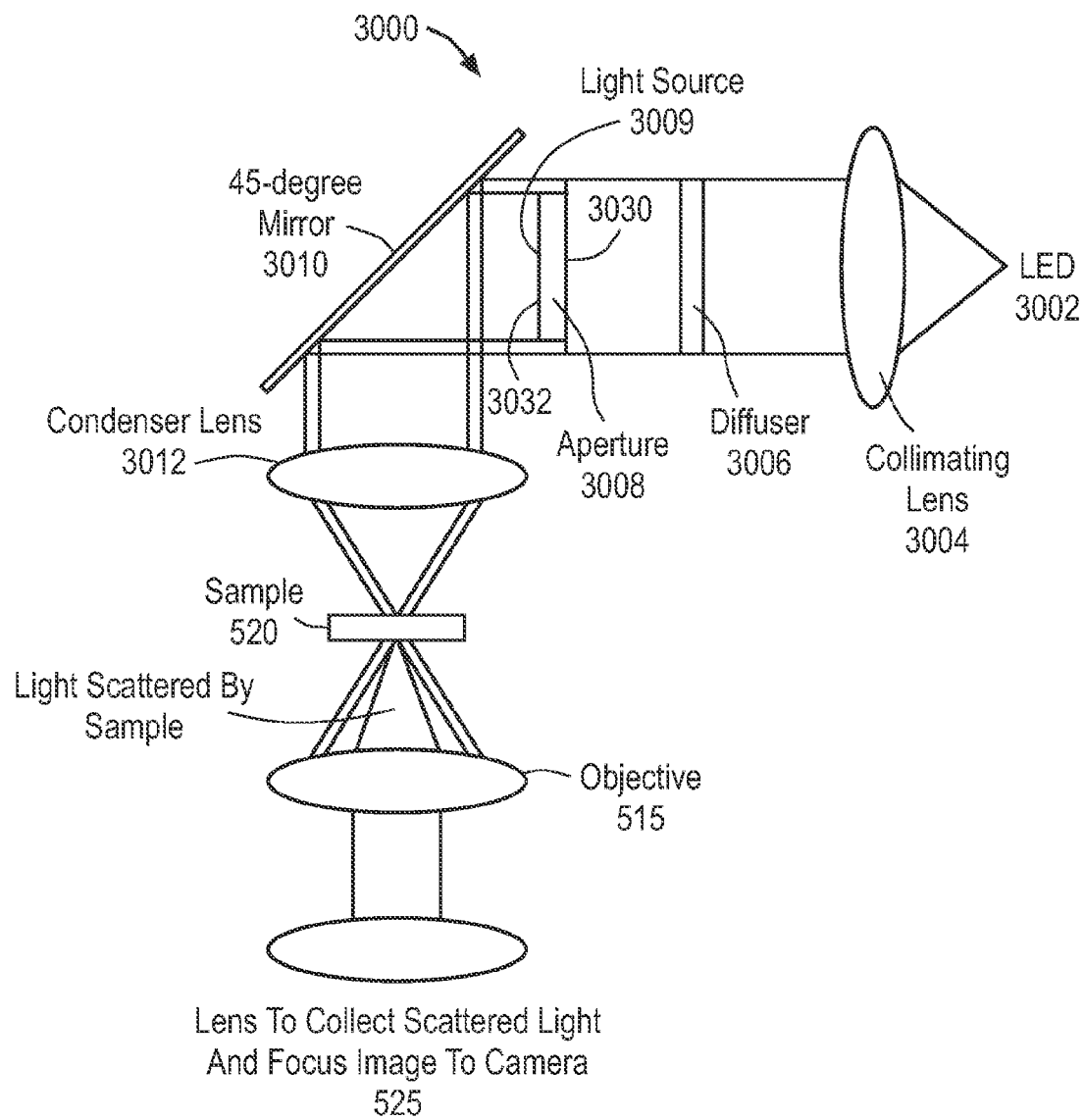
FIG. 30 illustrates a schematic view of bimodal illumination that may be used by the microscope of FIG. 4, according to one embodiment of the invention.

FIG. 30 illustrates a schematic view of bimodal illumination that may be used by the microscope 400 of FIG. 4, according to one embodiment of the invention. In one embodiment, an illumination assembly 3000 may include a first light source 3002, a an aperture 3008, a second light source 3009, and a condenser lens 3012, among other optical components. In one embodiment, the first light source 3002 and the second light source 3009 may be red LEDs. In one embodiment, the aperture 3008 may be a darkfield aperture having a first surface 3030 configured to block light and a second surface 3032 opposite to the first surface 3030. The aperture 3008 may define at least one opening 3102 (see FIG. 31) through which the hollow cone of light can pass. The second light source 3009 may be attached to the second surface 3032 of the aperture 3008.

In a first mode of the illumination assembly 3000, the first light source 3002 generates light that traverses a collimating lens 3004, the at least one opening 3102 (see FIG. 31) in the aperture 3008 and the condenser lens 3012 prior to reaching the sample 520. The aperture 3008 may be placed before or after the condenser lens 3012. The light may also traverse a diffuser 3006. The light that passes through the at least one opening 3102 may be reflected by the 45-degree mirror 3010. In one embodiment, a hollow cone of light passes through the at least one opening 3102 in the aperture 3008, while the remainder of the light is blocked by the aperture 3008. In the first mode, the second light source 3009 does not generate light. Light scattered by the sample 520 then traverses the imaging objective 515 and the tube-lens and camera 525 for collecting the image. As described, in the first mode of the illumination assembly 3000, the illumination assembly 3000 performs darkfield imaging.

In one embodiment, the aperture 3008 illustrated in FIG. 30 may be placed as shown. Alternatively, the aperture 3008 may be placed in other configurations, such as between the 45-degree mirror 3010 and the condenser lens 3012, or after the condenser lens 3012.

In a second mode of the illumination assembly 3000, the first light source 3002 does not generate light. Instead, the second light source 3009 generates light that reaches the sample 520 without traversing the at least one opening 3102 in the aperture 3008, such that light generated by the second light source 3009 is not blocked by the aperture 3008. As described, in the second mode of the illumination assembly 3000, the illumination assembly 3000 performs brightfield imaging.

Figure 31:
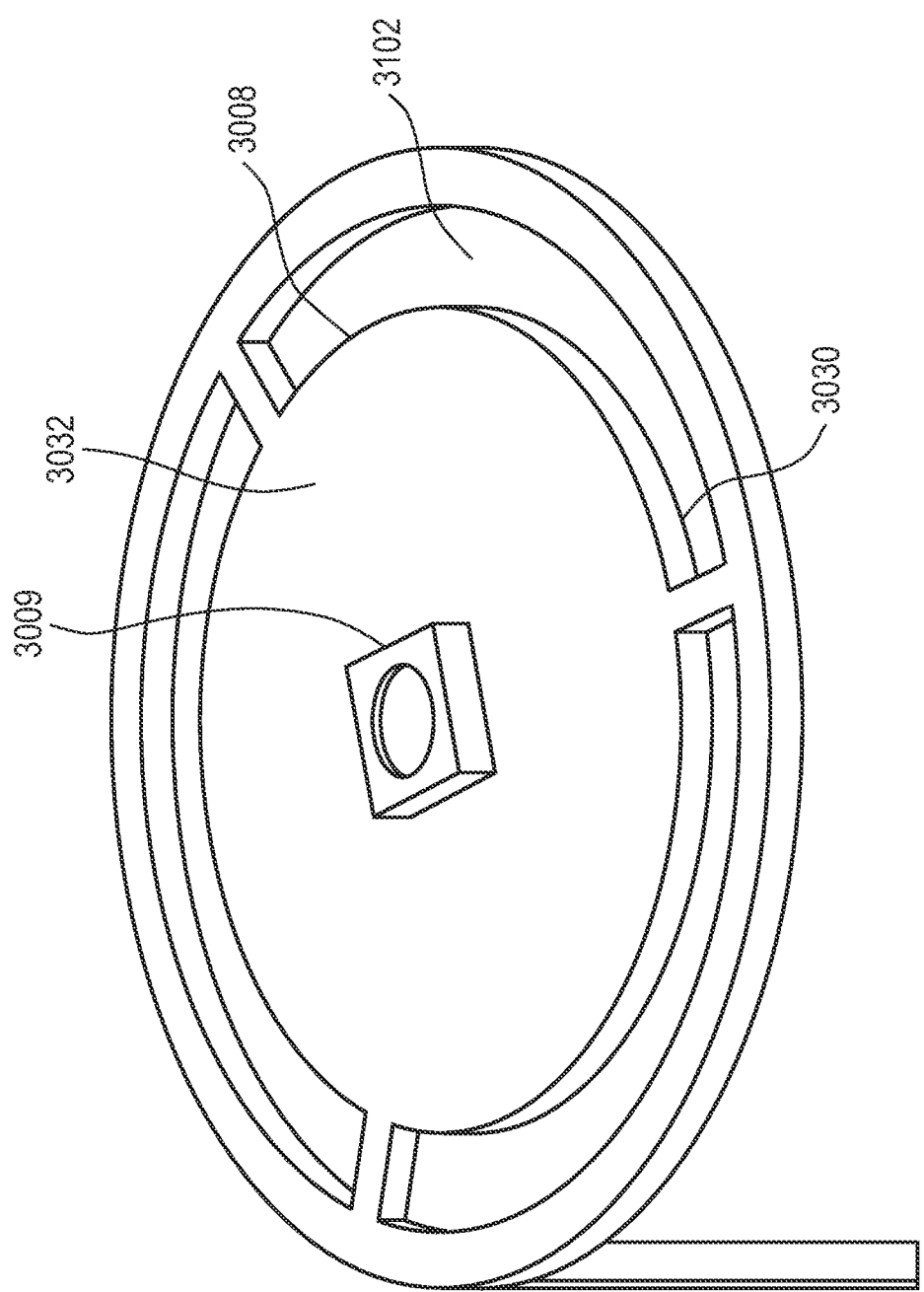
FIG. 31 illustrates a schematic view of the aperture and the attached light source of FIG. 30, according to one embodiment of the invention.

FIG. 31 illustrates a schematic view of the aperture 3008 and the attached light source 3009 of FIG. 30, according to one embodiment of the invention. In one embodiment, the light source may be mounted on the second surface 3032 of the aperture 3008. The light source 3009 and the aperture 3008 may also be built into an integrated aperture and light source. The first surface 3030 of the aperture 3008 may be black to increase light absorption. In one embodiment, the aperture 3008 may be formed from a printed circuit board (PCB).

In one embodiment, the illumination assembly 3000 is configured in the first mode to perform time-lapse darkfield imaging of at least one of a human embryo, an oocyte, or a pluripotent cell. After completion of the time-lapse darkfield imaging, the illumination assembly can be configured in the second mode to perform brightfield imaging of the at least one of a human embryo, an oocyte, or a pluripotent cell. The brightfield imaging may be for intermittent image capture to enable morphological observation. For example, the illumination assembly 3000 may be configured in the first mode for at least two days (and possibly a third day), and then may be configured in the second mode sometime during the third day. In this way, darkfield imaging can be performed (in the first mode) of a human embryo for at least the first two days after fertilization to minimize exposure of the embryo to light. A single brightfield image may be captured (in the second mode) sometime on the third day after fertilization. This brightfield image can facilitate morphology-based grading of the human embryo by an embryologist. By including the aperture 3008 and the attached light source 3009 and controlling the light sources 3002 and 3009 in the first mode and the second mode, the illumination assembly 3000 supports both darkfield imaging and brightfield imaging in the same hardware assembly, without any mechanical moving parts. In addition, the brightfield image for grading by the embryologist can be obtained by the illumination assembly 3000 without moving a dish containing the embryo. This is advantageous because the embryo may be sensitive to disturbances such as movement.

In one embodiment, the illumination assembly 3000 alternates between being configured in the first mode and in the second mode at least once per hour. For example, the illumination assembly can take a darkfield image in the first mode, followed by a brightfield image in the second mode. This can be repeated periodically, such as every 5 minutes, to obtain time-lapse movies of a human embryo in both darkfield and brightfield modalities.

Figure 6:
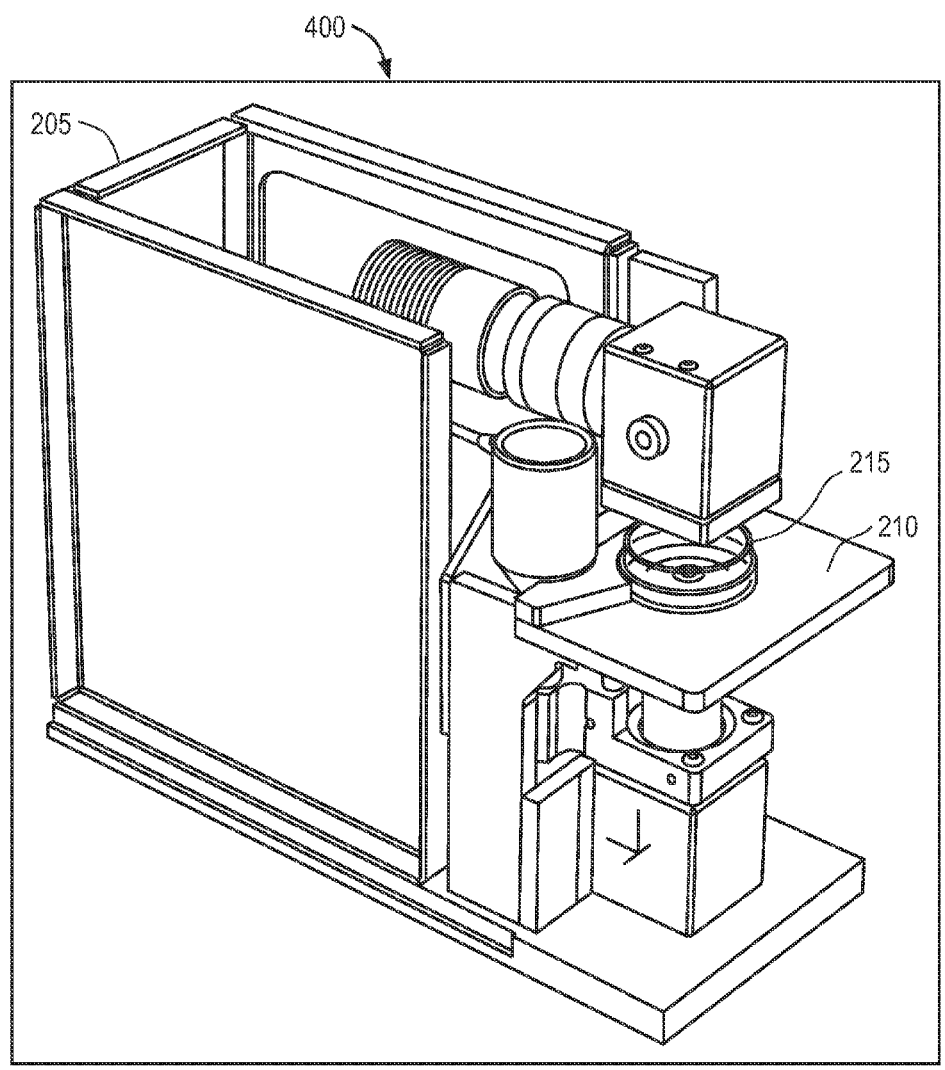
FIG. 6 illustrates a schematic view of the microscope in FIG. 4 mounted inside the housing of the imaging system of FIG. 2, according to an embodiment of the invention.

FIG. 6 illustrates a schematic view of the microscope 400 of FIG. 4 mounted inside the housing 205 of the imaging system 200 of FIG. 2, according to an embodiment of the invention. The illumination and imaging sub-assemblies 405-410 are mounted to an aluminum (or other material) chassis (i.e., part of housing 205) that holds everything together. The chassis also mounts the loading platform 210 for the dish 215.

Figure 7:
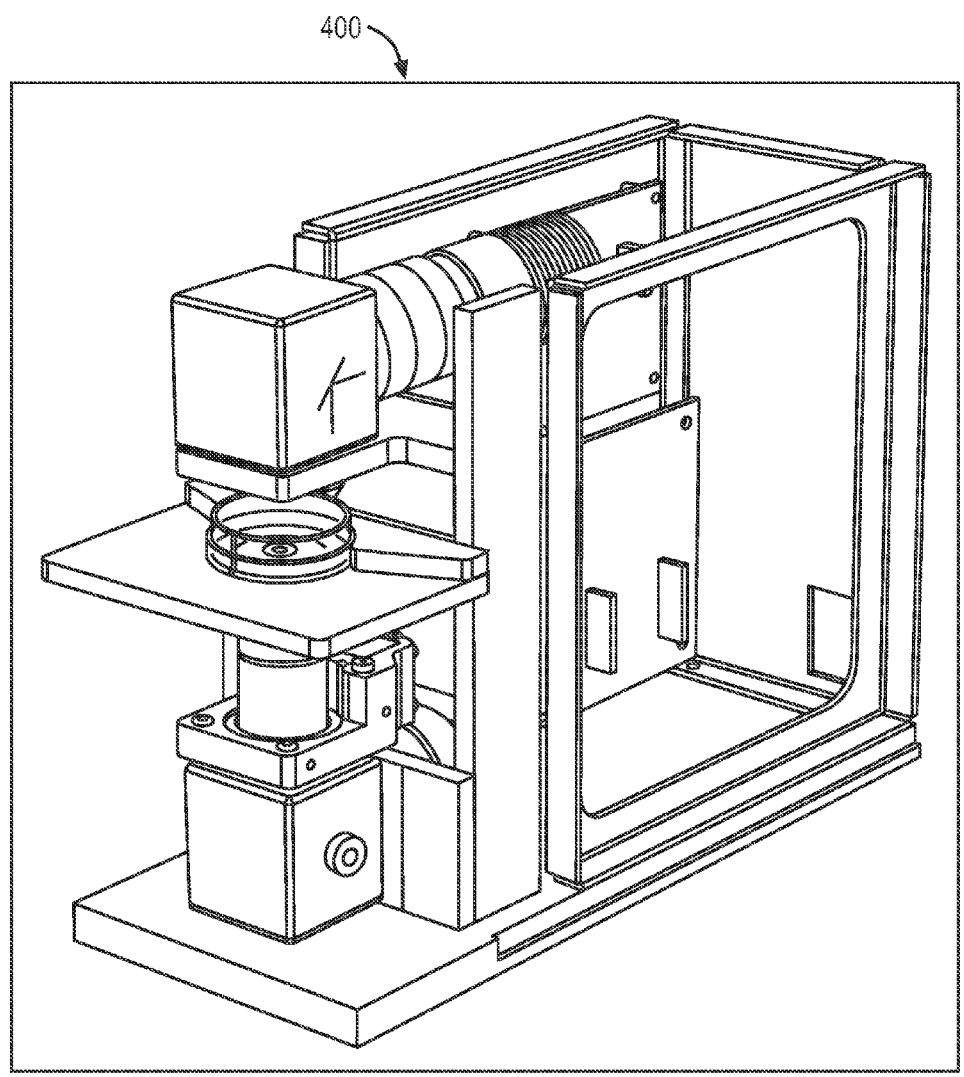
FIG. 7 illustrates a schematic view of the microscope in FIG. 4 mounted inside the housing of the imaging system of FIG. 2, according to an embodiment of the invention.

Another schematic view of the microscope inside the housing 205 is shown in FIG. 7, according to an embodiment of the invention. In this embodiment, at the back end of the microscope are the on-board electronics for controlling the motor, camera, LED, LCD display, and any other parts such as indicator LEDs. Alternatively, as described with reference to FIG. 32, all or part of the on-board electronics for controlling the motor, camera, LED, LCD display, and any other parts such as indicator LEDs may be included in a controller outside of the housing 205.

Figure 8:
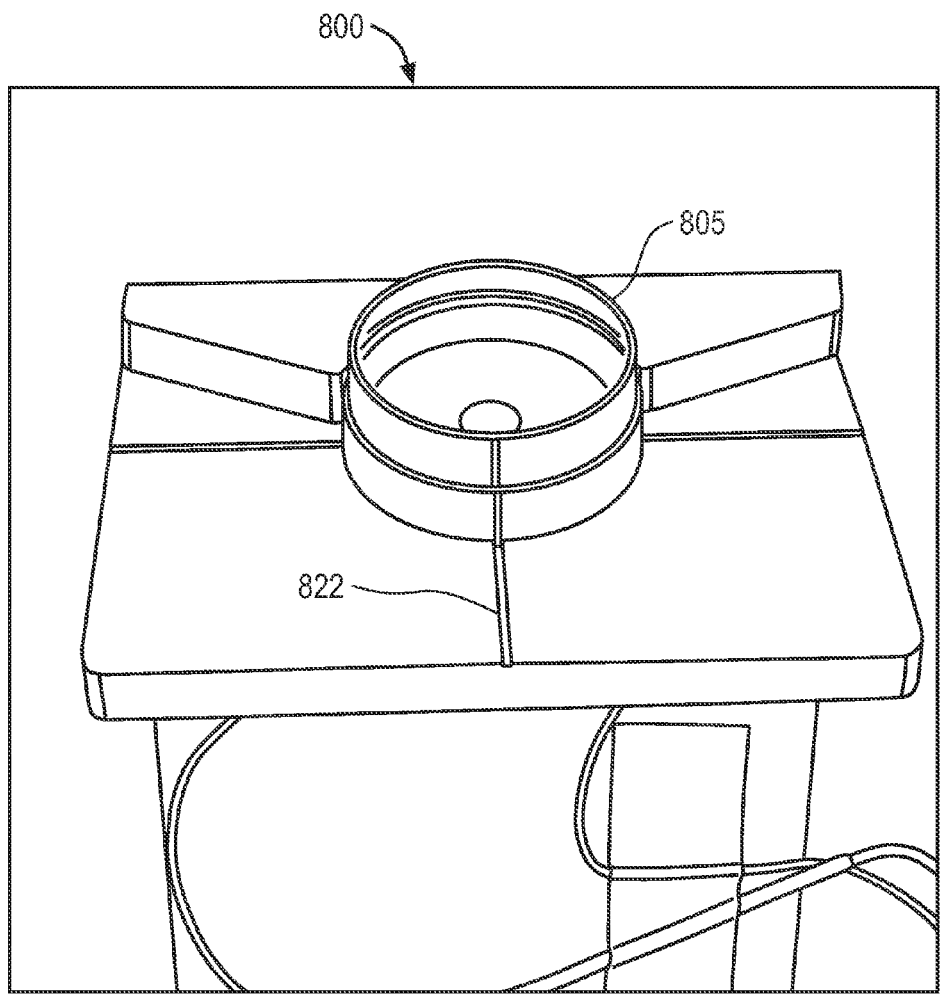
FIG. 8 illustrates a schematic diagram of a loading platform in the imaging system of FIG. 2, according to an embodiment of the invention.

Referring now to FIG. 8, a schematic diagram of a loading platform included in the imaging system 200 of FIG. 2 is described, according to an embodiment of the invention. The loading platform 800 may have several associated features to help identify if the dish 805 is located and oriented properly, such as, for example:
  1. A back-plate to help position the dish 805;
  2. A recessed groove (less than a millimeter deep) that the dish 805 seats into;
  3. A keying (mechanical) feature on the dish 805 that only allows loading with one possible orientation;
  4. Markers (such as cross-hairs) to help with orientation. The user can rotate the dish 805 to align the vertical bar on the dish 805 with the central line;
  5. An indicator LED to help illuminate the vertical bar or other feature on the dish 805;
  6. Fiducials on the dish, such as letters, numbers, dots, or lines that can be identified using the microscope and software;
  7. Software that uses the microscope to capture images of the dish 805 and monitor the loading procedure. An indicator LED could change colors to alert the user when the dish 805 is oriented correctly or incorrectly; and/or 8. Software that can account for misalignments (and potentially allow loading with an arbitrary orientation) and adjust the image accordingly.

It is appreciated that other mechanical and electronic components may be included in loading platform 800 for securing dish 805 into place.

Figure 9A:
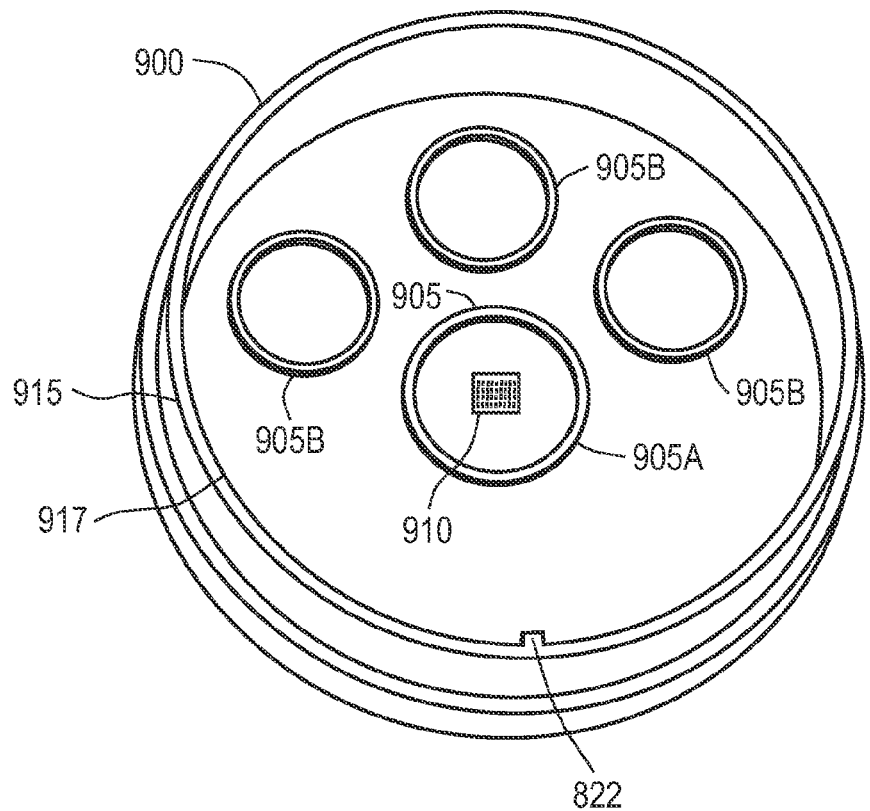
FIGS. 9A-B illustrate a schematic diagram of a multi-well culture dish, according to an embodiment of the invention.
Figure 9B:
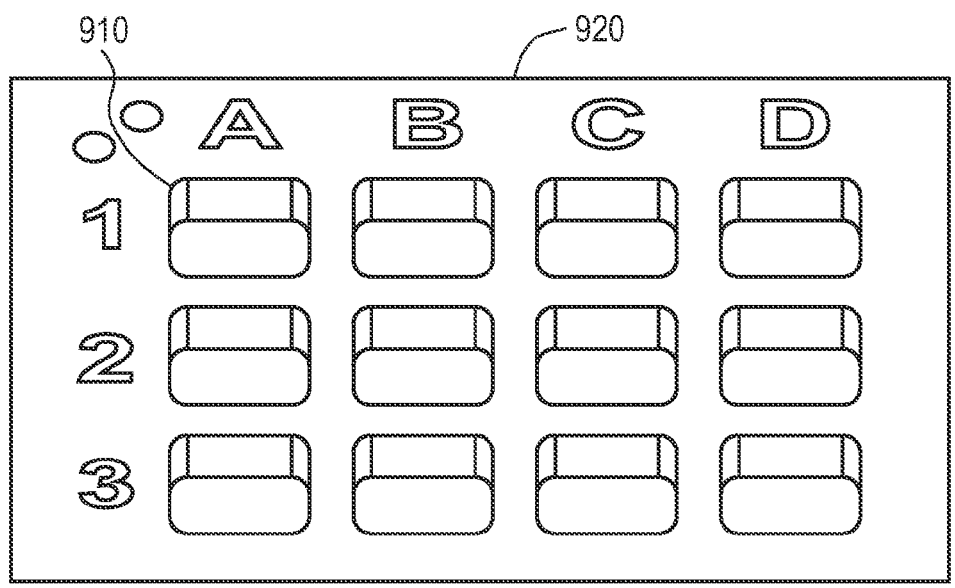
Figure 10:
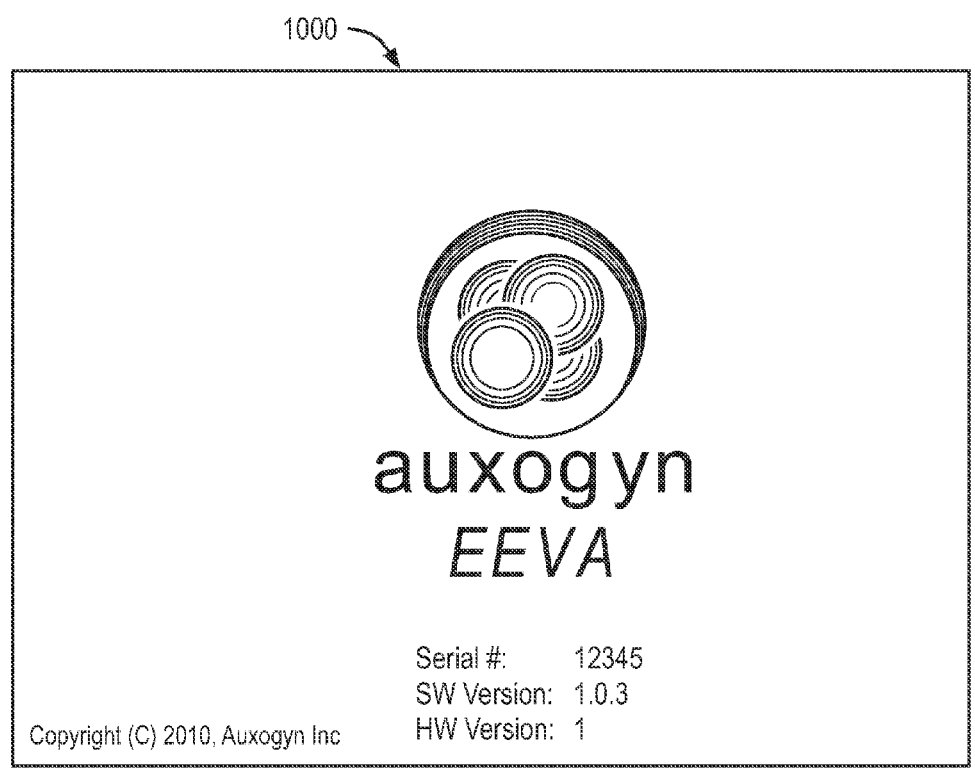
FIGS. 10-17 illustrate various display screens of a GUI for use with the apparatus of FIG. 1, according to an embodiment of the invention.
Figure 11:
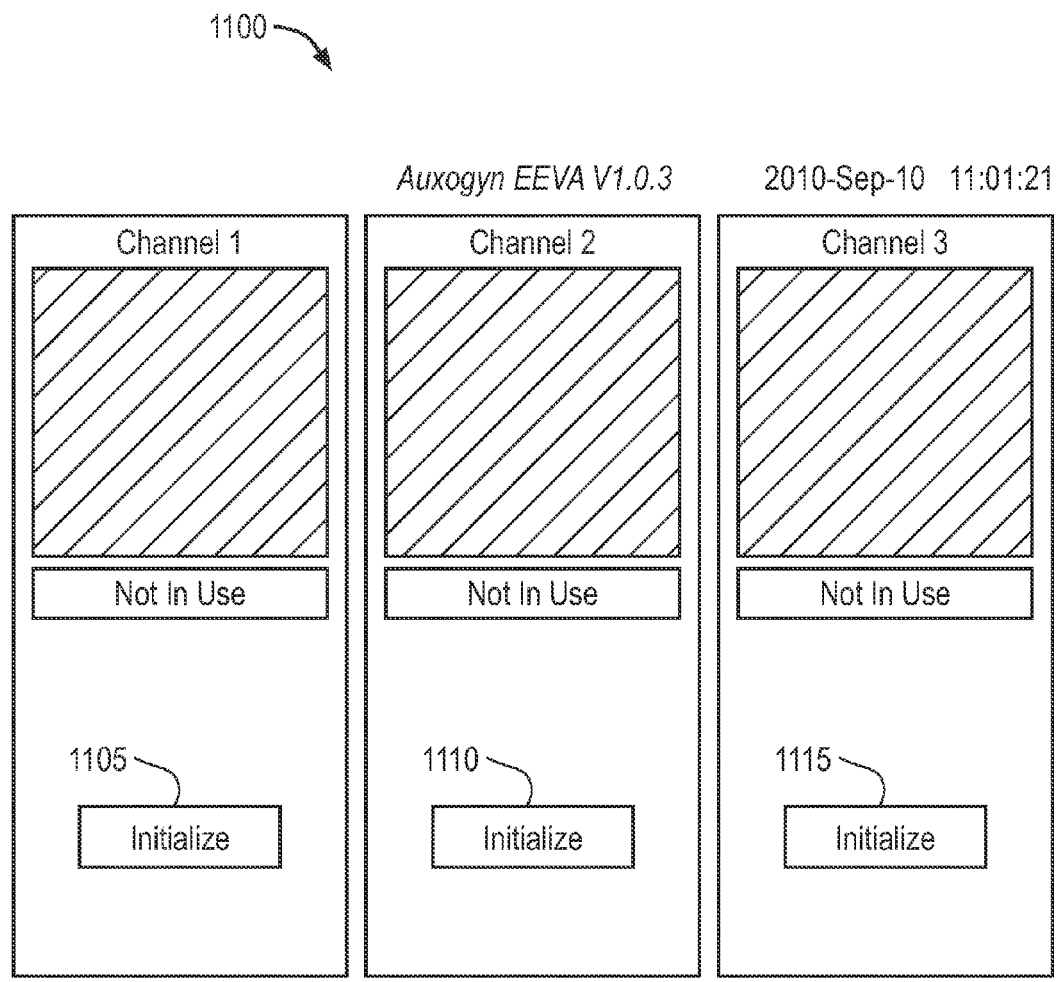
Figure 12:
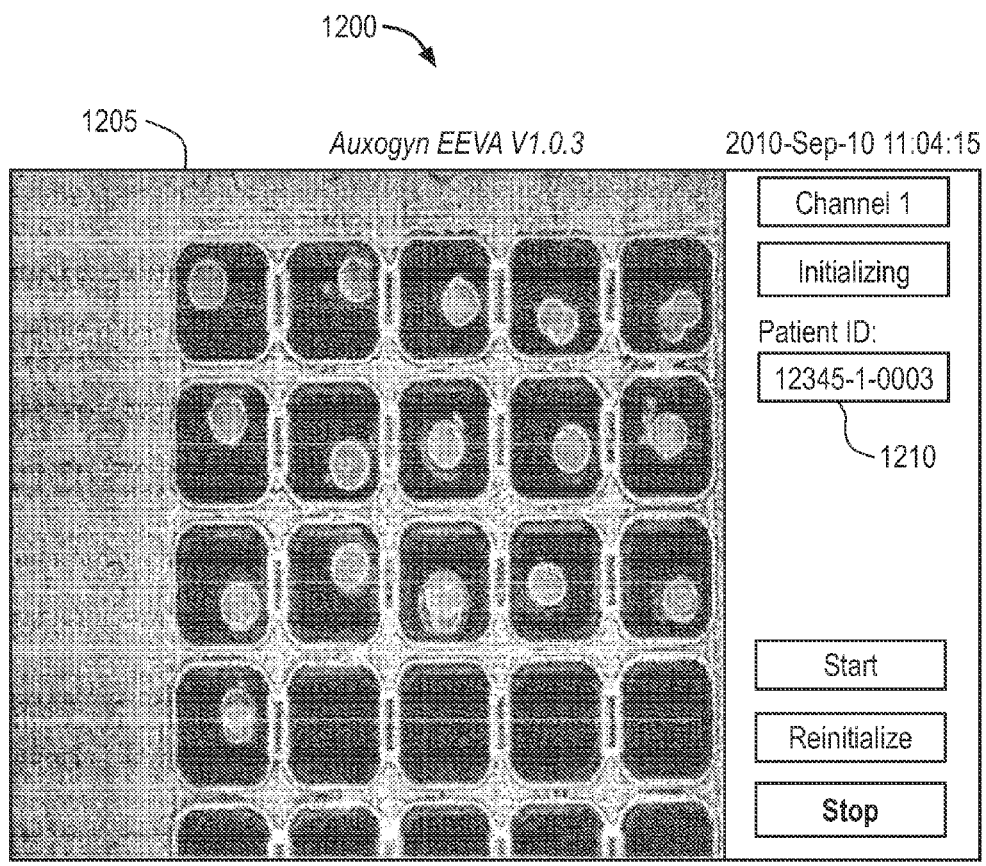
Figure 13:
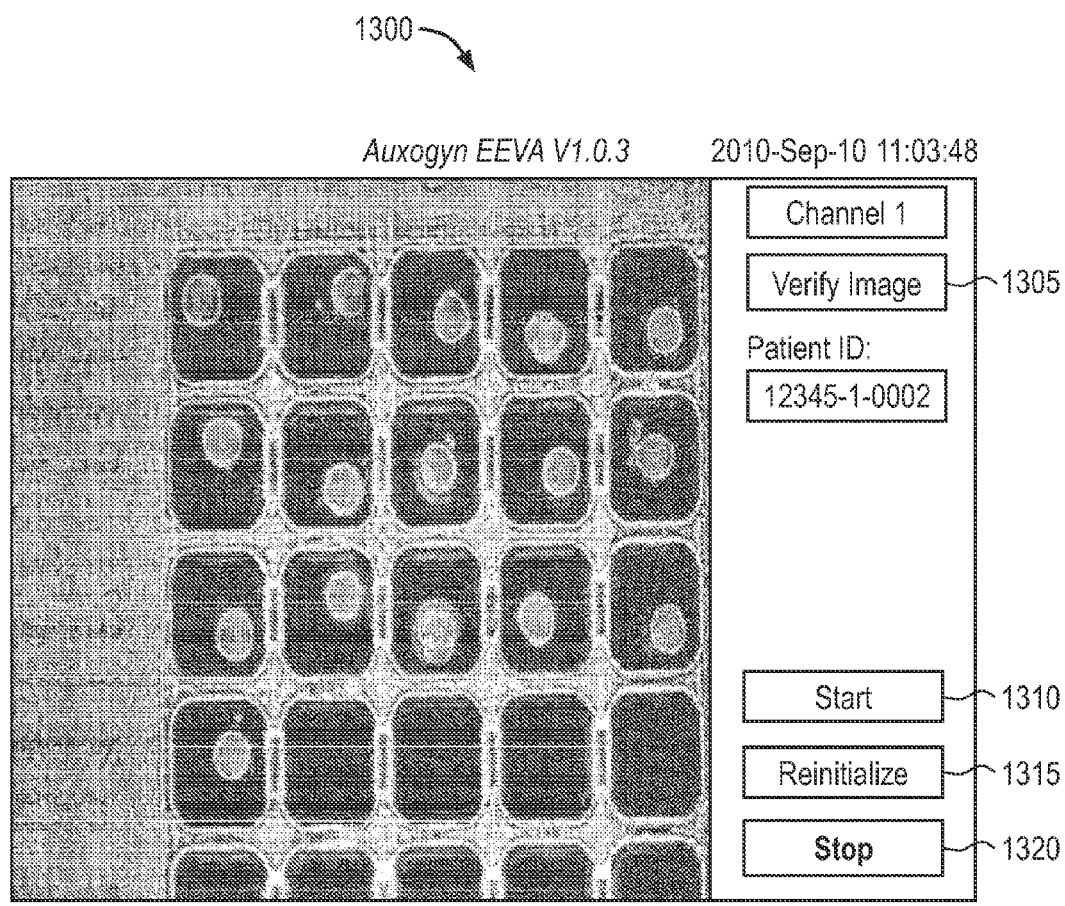

FIGS. 9A-B illustrate a schematic diagram of a multi-well culture dish 900, according to an embodiment of the invention. The dish 900 may be used with the imaging apparatus 200 of FIG. 2 or other types of devices for imaging of embryos, oocytes, or pluripotent cells. The dish 900 may include multiple rings 905. In one embodiment, the rings 905 may be substantially circular. Alternatively, the rings 905 may be oblong. One of the rings 905A may substantially circumscribe one or more wells 910. The ring 905A may be substantially centrally disposed in the dish 900. The wells 910 may be micro-wells. In one embodiment, each micro-well 910 can hold a single embryo, oocyte, or pluripotent cell, and the bottom surface of each micro-well 910 can have an optical quality finish such that a group of embryos within a single group of micro-wells can be imaged simultaneously by a single miniature microscope with sufficient resolution to follow cellular events. Each micro-well 910 may also be designed with a depth to facilitate its use. In one embodiment, the dish 900 may include one or more rings 905B. The rings 905B may be laterally offset from the ring 905A, and may be used to hold media drops for rinsing.

Referring to FIG. 9A, in one embodiment, an outer ring 915 may be positioned around the rings 905. The marker 822 (described with reference to FIG. 8) may be disposed adjacent to a lateral surface 917 of the outer ring 915.

Referring to FIG. 9B, in one embodiment, the micro-wells 910 may be disposed in a grid 920, such as a rectangular grid or a square grid. For example, the grid 920 may be 3×4 (as shown in FIG. 9B), 3×3, or 4×5. However, the dimensions of the grid are not limited to these examples.

Figure 26:
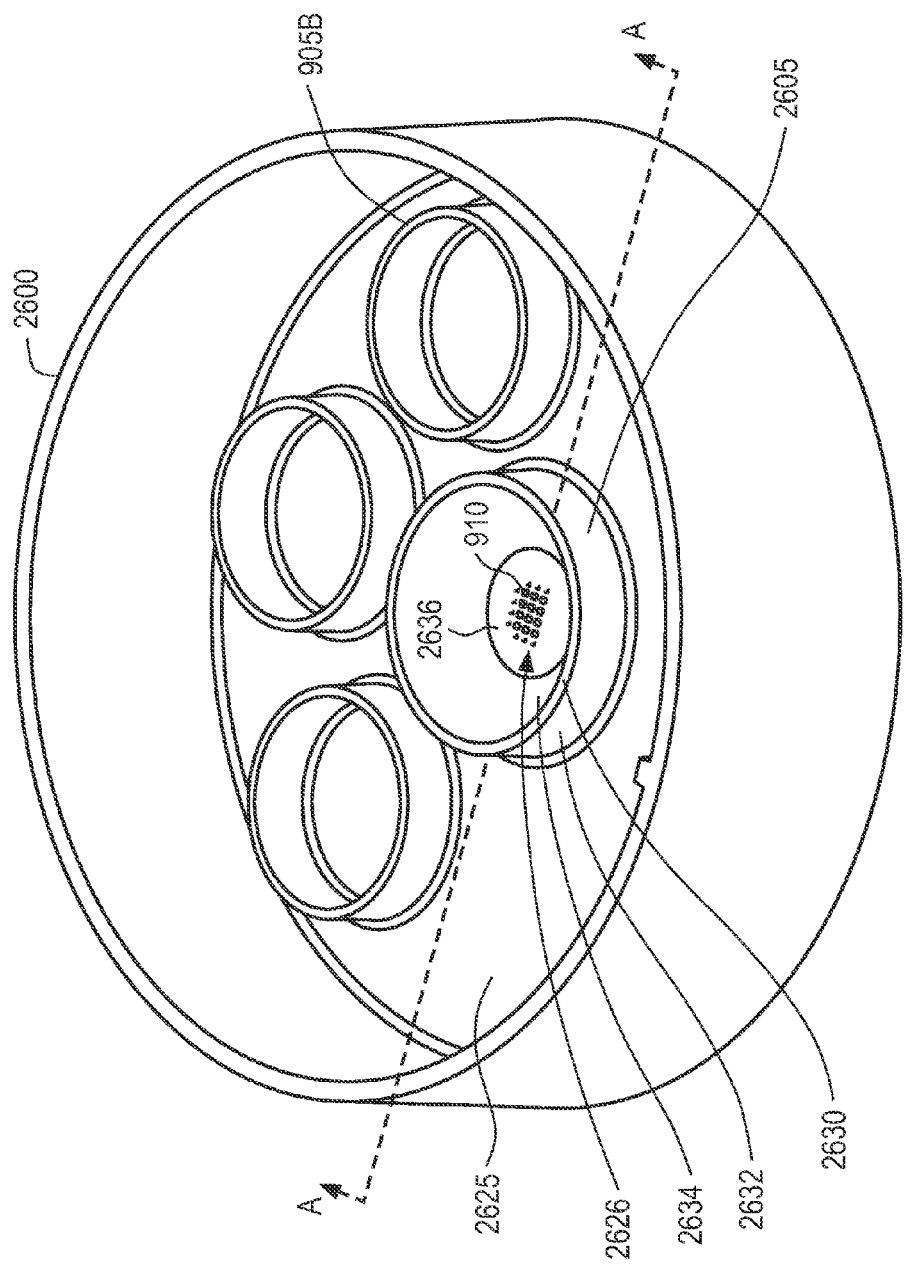
FIG. 26 illustrates a schematic diagram of a multi-well culture dish, according to an embodiment of the invention.

FIG. 26 illustrates a schematic diagram of a multi-well culture dish 2600, according to an embodiment of the invention. The dish 2600 may be used with the imaging apparatus 200 of FIG. 2, or other types of devices for imaging of embryos, oocytes, or pluripotent cells. The dish 2600 may include a ring 2605 that may be substantially centrally disposed in the dish 2600. In one embodiment, the ring 2605 may be substantially circular. Alternatively, the ring 2605 may be oblong. The ring 2605 may substantially circumscribe one or more wells 910 (described with reference to FIGS. 9A and 9B). The dish 2600 may also include one or more rings 905B (described with reference to FIGS. 9A and 9B).

Figure 27:
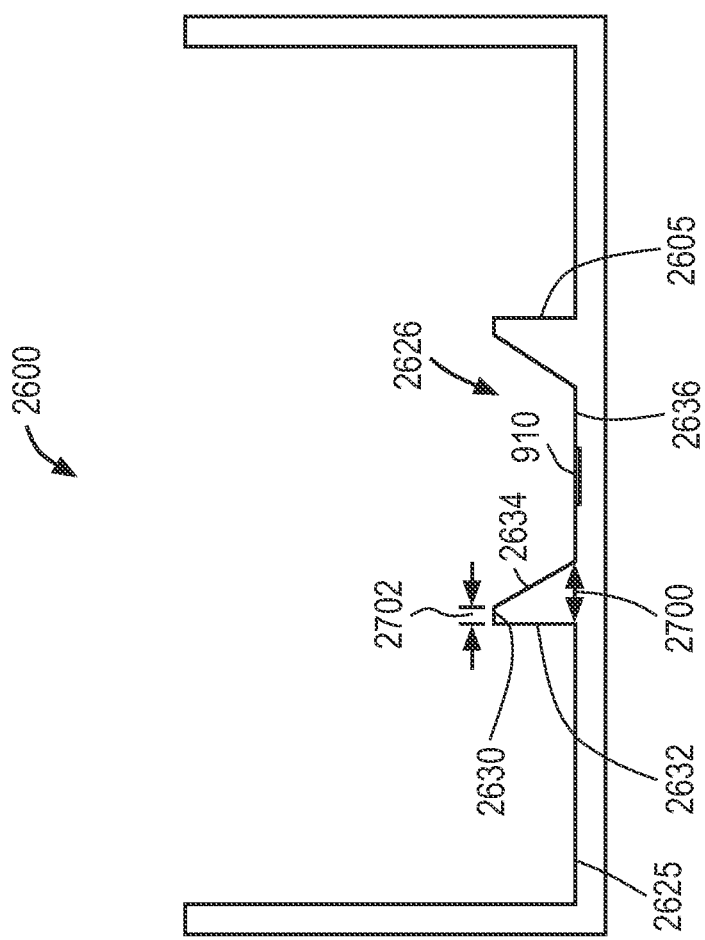
FIG. 27 illustrates a cross-section view of the multi-well culture dish along cross-section A-A in FIG. 26, according to an embodiment of the invention.

FIG. 27 illustrates a cross-section view of the multi-well culture dish 2600 along cross-section A-A in FIG. 26, according to an embodiment of the invention. Referring to FIGS. 26 and 27, the ring 2605 is disposed on a lower surface 2625 of the dish 2600. The ring 2605 defines a cavity 2626, and has an upper surface 2630, an outer lateral surface 2632, and an inner lateral surface 2634. The cavity 2626 has a cavity bottom 2636, and the micro-wells 910 are defined by the cavity bottom 2636. The inner lateral surface 2634 of the ring 2605 is disposed between the outer lateral surface 2632 and the micro-wells 910, and extends from the upper surface 2630 of the ring 2605 to the cavity bottom 2636.

In one embodiment, the inner lateral surface 2634 slopes toward the micro-wells 910 such that a first width 2700 of the ring 2605 at the lower surface 2625 of the dish 2600 is greater than a second width 2702 of the ring 2605 at the upper surface 2630 of the ring 2605. In one embodiment, the first width 2700 is in the range from about two times to about six times as large as the second width 2702, such as three times, four times, or five times as large. Alternatively, the inner lateral surface 2634 may be substantially vertical, such that the first width 2700 is approximately equal to the second width 2702.

Movement of a media drop stored in the ring 2605 may be caused by movement of the dish 2600, such as due to transport or other handling of the dish 2600. Advantageously, this movement of the media drop can be reduced by the sloping of the inner lateral surface 2634 toward to micro-wells 910, which positions the inner lateral surface 2634 closer to the micro-wells 910. This reduces the area in which a media drop stored in the ring 2605 can move, and provides a larger contact surface area between the inner lateral surface 2634 and the media drop to enhance stability of the media drop. As a result, fluid flow resulting from motion of the media drop can be reduced, which can reduce the likelihood of embryos or pluripotent cells being pulled out of the micro-wells 910 due to motion of the media drop.

Figure 28:
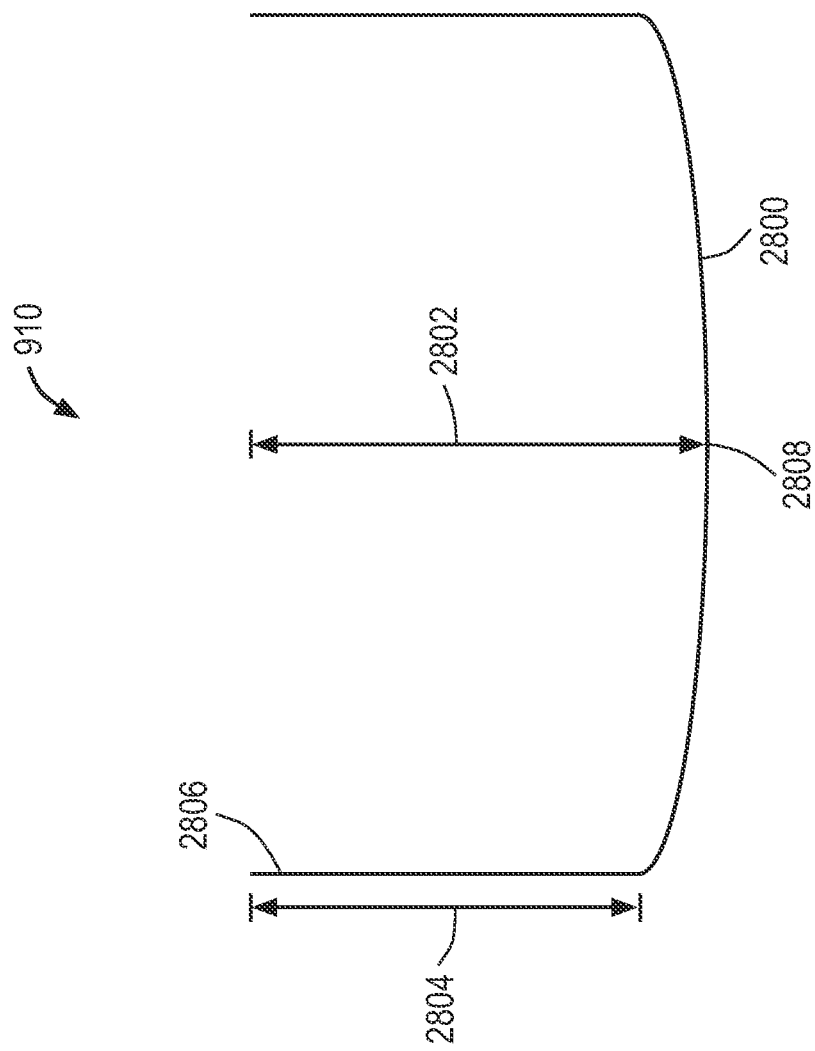
FIG. 28 illustrates a cross-section view of a micro-well, according to an embodiment of the invention.

FIG. 28 illustrates a cross-section view of the micro-well 910, according to an embodiment of the invention. In one embodiment, a lower surface 2800 of the micro-well 910 may be curved. For example, a first depth 2802 at a center 2808 of the micro-well 910 may be in the range from about 1.1 to about 1.5 times as large as a second depth 2804 at a lateral periphery 2806 of the micro-well 910, such as about 1.2 times, about 1.3 times, or about 1.4 times. Alternatively, the lower surface 2800 of the micro-well 910 may be substantially planar, such that the first depth 2802 is substantially equal to the second depth 2804.

Figure 29:
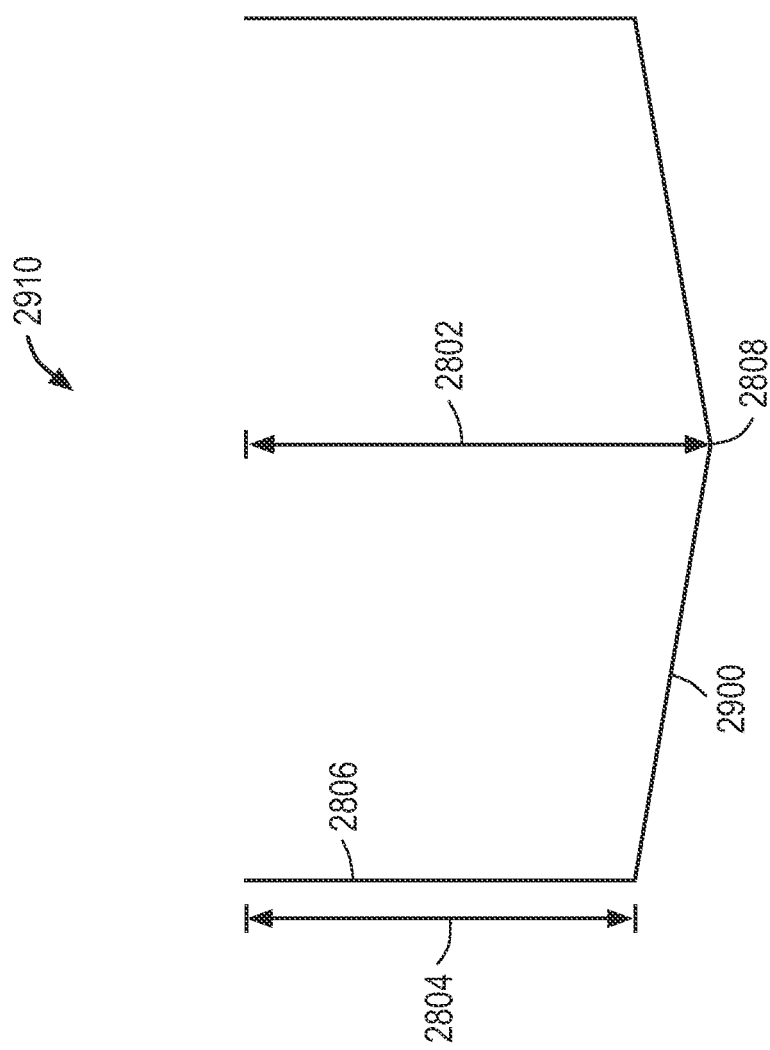
FIG. 29 illustrates a cross-section view of a micro-well, according to an embodiment of the invention.

FIG. 29 illustrates a cross-section view of a micro-well 2910, according to an embodiment of the invention. The micro-well 2910 is in many respects similar to the micro-well 910 described with reference to FIGS. 9 and 28, so differences are described here. A lower surface 2900 of the micro-well 2910 may be conical. For example, the lower surface 2900 may slope downwardly, and substantially linearly, from the lateral periphery 2806 to the center 2808 of the micro-well 2910. As described with reference to FIG. 28, the first depth 2802 may be in the range from about 1.1 to about 1.5 times as large as the second depth 2804, such as about 1.2 times, about 1.3 times, or about 1.4 times.

Referring now to FIGS. 10-17, the GUI is now described, according to an embodiment of the invention. GUI screen 1000 (FIG. 10) shows an exemplary start-up screen showing information pertaining to the software in the imaging system. GUI screen 1100 (FIG. 11) shows an initialization screen illustrating that multiple channels or microscopes (in this example there are 3) can be controlled from a single touch-screen panel, and multiple touch-screen panels can be controlled from a single computer. The touch-screens may be proximal to the incubator or may be located remotely.

It is appreciated that each channel is included within an imaging system, e.g., imaging system 200, placed inside an incubator. As described above, it is appreciated that imaging system 200 may include multiple channels. The GUI displayed on a touch screen panel interacts with the software controlling each channel. It is further appreciated that a user may configure several items of GUI screen 1100, such as the assignment of which microscope is displayed on which panel, the number of microscopes displayed on each panel, and the number of panels.

To start using a microscope, the user first presses one of the Initialize buttons 1105-1115 and then loads the dish onto the loading platform of the selected microscope. The initialize button can have various labels such as "auto-focus." As described above, each microscope may have multiple alignment cues, including a light that illuminates a feature on the dish when the dish is in proper alignment. The software associated with the microscope may also use the camera in the microscope to detect whether the dish is aligned, and illuminates an indicator when the dish is in proper position. The display 1205 (FIG. 12) may show the camera image as a further aid to alignment. The light illuminating the dish may serve either or both purposes (i.e., alignment aid, indicator) and change color when the dish is properly aligned, or there may be separate lights.

During initialization, the software performs auto-exposure, auto-focus, and verifies orientation of the dish (and whether a dish is even installed). When correctly placed, a set of wells is displayed on the touch-screen, and a user may confirm correct placement.

Before, during or after alignment (not shown), the user enters patient/subject identification information (ID, name, etc) in window 1210 using the touch screen panel and virtual keyboard. The identifying information is then shown on a display that is on or part of the microscope, such as, for example, LCD 220 of imaging system 200 shown in FIG. 2. Alternatively, the touch-screen display may use color and/or text to correlate each set of touch-screen controls with a corresponding microscope that would be marked with the corresponding color and/or text. Alternatively, the patient/subject information can be automatically entered through a scanning device such as a barcode scanner.

After the software recognizes that a dish is properly loaded, the user is asked to verify (1305, FIG. 13) that the image is correct. The user may choose to start the imaging process (1310), re-initialize (1315), i.e., re-do the exposure, focus and orientation check, or stop (go back to the "not in use" state) (1320).

Figure 15:
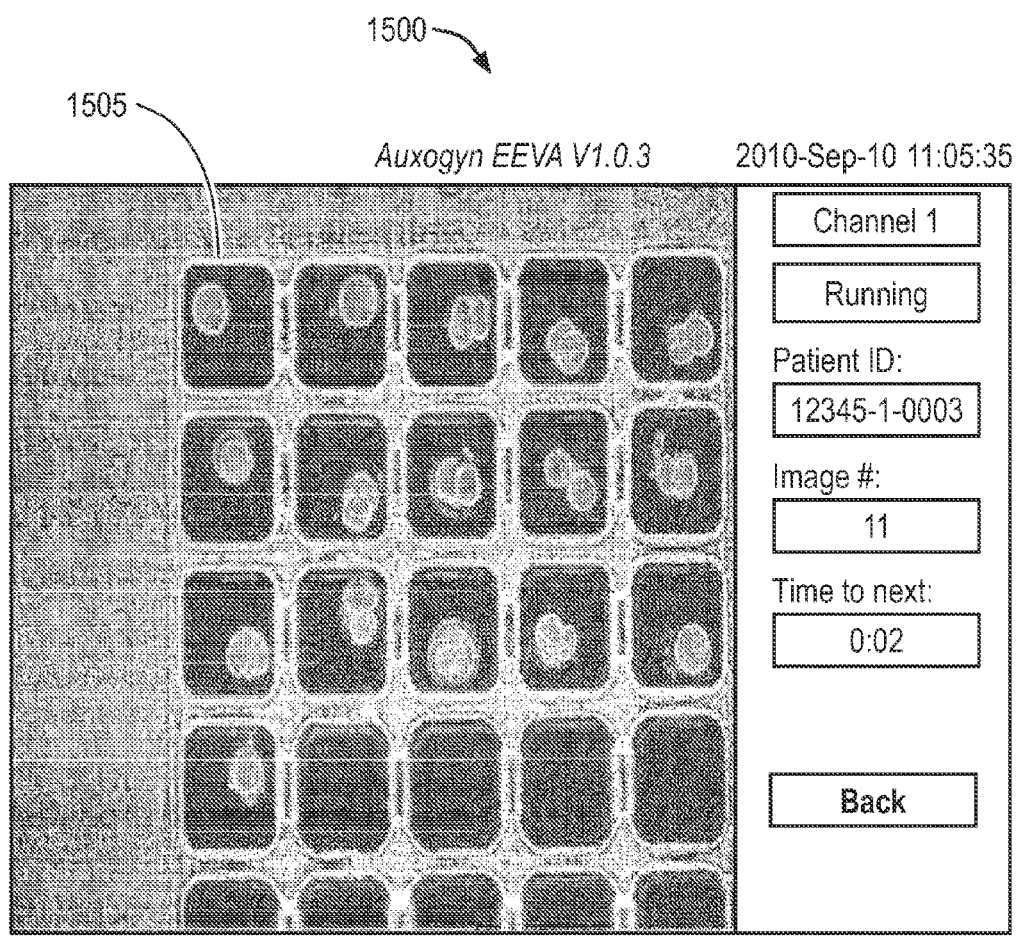

It is appreciated that display 1300 may show which wells are occupied, by displaying a border or other marking around each occupied well (see FIG. 15). It is also appreciated that if display screen 1300 is reached after resuming from a Paused state, then in addition to marking each occupied well, wells may also be marked to indicate whether they were previously occupied and now are not, or vice versa. The user will then be asked to acknowledge these differences before proceeding, or, alternatively, the user can remove the dish and re-initialize (go through the verification process again) to resolve any discrepancies.

Figure 14:
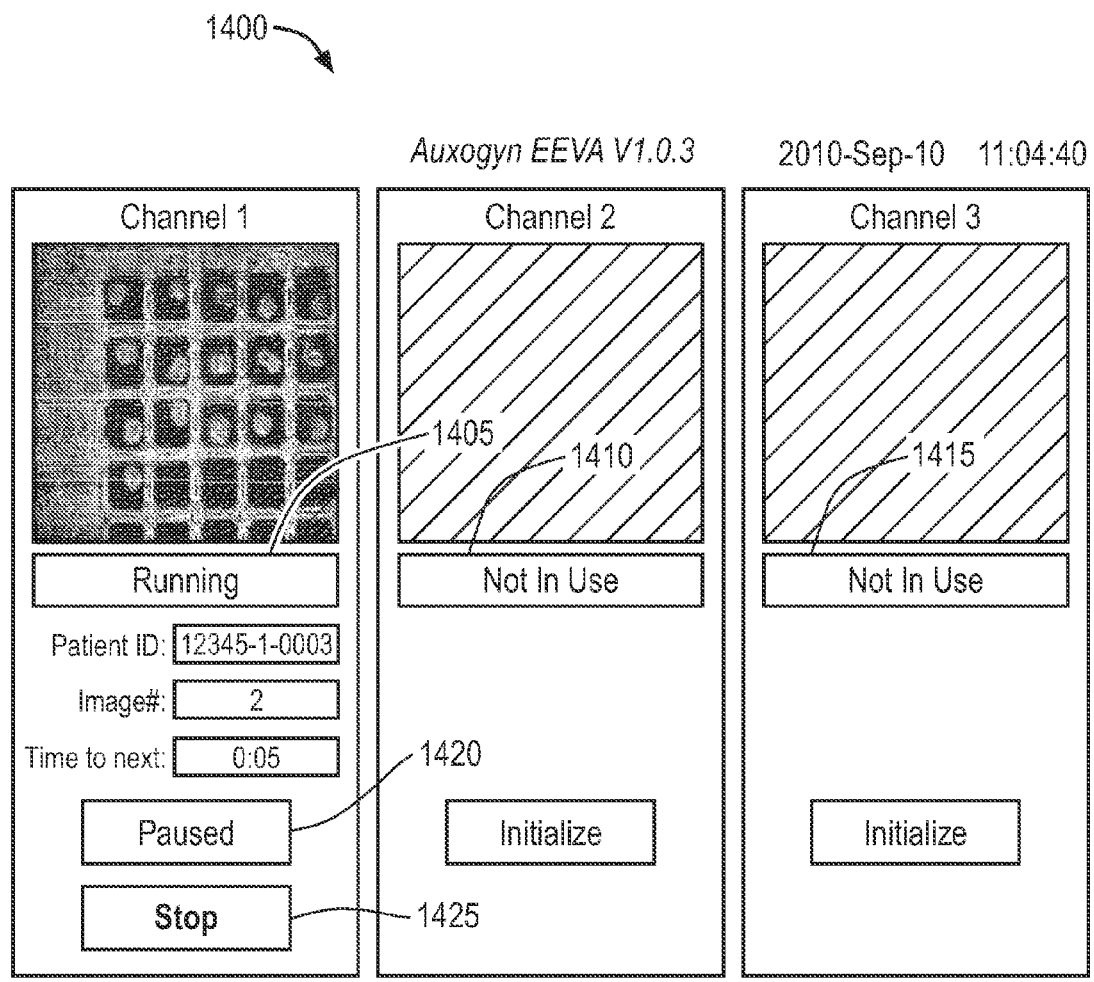

The touch-screen panel may then display the status of each channel, and the patient information (ID, name, etc) at display screen 1400 (FIG. 14). The status of each channel may be either "running", i.e., in operation, (1405) or "not in use" (1410-15). The user may also touch the image in order to see a closer view of the dish for a specific microscope, pause (1420), or stop image processing (1425).

Figure 16:
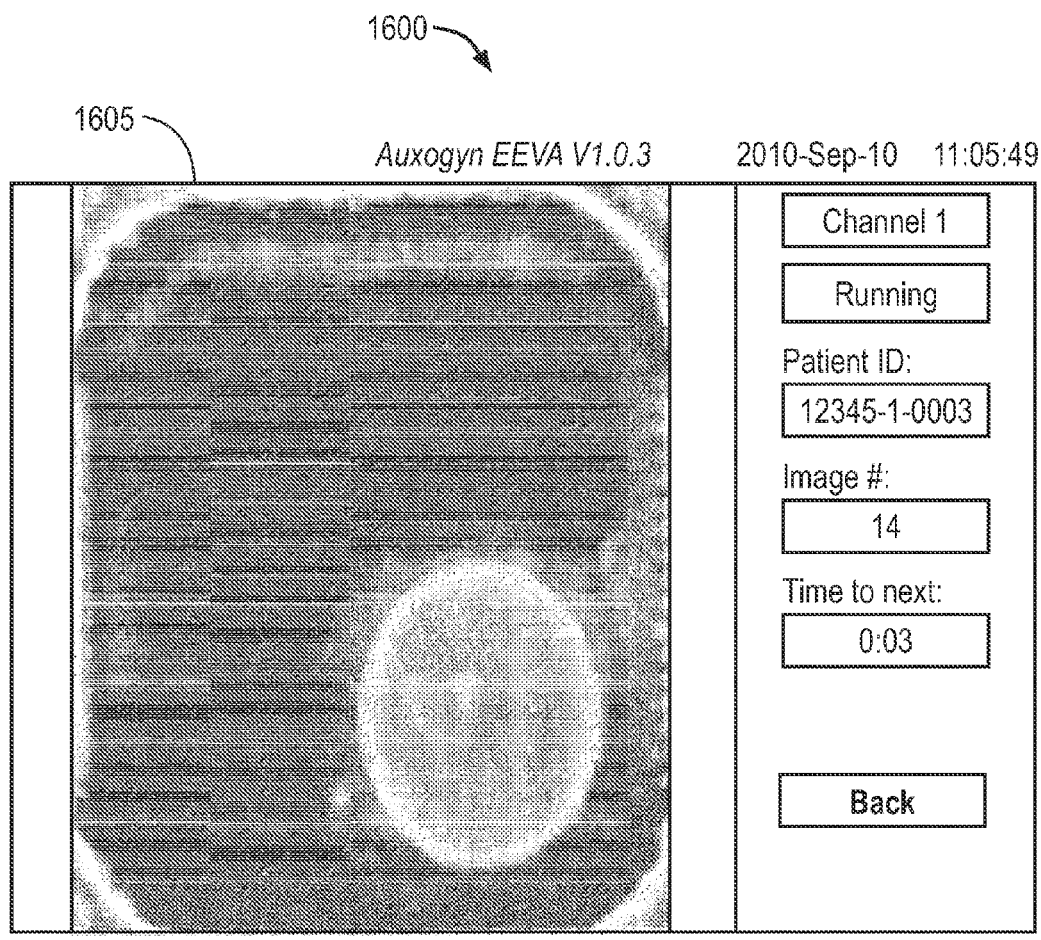

As described above, when a closer view of a specific microscope image is shown, the occupied wells may be marked with an overlay 1505 (FIG. 15). The user may touch the touch screen within each marked cell to see a closer view of the specific well (as shown in FIG. 16).

It is appreciated that a similar display may be shown when resuming (after pause) to indicate whether the same wells are occupied as previously (since the dish could have been removed when paused). The user may then be asked to acknowledge that any occupancy differences are acceptable before image processing can continue.

Display screen 1600 (FIG. 16) shows a closer view of a single well 1605. A well identifier (position in the multi-well, such as, for example, "A1", "B4", etc) may also be displayed with this image.

Figure 17:
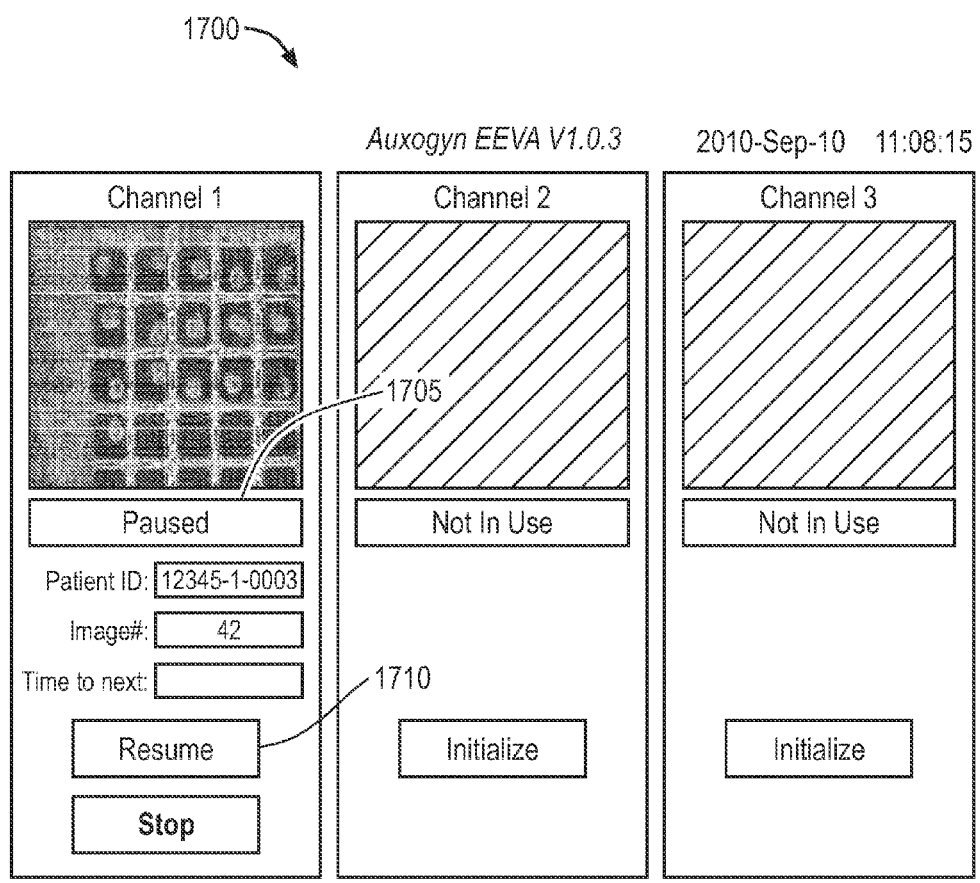

Other GUI features are shown in FIG. 17. For example, when paused (1705), the user may remove and replace the dish in the incubator. When the user selects to resume (1710), the initialization process is performed again, to determine/verify exposure, focus and dish orientation. An additional verification is performed to determine whether the same dish wells are occupied as previously. If there are differences, the user may be asked to acknowledge the differences before processing can resume. For example, the act of selecting a channel/microscope through the touch screen can alternatively be performed by pressing a foot-switch to allow hands-free operation while carrying a petri dish, or alternatively a remote control.

Figure 18:
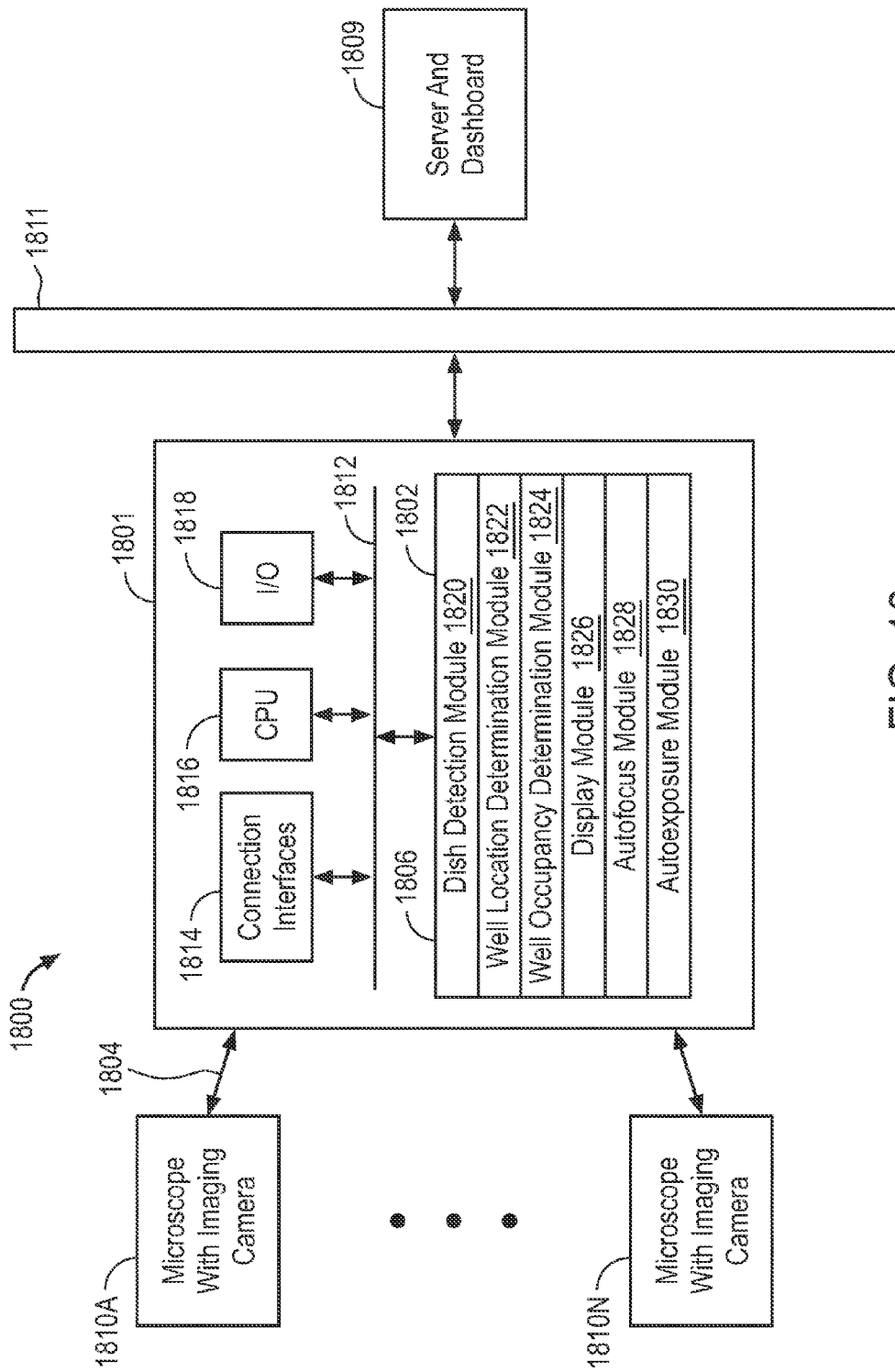
FIG. 18 illustrates a system for automated imaging of human embryos, oocytes, or pluripotent cells including an apparatus for automated dish detection and well occupancy determination, according to an embodiment of the invention.

FIG. 18 illustrates a system 1800 for automated imaging of human embryos, oocytes, or pluripotent cells including an apparatus 1802 for automated dish detection and well occupancy determination, according to an embodiment of the invention. The automated detection of the multi-well culture dish and the determination of well occupancy are processing performed prior to the automated imaging of human embryos. For the subsequent description with reference to FIGS. 18 to 25, the multi-well culture dish is referred to as the multi-well culture dish 900 as described with reference to FIG. 9A, though it is contemplated that the multi-well culture dish can also correspond to the multi-well culture dish 2600 as described with reference to FIG. 26, or to any similar multi-well dish where detection of the dish and determination of occupancy of wells included in the dish can be performed in a similar manner.

The system 1800 includes a microscope controller 1801, which may communicate via a transmission channel 1804 with a set of microscopes with imaging cameras 1810A-1810N. The microscope controller 1801 may be connected to each microscope with imaging camera 1810 via a point-to-point connection, or may be connected to multiple microscopes with imaging cameras 1810 via a network. In one embodiment, the microscope controller 1801 includes standard components, such as connection interfaces 1814, a CPU 1816, and an input/output module 1818, which communicate over a bus 1812. In one embodiment, a memory 1806 connected to the bus 1812 stores a set of executable programs that are used to implement the apparatus 1802 for automated detection of a multi-well culture dish and determination of occupancy of a plurality of micro-wells included in the multi-well culture dish. Alternatively, a processing device (such as circuitry, not shown) connected to the bus 1812 can be used to implement the apparatus 1802 for automated detection of a multi-well culture dish and determination of occupancy of a plurality of micro-wells included in the multi-well culture dish. The microscope controller 1801 may be connected to a server 1809 via a transmission channel 1811, which may be a point-to-point connection or a network. The server 1809 may include a dashboard for providing status information and parameters determined based on analysis of images of a human embryo or pluripotent cell generated by the microscopes with imaging camera 1810.

In an embodiment of the invention, the memory 1806 stores executable instructions establishing a dish detection module 1820, a well location determination module 1822, a well occupancy determination module 1824, and a display module 1826. Alternatively, the processing device (not shown) includes the dish detection module 1820, the well location determination module 1822, the well occupancy determination module 1824, and the display module 1826.

Figure 19:
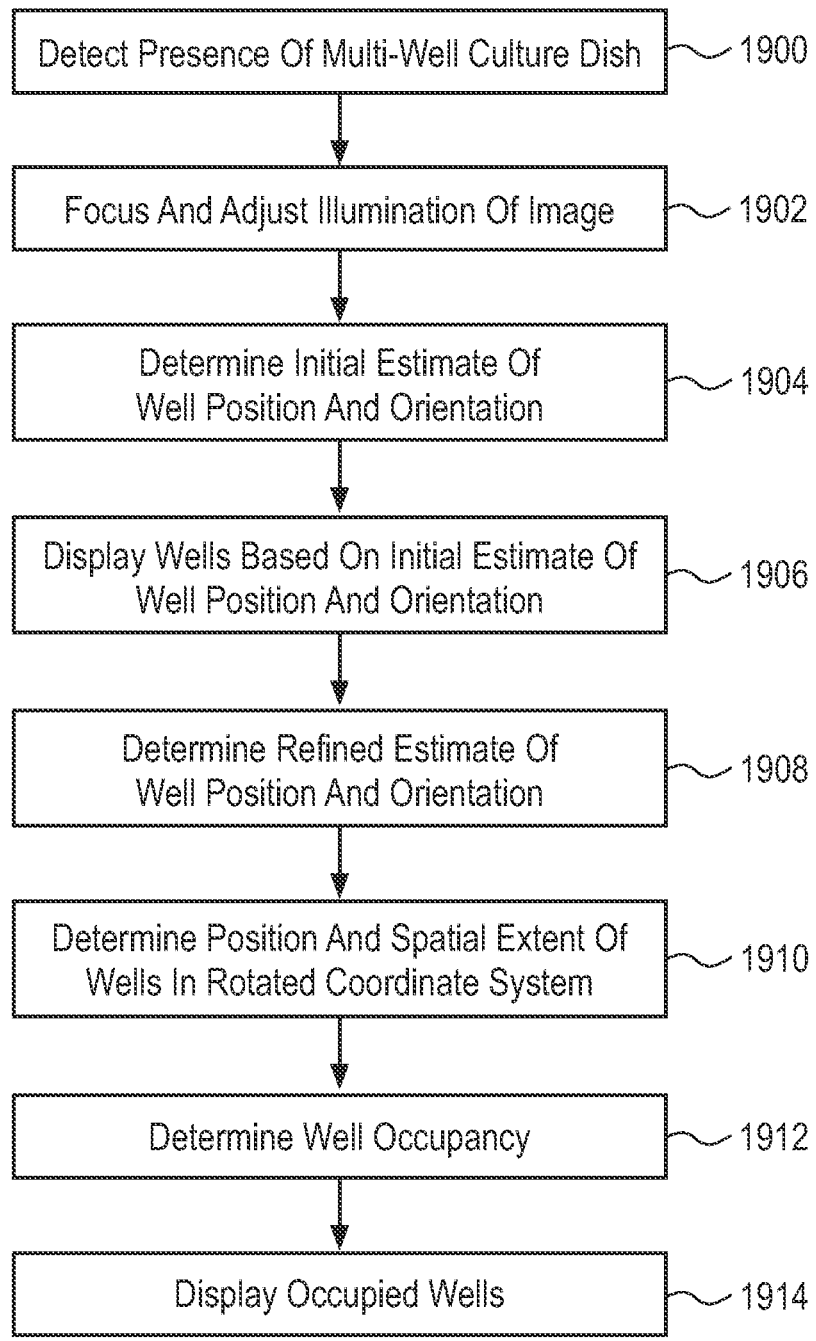
FIG. 19 illustrates operations associated with detecting a multi-well culture dish and determining occupancy of a plurality of micro-wells included in the multi-well culture dish, according to an embodiment of the invention.

FIG. 19 illustrates operations associated with detecting the multi-well culture dish 900 and determining occupancy of the plurality of micro-wells 910 included in the multi-well culture dish 900, according to an embodiment of the invention. The dish detection module 1820 detects presence of the multi-well culture dish 900 in an image detected by an imaging camera included in the microscope with imaging camera 1810 (block 1900). A goal of dish detection is to determine whether a dish is placed on the loading platform (such as the loading platform 210 described with reference to FIG. 2) properly and oriented with an acceptable angle. Dish detection, along with various other operations illustrated in FIG. 19, depend on characteristics of the dish 900, such as those described with reference to FIG. 20.

Figure 20:
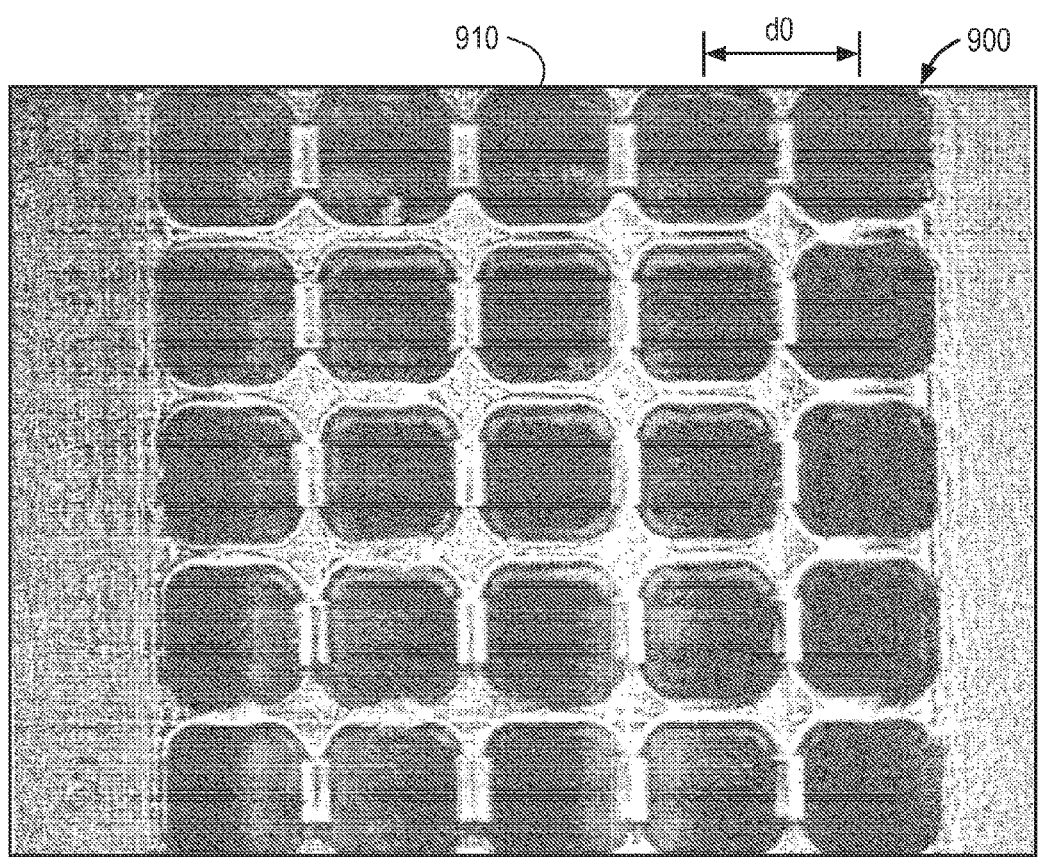
FIG. 20 illustrates a grid of wells included in a multi-well culture dish, according to an embodiment of the invention.

FIG. 20 illustrates a grid of wells 910 included in the multi-well culture dish 900, according to an embodiment of the invention. In one embodiment, the dish 900 has a square grid pattern of wells 910. The distance between well centers is the grid spacing (d0).

Figure 21:
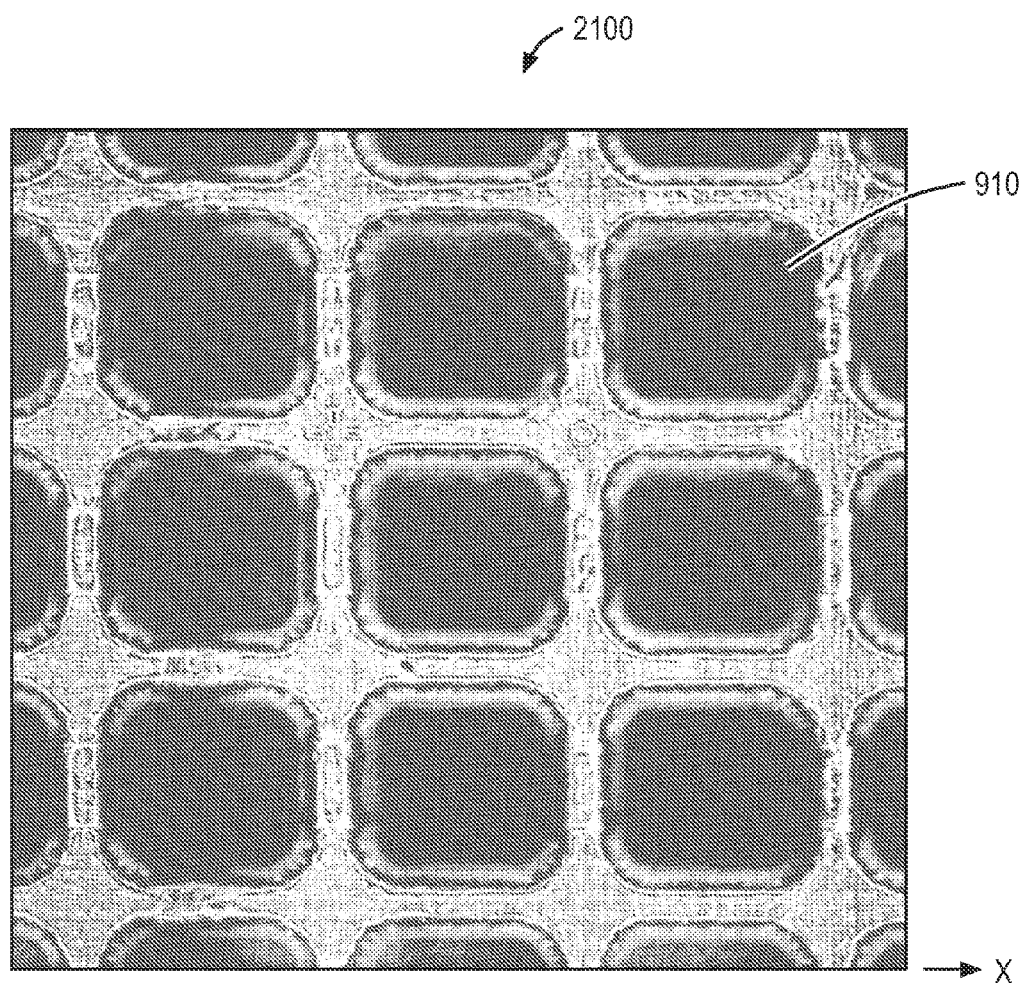
FIG. 21 illustrates a template representing a full extent of multiple micro-wells included in a template multi-well culture dish, according to an embodiment of the invention.

FIG. 21 illustrates a template 2100 representing a full extent of multiple micro-wells 910 included in a template multi-well culture dish, according to an embodiment of the invention. Dish detection can be based on the template 2100. For example, the template 2100 can be used to detect the presence of the dish 900. The template 2100 can be rotated in a range from –N degrees to N degrees (relative to the x-axis shown in FIG. 21), where N is in the range from about 2 to about 10, such as about 4, about 5, or about 6. This rotation of the template 2100 can be in increments of a fraction of a degree, such as increments of about ¼, ⅓, or ½ of a degree. Each rotated template is then matched against an original image (similar to the image 2200 in FIG. 22) of the dish 900, such as through normalized cross correlation. (Note that the original image of the dish 900 does not include the markings inserted in multiple micro-wells 910 shown in FIG. 22.) In one embodiment, the dish is considered present if the highest scoring template returns a normalized cross correlation score above a threshold, and if at least a subset of the micro-wells 910 in the original image of the dish 900 are fully in view. The threshold may be configurable, and may have a default value of about 0.5. The at least a subset of the micro-wells 910 may include either the top row or the bottom row of the micro-wells 910 in the original image of the dish 900. Alternatively, the at least a subset of the micro-wells 910 may be all of the wells in the original image of the dish 900. Also, in one embodiment, the template 2100 can be downsampled, such as by 5 times, 10 times, or 20 times, to facilitate dish detection being performed in real time, such that the user can be quickly notified of a result of the dish detection.

In one embodiment, if the dish is considered present, the autofocus module 1828 then focuses the original image of the dish 900, and the autoexposure module 1830 adjusts the illumination of the dish 900 (block 1902). Alternatively, if the dish is not considered present, a notification may be provided to a user, such as via a graphical user interface. In one embodiment, autofocus on the dish 900 varies the autofocus motor of the imaging camera in the microscope with imaging camera 1810 until an autofocus metric is maximized. The autofocus metric can be based on energy in the gradient image obtained through a Sobel operator. The Sobel operator convolves a pair of 3×3 kernel matrices with an image A, and results in two gradient images, in y and x directions. These matrices are:

$$G_y = \begin{bmatrix} -1 & -2 & -1 \\ 0 & 0 & 0 \\ +1 & +2 & +1 \end{bmatrix} * A \text{ and } G_x = \begin{bmatrix} -1 & 0 & +1 \\ -2 & 0 & +2 \\ -1 & 0 & +1 \end{bmatrix} * A \quad (1)$$

The magnitude gradient at each pixel is given by $$G = \sqrt{G_x^2 + G_y^2} \quad (2)$$

The autofocus metric is the root mean square of the per pixel magnitude gradients:

$$AFM(I) = \frac{1}{N}\sqrt{\sum_{i=1}^{N} G_i^2} \quad (3)$$

In one embodiment, autoexposure seeks to vary illumination of the original image of the dish 900 by adjusting the intensity of the light source included in the microscope with imaging camera 1810 until the variance of the image falls within a certain range. The variance of an image I is given by:

$$\text{var}(I) = \frac{1}{N}\sum_{i=1}^{N}(x_i - \bar{x})^2 \quad (4)$$

where $x_i$ is the ith pixel of image I, and $\bar{x}$ is the mean pixel value of image I. In one embodiment, the target range for this variance after autoexposure is between 4000 and 6000.

The well location determination module 1822 is then configured to determine a position of each of the micro-wells 910 included in the dish 900. In one embodiment, the well location determination module 1822 determines an initial estimate of well position and orientation (block 1904). The well location determination module 1822 can determine initial estimates of an orientation of the dish 900 and a position of a center point of the dish 900.

Figure 22:
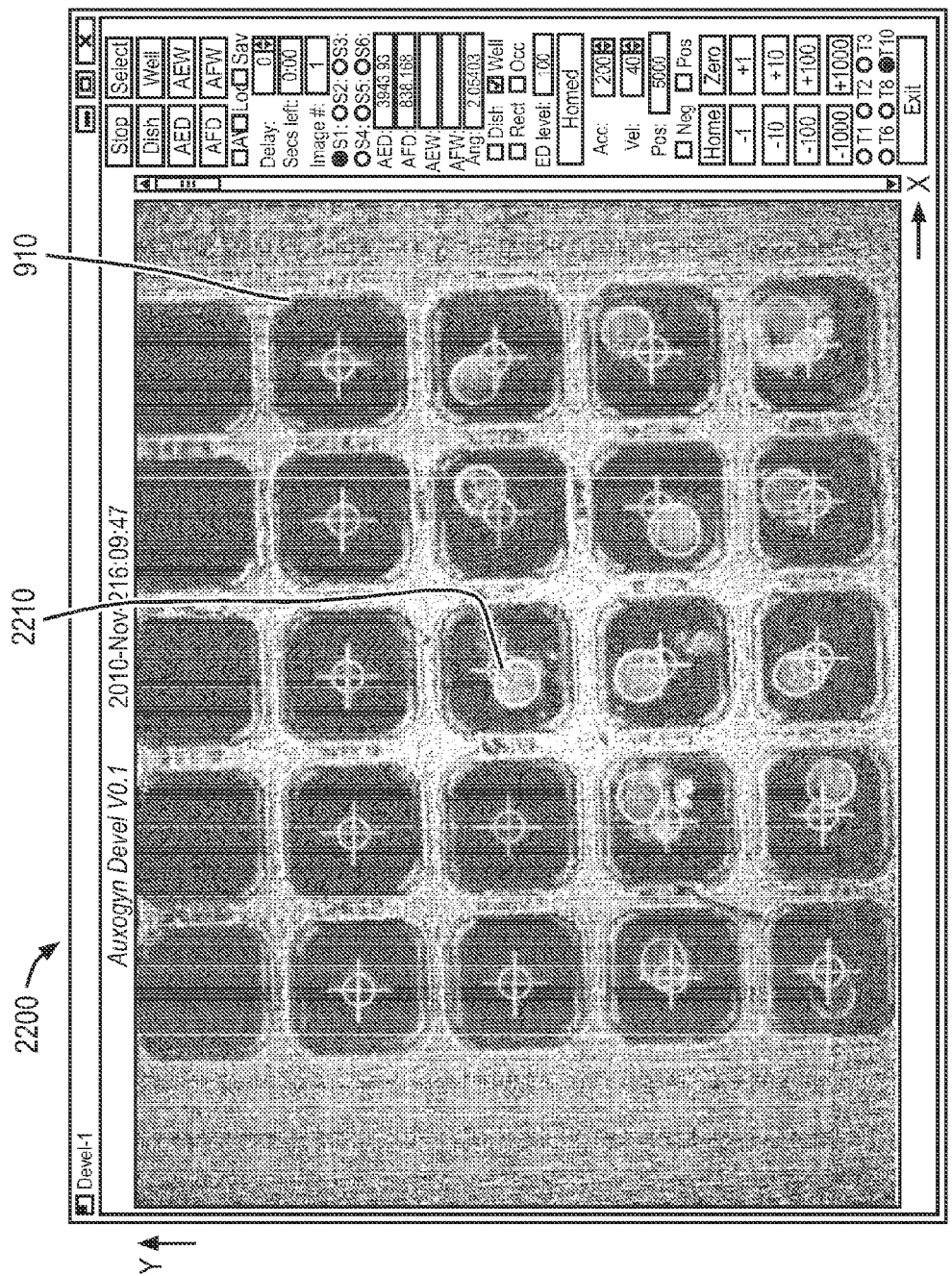
FIG. 22 illustrates an original image of micro-wells included in a dish with markings inserted to indicate positions of centers of multiple micro-wells, according to an embodiment of the invention.

FIG. 22 illustrates an original image of micro-wells 910 included in the dish 900 with markings inserted to indicate positions of centers of multiple micro-wells 910, according to an embodiment of the invention. As part of determining initial estimates of position and orientation of the micro-wells 910, the well location determination module 1822 can determine an orientation of the dish 900 and a position of the center point of the dish 900. The orientation of the dish 900 and the position of the center point of the dish 900 can be measured in a first coordinate system of the original image of the dish 900. The x-axis and the y-axis of this first coordinate system are illustrated in FIG. 22.

In one embodiment, the well location determination module 1822 can use the normalized cross-correlation with the template 2100 (described with reference to FIG. 21 and block 1900 of FIG. 19) to determine the initial estimates of the orientation of the dish 900 and the position of the center point of the dish 900. As described previously with reference to FIG. 21, the template 2100 can be incrementally rotated and matched against the original image of the dish 900. The rotated template 2100 resulting in the highest normalized cross-correlation score can be used to determine the initial estimates of the orientation of the dish 900 and the position of the center point of the dish 900. For example, the initial estimate of the orientation of the dish 900 can be given directly by the rotation angle of the maximizing template 2100. The initial estimate of the position of the center point of the dish 900 can be determined by the location of the cross correlation peak. In one embodiment, the well location determination module 1822 can then determine initial estimates of the center (and therefore the position) of each of the micro-wells 910 from the initial estimate of the center point of the dish 900. For example, in one embodiment a position 2210 (see FIG. 22) of the center point of the dish 900 corresponds to the position of the center of one of the micro-wells 910. Because the grid spacing d0 (see FIG. 20) and the orientation of the dish 900 are known, the well location determination module 1822 can then directly determine the initial estimates of the positions of the centers of the other micro-wells 910. In addition, the well location determination module 1822 can directly determine initial estimates of the positions of dish points included in the dish 900 (see dish points 2402 in FIG. 24). These initial estimates of the positions of the dish points can be referred to as reference dish points (see description with reference to block 1908 of FIG. 19).

In one embodiment, the display module 1826 then displays the micro-wells 910 based on the initial estimates of the positions and orientations of the micro-wells 910 (block 1906). The image 2200 illustrated in FIG. 22 is an example of a display of the micro-wells 910 based on the initial estimates of the positions and orientations of the micro-wells 910, with the initial estimates of the positions of the centers of multiple micro-wells 910 marked by the "+" signs in FIG. 22.

In one embodiment, the initial estimates of the positions and orientations of the micro-wells 910 can also be determined with a downsampled version of the template 2100, such as by 5 times, 10 times, or 20 times, to facilitate the initial estimates of the positions and orientations of the micro-wells 910 being performed in real time such that the initial estimates of the positions and orientations of the micro-wells 910 can be quickly displayed to a user.

In one embodiment, the well location determination module 1822 then determines a refined estimate of well position and orientation (block 1908). The well location determination module 1822 can determine refined estimates of an orientation of the dish 900 and a position of a center point of the dish 900. The well location determination module 1822 can also determine a refined estimate of the grid spacing d0 (see FIG. 20).

Figure 23:
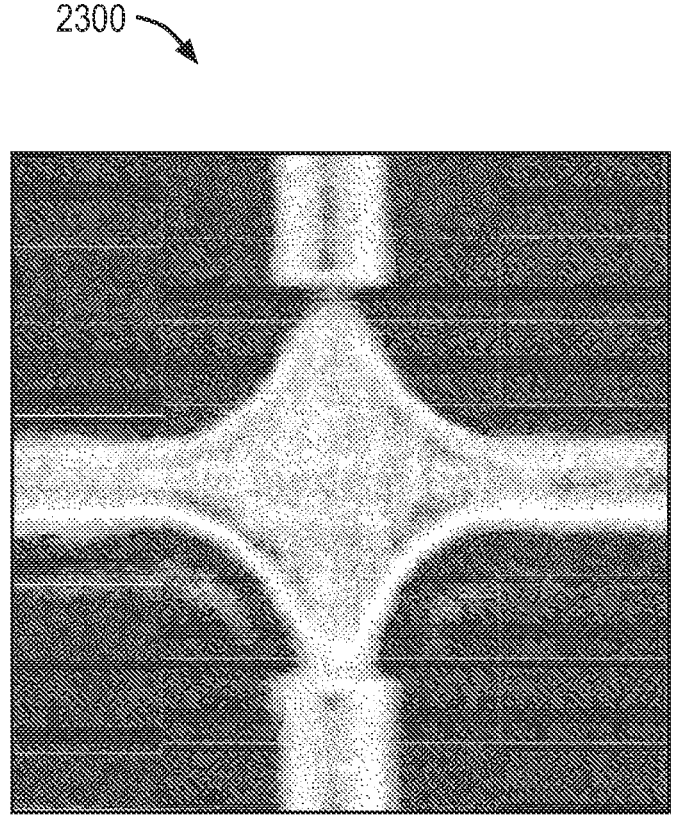
FIG. 23 illustrates a template representing a boundary between multiple micro-wells included in a template multi-well culture dish, according to an embodiment of the invention.
Figure 24:
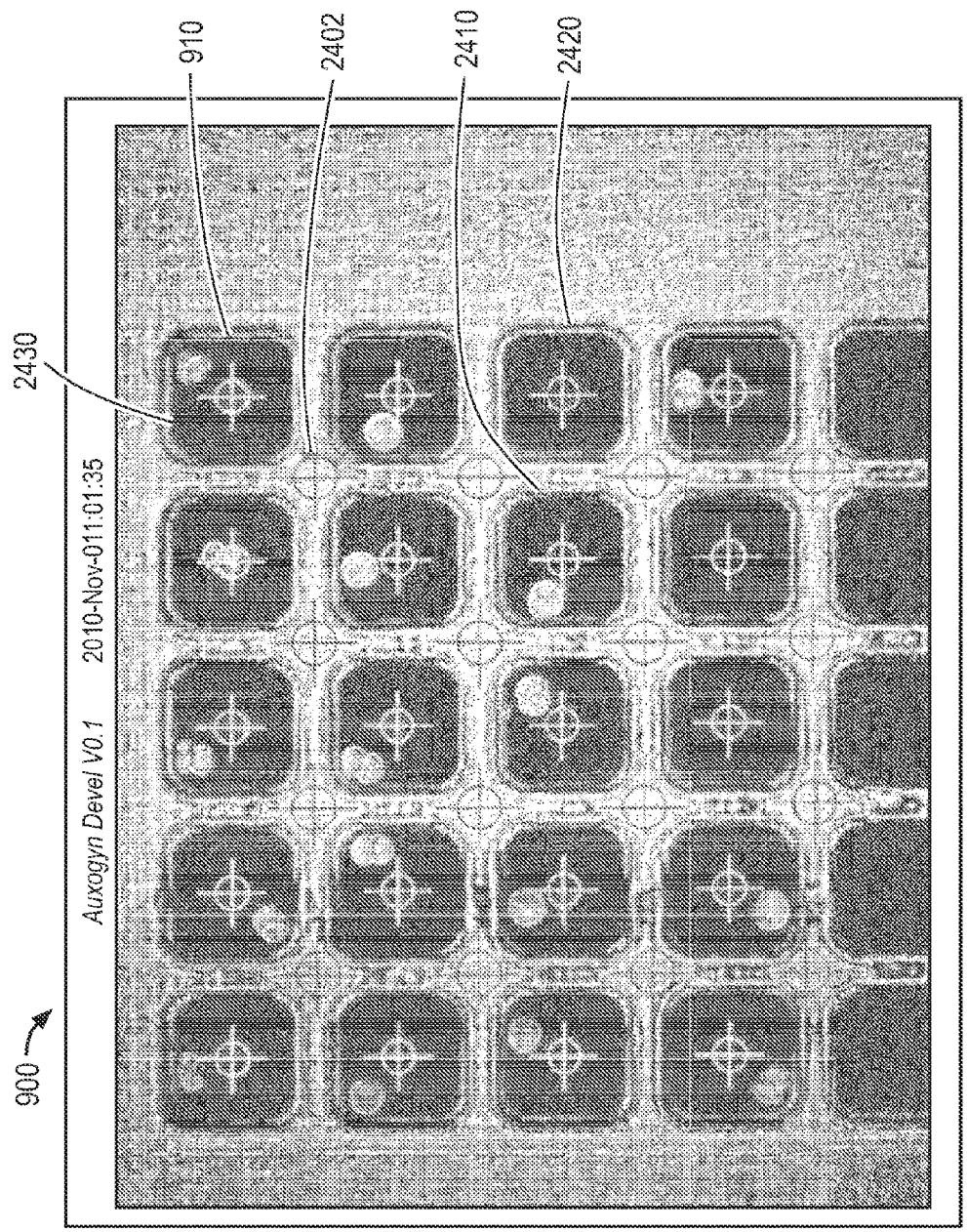
FIG. 24 illustrates an interconnected network of dish points included in a dish, according to one embodiment of the invention.

Refined estimates of the orientation of the dish 900, the position of the center point of the dish 900, and the grid spacing d0 can be determined based on repetitive structural features of the dish 900 that are smaller in extent than the template 2100 (see FIG. 21). FIG. 23 illustrates a template 2300 representing a boundary between multiple micro-wells 910 included in a template multi-well culture dish, according to an embodiment of the invention. FIG. 24 illustrates an interconnected network of dish points 2402 included in the dish 900, according to one embodiment of the invention. In one embodiment, the dish points 2402 can be evenly spaced in a grid. As illustrated in FIG. 24, the dish points 2402 are at intersections of the micro-wells 910. The template 2300 can be a single dish point 2402 (see FIG. 24), or can be an average of multiple dish points 2402.

In one embodiment, the well location determination module 1822 detects the dish points 2402 (see FIG. 24) with the template 2300. The template 2300 may be used directly by the well location determination module 1822, or may be downsampled by the well location determination module 1822, such as by 2 times or by 3 times. The matching of the template 2300 to the original image of the dish 900 may be done through normalized cross correlation. For example, at a given location in the original image of the dish 900, the template 2300 may be rotated through a range of orientations around the initial estimate of the orientation of the dish 900 determined by the well location determination module 1822 in block 1904. This is to determine the highest normalized cross-correlation score at that location in the original image of the dish 900. The template 2300 can be rotated in a range from −N degrees to N degrees, where N is in the range from about 1 to about 5, such as about 2, about 3, or about 4. This range of orientations can be smaller than the range of orientations through which the template 2100 (see FIG. 21) is rotated to obtain the initial estimate of the orientation of the dish 900. This rotation of the template 2300 can be in increments of a fraction of a degree, such as increments of about ¼, ⅓, or ½ of a degree.

In one embodiment, to prevent false positives, the well location determination module 1822 can select a first number of points in the original image of the dish 900 with the highest normalized cross-correlation scores with the template 2300 (see FIG. 23), where the first number is greater than a second number of dish points 2402 (see FIG. 24) expected to be present in the dish 900. For example, FIG. 24 illustrates that one embodiment of the dish 900 includes 16 dish points 2402. In this example, to prevent false positives, the well location determination module 1822 can select 20 candidate dish points in the original image of the dish 900 based on the 20 highest normalized cross-correlation scores with the template 2300. Alternatively, the well location determination module 1822 can select the first number of points such that the first number is equal to the second number of dish points 2402 expected to be present in the dish 900.

In one embodiment, to infer the dish points 2402 from the candidate dish points, the well location determination module 1822 determines a best match between each reference dish point (as described previously, initial estimate of the dish point) and the candidate dish points. This can be referred to as a correspondence between the reference dish points and the candidate dish points. To determine the correspondence, the well location determination module 1822 can perform a nearest neighbor search. The search can find the closest of the candidate dish points to each reference dish point. The result is the corresponding candidate dish point. If a correspondence is not found within a certain radial distance from a reference dish point, the reference dish point can be kept as is (without being refined). This process can be repeated for each of the reference dish points.

The well location determination module 1822 can determine a refined estimate of the position of the center point of the dish 900 (illustrated as point 2210 in FIG. 22) by averaging the x-coordinates and the y-coordinates of all of the refined dish points determined from the correspondence previously described. If the dish 900 includes a rectangular grid instead of a square grid of micro-wells 910, the center point of the dish 900 may be offset from a center point of one of the micro-wells 910 by a fraction of the grid spacing d0 (see FIG. 20) that can be determined based on the geometry of the dish 900.

The well location determination module 1822 can determine a refined estimate of the orientation of the dish 900 and the grid spacing d0 (see FIG. 20) based on the geometry of each of the refined dish points in relation to its neighbor refined dish points. The geometry of the refined dish points is fully defined by the vectors between adjacent pairs of refined dish points in row or column order. The refined estimate of the grid spacing d0 can be determined by averaging the length of each of these vectors. The refined estimate of the orientation of the dish 900 can be determined based on the slopes of these vectors.

An example is now presented of determination by the well location determination module 1822 of the refined estimates of well position and orientation based on the correspondence results associated with the 16 dish points 2402 illustrated in FIG. 24. The 16 correspondence results form an ordered set of points p0-p15, numbered in row scan order. In this ordering scheme, points p0, p3, p12, and p15 are corner points, and each have two neighbors at distance roughly d0 (see FIG. 20) away. Similarly, points p1, p2, p4, p7, p8, p9, p11, p13, and p14 (other boundary points) each have three such neighbors, and the remaining points (interior points) each have four such neighbors.

In this example, the vectors between adjacent pairs of refined dish points can be determined by subtracting the x-coordinates and y-coordinates of each refined dish point from its neighboring refined dish points (along row or column directions of the grid of micro-wells 910). Unit vectors can then be obtained by normalizing the vectors by their lengths. Since the order of the refined dish points is known at this stage from the correspondence results, it is known which vectors extend along row directions, and which vectors extend along column directions of the grid of micro-wells 910. In this example, there are 12 vectors that extend along row directions, and 12 vectors that extend along column directions. The well location determination module 1822 can determine grid generating unit vectors $u_1$ and $u_2$ as averages of the 12 vectors that extend along row directions, and the 12 vectors that extend along column directions, respectively:

$$u_1 = \left(\frac{1}{12}\right)\sum_{i=0}^{3}\sum_{j=1}^{3} (p(4i+j) - p(4i+j-1)) \tag{5}$$

$$u_2 = \left(\frac{1}{12}\right)\sum_{i=1}^{3}\sum_{j=0}^{3} (p(4i+j-4) - p(4i+j)) \tag{6}$$

This example can easily be generalized to grids of micro-wells 910 of other sizes than that shown in FIG. 24.

The well location determination module 1822 can determine the refined estimate of the orientation (angle α) of the dish 900 based on a slope $m_1$ of the grid generating unit vector $u_1$, and based on a slope $m_2$ of the grid generating unit vector $u_2$:

$$\alpha = \tan^{-1}\left(\frac{m_1 - \frac{1}{m_2}}{2}\right) \tag{7}$$

In one embodiment, the display module 1826 may then display the micro-wells 910 based on the refined estimates of the positions and orientations of the micro-wells 910.

Figure 25:
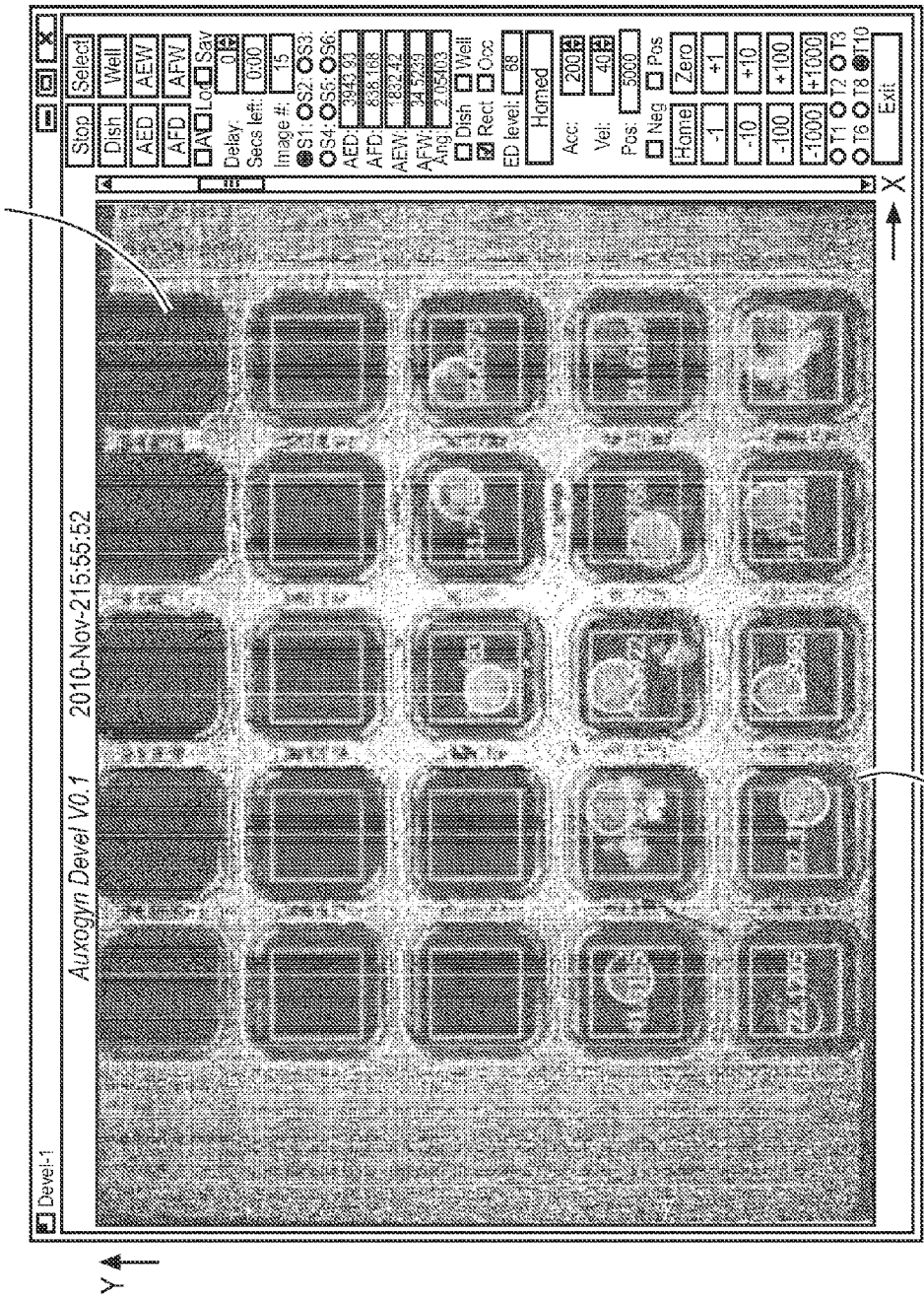
FIG. 25 illustrates an image of micro-wells included in a dish in a rotated coordinate system, according to an embodiment of the invention.

In one embodiment, the well location determination module 1822 then determines a position and spatial extent of wells 910 in a rotated coordinate system (block 1910). In the rotated coordinate system, the dish 900 is rotated from its orientation in the original image to a reference orientation. For example, FIG. 22 illustrates the original image of the dish 900. FIG. 25 illustrates an image of micro-wells 910 included in the dish 900 in the rotated coordinate system, according to an embodiment of the invention.

The position (center) of inner micro-wells 2410 (in the embodiment shown in FIG. 24, there are nine inner micro-wells 2410) in the original coordinate system (of the original image of the dish 900) can be determined by averaging the x-coordinates and the y-coordinates of the four dish points 2402 surrounding each of the inner micro-wells 2410. The position (center) of outer, non-corner micro-wells 2420 (in the embodiment shown in FIG. 24, there are 12 outer, non-corner micro-wells 2420) can then be determined by incrementing or decrementing, as appropriate, the x-coordinates and/or the y-coordinates of a neighboring inner micro-well 2410. For example, if the outer micro-well 2420 has an adjacent inner micro-well 2410 in the same row, then the center of the outer micro-well 2420 can be determined from the center of the adjacent inner micro-well 2410 based on the refined estimate of the grid spacing d0 and the unit vector $u_1$ extending along the row direction. If the outer micro-well 2420 has an adjacent inner micro-well 2410 in the same column, then the center of the outer micro-well 2420 can be determined from the center of the adjacent inner micro-well 2410 based on the refined estimate of the grid spacing d0 and the unit vector $u_2$ extending along the column direction. The position (center) of corner micro-wells 2430 (in the embodiment shown in FIG. 24, there are 4 corner micro-wells 2430) can then be determined by incrementing or decrementing, as appropriate, the x-coordinates and/or the y-coordinates of a neighboring outer micro-well 2420.

In one embodiment, after determination of the well centers in the coordinate system of the original image (see x-axis and y-axis in FIG. 22), the well location determination module 1822 then determines the position and spatial extent of wells 910 in the rotated coordinate system (see x-axis and y-axis in FIG. 25). The well centers in the rotated coordinate system can be determined from the well centers in the coordinate system of the original image based on a rotation transform associated with the previously described refined estimate of the orientation (angle α) of the dish 900:

$$R = \begin{bmatrix} \cos(\alpha) & \sin(\alpha) \\ -\sin(\alpha) & \cos(\alpha) \end{bmatrix} \tag{8}$$

In one embodiment, the well location determination module 1822 may further refine the estimation of the well centers in the rotated coordinate system. For example, the rotation of Eqn. (8) may be configured to orient the dish 900 such that all well centers in a row of micro-wells 910 included in the dish 900 have the same x-coordinate, and such that all well centers in a column of micro-wells 910 included in the dish 900 have the same y-coordinate. If there is a difference between any of the x-coordinates of micro-wells 910 in the same row, the well location determination module may set the x-coordinates of all of the micro-wells 910 in the row to an average of the x-coordinates of all of the micro-wells 910 in the row. Similarly, if there is a difference between any of the y-coordinates of micro-wells 910 in the same column, the well location determination module may set the y-coordinates of all of the micro-wells 910 in the column to an average of the y-coordinates of all of the micro-wells 910 in the column.

In one embodiment, the well location determination module 1822 may determine the spatial extent of each micro-well 910 based on the estimate of the position of the center of the micro-well 910 in the rotated coordinate system. For example, based on a known width and shape of the micro-wells 910, the spatial extent of each micro-well 910 can be determined from the estimate of the position of the center of the micro-well 910 in the rotated coordinate system.

In one embodiment, the well location determination module 1822 may determine whether each micro-well 910 is fully in view in the image based on the spatial extent of each micro-well 910. If a micro-well 910 is not fully in view in the image, the display module 1826 can indicate this on a display, such as by showing the micro-well 910 in a different color from the other micro-wells 910.

In one embodiment, the well occupancy determination module 1824 then determines well occupancy (block 1912). The well occupancy determination module 1824 may determine occupied micro-wells 2510 (see FIG. 25) included in the plurality of micro-wells 910 based on the position of each of the plurality of micro-wells 910 previously determined by the well location determination module 1822. The well occupancy determination module 1824 may also make this determination based on the spatial extent of each of the plurality of micro-wells 910 previously determined by the well location determination module 1822.

The occupancy of each micro-well 910 can be determined based on a percentage of pixels in the micro-well 910 (in the rotated image) that exceed a brightness threshold. The brightness threshold may be determined based on a mean intensity value of the pixels in the micro-well 910. For example, the brightness threshold may be set to be N times the mean intensity value of the pixels in the micro-well 910, where N can be in the range from about 1.5 to about 3.5, such as about 2, or about 3. An occupancy measure for the micro-well 910 can then be determined as the percentage of pixels in the micro-well 910 that exceed the brightness threshold. The well occupancy determination module 1824 can determine that the micro-well 910 is occupied if the occupancy measure is greater than an occupancy threshold. For example, the occupancy threshold may be in the range from about 2 percent to about 10 percent, such as about 4 percent, about 5 percent, or about 6 percent.

In one embodiment, after determination of the occupancy of each micro-well 910, the display module 1826 displays at least the occupied micro-wells 2510 (see FIG. 25) (block 1914). The display module 1826 may generate a masked image based on the rotated image, such that only the occupied micro-wells are included in the masked image. The autofocus module 1828 may then focus the masked image, and the display module 1826 may then display the masked image.

Figure 32:
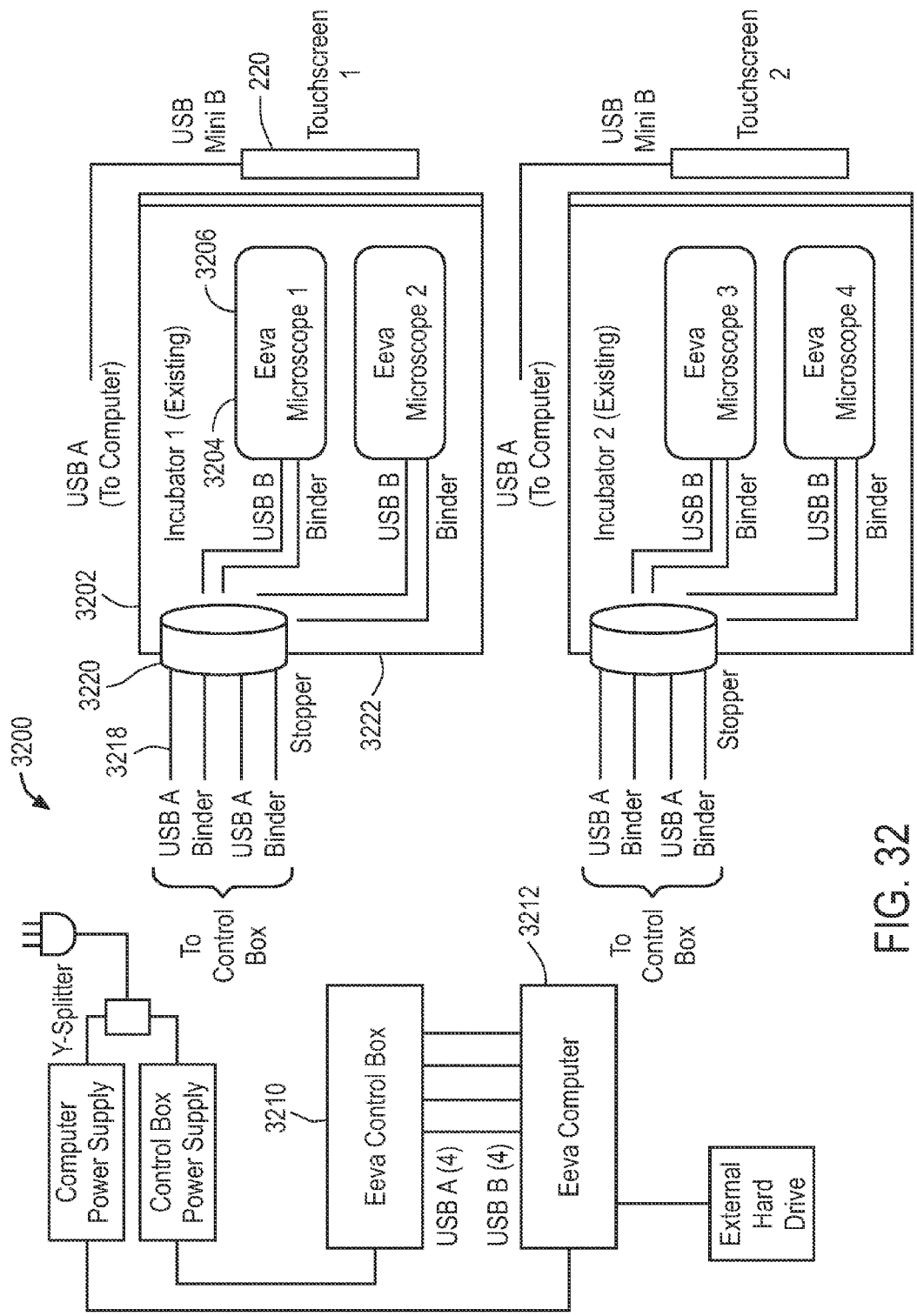
FIG. 32 illustrates a schematic diagram of a system for automated imaging and evaluation of human embryos, oocytes, or pluripotent cells for use with incubators, according to one embodiment of the invention.

Referring to FIG. 32, a schematic diagram of a system 3200 for automated imaging and evaluation of human embryos, oocytes, or pluripotent cells for use with incubators 3202 is illustrated, according to one embodiment of the invention. The incubators 3202 include one or more shelves for holding imaging microscopes 3204. Each imaging microscope 3204 is located inside a corresponding housing 3206, and includes at least one light source and at least one imaging camera. The housings 3206 are located inside corresponding ones of the incubators 3202. In one embodiment, each incubator 3202 can hold multiple imaging microscopes 3204. In one embodiment, a loading platform (not shown) extending outward from the housing 3206 allows for a multi-well culture dish (such as the multi-well culture dish 215 of FIG. 2, the multi-well culture dish 900 of FIG. 9, or the multi-well culture dish 2600 of FIG. 26) to be positioned for imaging by the imaging microscope 3204.

Each housing 3206 is in many respects similar to the housing 205 described with reference to FIG. 2, so differences are described here. The housing 3206 can include a module (not shown) for electrically interfacing the imaging microscope 3204 to a controller 3210 located outside the incubators 3202. In one embodiment, the controller 3210 controls the at least one light source included in each of the imaging microscopes 3204, and may also include a driver for a motor included in the imaging camera included in each of the imaging microscopes 3204. Advantageously, because the controller 3210 located outside of the incubators 3202 performs these functions, heat generated by circuitry, logic, and/or processing elements implementing these functions is dissipated outside of the incubators 3202. This can facilitate precise control of temperature inside the incubators 3202, which, for example, can be important for embryos stored within the incubators 3202 and being imaged by the imaging microscopes 3204. Additionally, because each of the imaging microscopes 3204 no longer needs to incorporate these additional circuitry, logic, and/or processing elements, the size of the imaging microscopes 3204 can be reduced.

In one embodiment, the controller 3210 may perform various monitoring functions to determine whether components of the imaging microscopes 3204 are exhibiting unexpected behavior. These monitoring functions may include camera current monitoring, motor current monitoring, imaging light source monitoring, and alignment light source monitoring. For current monitoring, the controller 3210 may measure current to the camera and/or the motor, and determine whether the current exceeds a threshold. For example, the camera current monitor may trigger after the equivalent of 5 minutes of 15% freerun. The motor current monitoring may trigger after the equivalent of 30 seconds of 100% duty cycle, or 4 minutes of 25% duty cycle. If the current exceeds the threshold, the controller 3210 may shut down the camera and/or the motor. Alternatively or in addition, the controller 3210 may trigger an alarm to notify a user that the current has exceeded the threshold. This alarm, and other operational status indicators, may be displayed by a graphical user interface of a computer 3212 electrically connected to the controller 3210.

For light source monitoring, the controller 3210 may measure a time duration that the imaging light source (such as the light source 3002 described with reference to FIG. 30) and/or the alignment light source (such as the indicator LED described with reference to FIG. 8) have been on, and determine whether the time duration exceeds a threshold. For example, the controller 3210 may turn off the imaging light source if the imaging light source has been on for a time duration longer than a threshold in the range from about 5 seconds to about 15 seconds, such as about 10 seconds. The controller 3210 may turn off the alignment light source if the alignment light source has been on for a time duration longer than a threshold in the range from about 1 minutes to about 7 minutes, such as about 3 minutes, about 4 minutes, or about 5 minutes. In addition, in both of these cases the controller 3210 may trigger an alarm to notify a user that the light source has been on for a time duration longer than the threshold. This alarm, and other operational status indicators, may be displayed by a graphical user interface of a computer 3212 electrically connected to the controller 3210.

In one embodiment, the controller 3210 is electrically connected to the imaging microscopes 3204 located within an incubator 3202 via cables 3218, such as USB cables. The cables 3218 enter the incubator 3202 through openings in a stopper 3220. The stopper 3220 fits snugly in an opening in a rear panel 3222 of the incubator 3202 to prevent air outside of the incubator 3202 from flowing into the incubator 3202.

In one embodiment, the computer 3212 is electrically connected to the imaging microscopes 3204 via the controller 3210. For example, images generated by the imaging microscopes 3204 are transmitted to the computer 3212 via the controller 3210. In contrast, the touch-screen panel 220 (described with reference to FIG. 2) may be connected to the computer 3212 without being connected to the controller 3210.

In one embodiment, the controller 3210 includes switches (not shown), where each of the switches is configured to reset the alarms associated with a corresponding one of the imaging microscopes 3204. These switches provide a manual, hardware-based mechanism for resetting these alarms that is not dependent on software control or involvement (such as software executing on the computer 3212).

Figure 33:
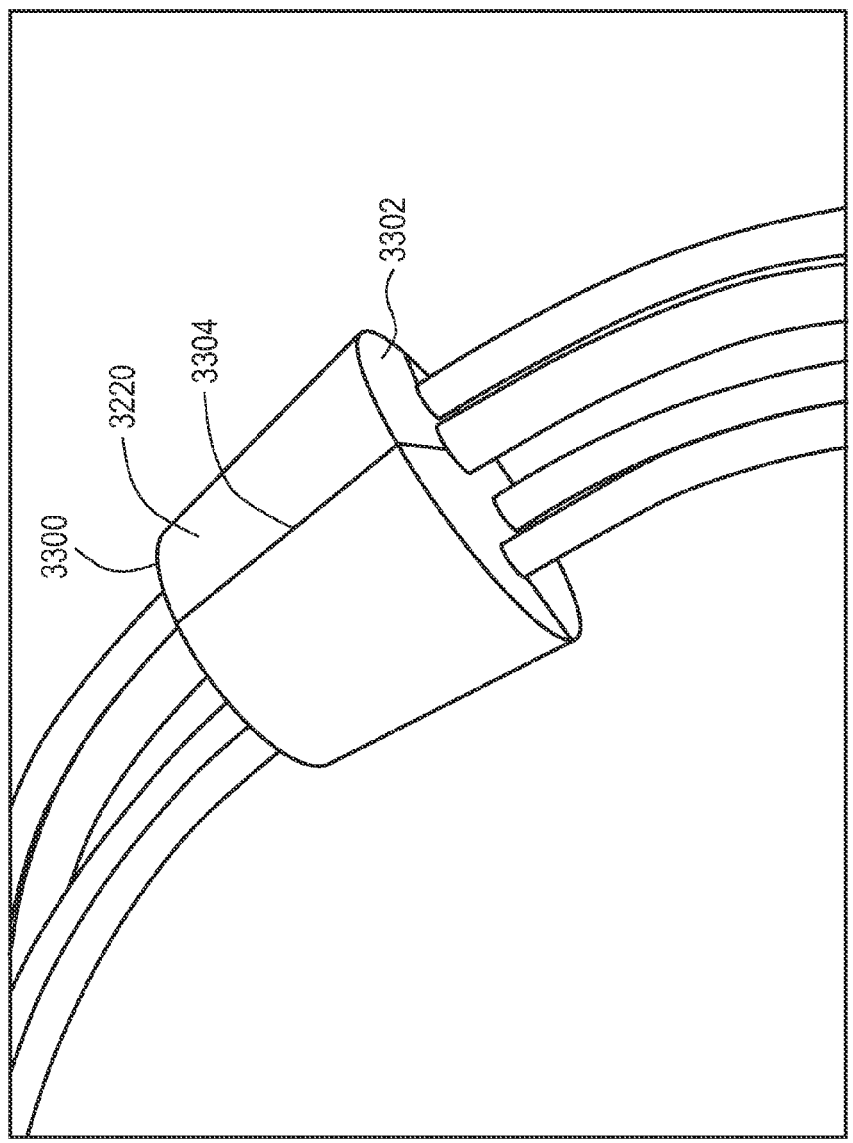
FIG. 33 illustrates a schematic view of a stopper, according to an embodiment of the invention.
Figure 34:
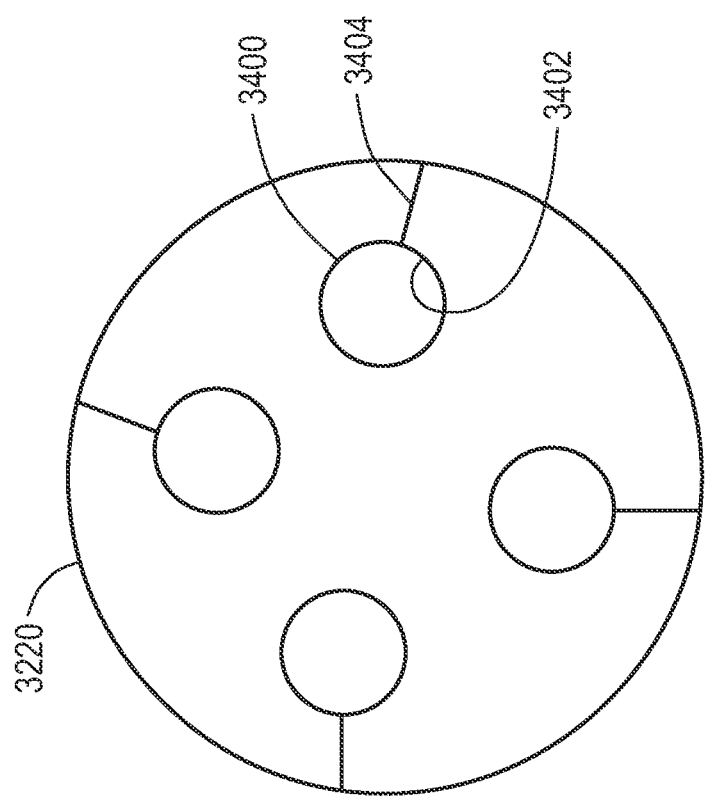
FIG. 34 illustrates a cross-section view of a stopper, according to an embodiment of the invention.

FIG. 33 illustrates a schematic view of the stopper 3220, according to an embodiment of the invention. FIG. 34 illustrates a cross-section view of the stopper 3220, according to an embodiment of the invention. Referring to FIG. 33, the stopper 3220 includes an upper surface 3300, a lower surface 3302, and a lateral periphery 3304 extending between the upper surface 3300 and the lower surface 3302. Referring to FIGS. 33 and 34, the stopper 3220 defines openings 3400, where each of the openings 3400 extends from the upper surface 3300 to the lower surface 3302 and is circumscribed by an inner lateral surface 3402 of the stopper 3220. The stopper 3220 defines slits 3404, where each of the slits 3404 extends from the lateral periphery 3304 to the inner lateral surface 3402 circumscribing the corresponding one of the openings 3400. Each of the slits 3404 is configured such that each of the cables 3218 is insertable into a corresponding one of the openings 3400 through a corresponding one of the slits 3404. Before the stopper 3220 is inserted into the opening in the rear panel 3222 of the incubator 3202, each of the cables 3218 is slidably adjustable in the corresponding one of the openings 3400. When the stopper 3220 is inserted into the opening in the rear panel 3222, this creates a compression seal such that each of the cables 3218 is held in place by the compression seal.

The slits 3404 in the stopper 3220 facilitate insertion of the cables 3218 into the openings 3400 in the stopper 3220, which facilitates the installation of the imaging microscopes 3204 into the incubators 3202. Prior to insertion of the stopper 3220 into the opening in the rear panel 3222 of the incubator 3202, the slits 3404 also facilitate the slidable adjustment of the cables 3218 in the openings 3400. After the insertion of the stopper 3220 into the opening in the rear panel 3222 of the incubator 3202, the compression seal that holds the cables 3218 in place helps to protect embryos being imaged by the imaging microscopes 3204 by reducing or eliminating motion or vibration of the embryos due to movement of the cables 3218.

Figure 35:
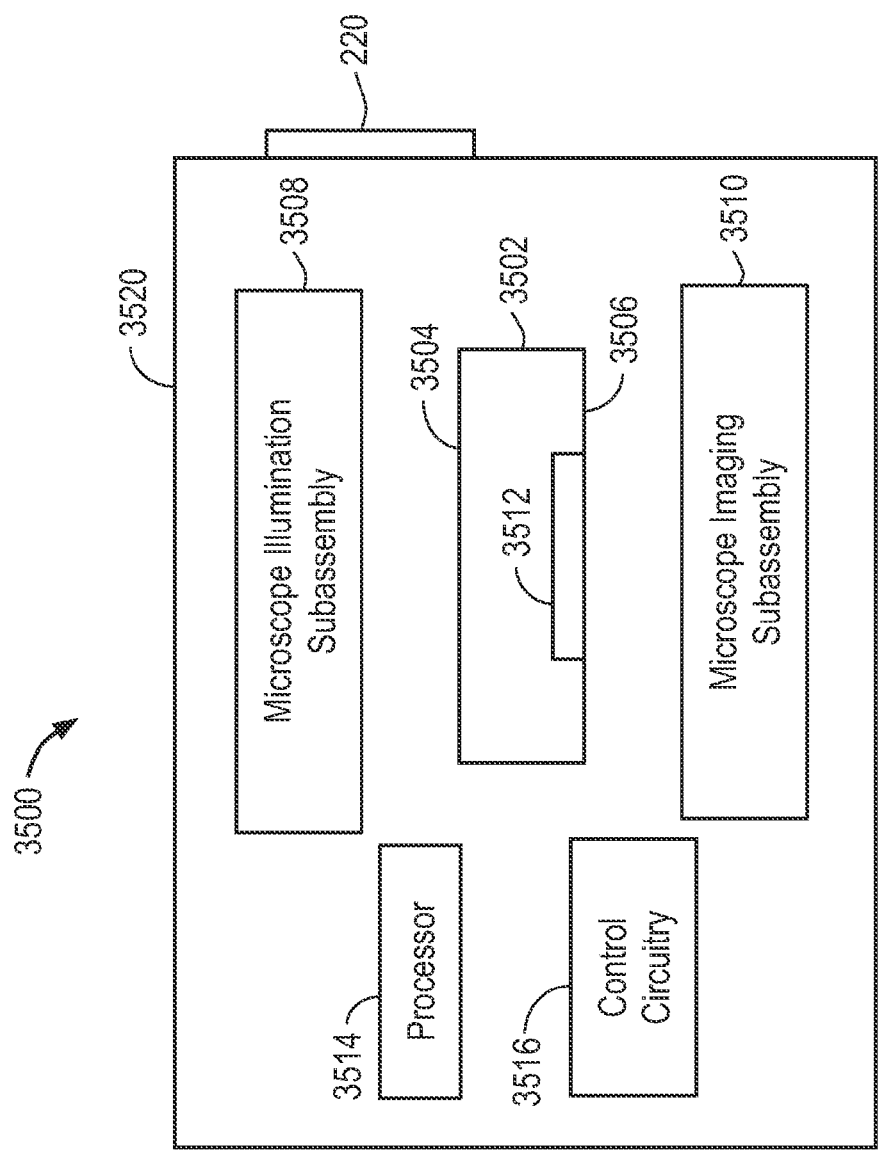
FIG. 35 illustrates an apparatus for automated imaging, according to an embodiment of the invention.

FIG. 35 illustrates an apparatus 3500 for automated imaging, according to an embodiment of the invention. In one embodiment, the apparatus 3500 includes a culture chamber 3502 configured to incubate a multi-well culture dish 3512 (such as the multi-well culture dish 215 of FIG. 2, the multi-well culture dish 900 of FIG. 9, or the multi-well culture dish 2600 of FIG. 26). The culture chamber 3502 may have an upper surface including a first window 3504, and a lower surface including a second window 3506. In one embodiment, the culture chamber 3502 is configured to hold in the range from 1 to 8 culture dishes. The apparatus 3500 may also include a time-lapse microscope including an illumination subassembly 3508 (similar to the illumination subassembly 405 described with reference to FIG. 4) and an imaging subassembly 3510 (similar to the imaging subassembly 410 described with reference to FIG. 4). The time-lapse microscope and the culture chamber 3502 are integrated into a common housing 3520.

The illumination subassembly 3508 may include a light source and the imaging subassembly 3510 may include an imaging camera. The light source and the imaging camera may be configured to generate images of the multi-well culture dish 3512 inside the culture chamber 3502 based on light from the light source passing through the first window 3504 and the second window 3506. A touch-screen panel 220 is configured to display a graphical user interface for controlling the time-lapse microscope.

In one embodiment, the apparatus 3500 includes a processor 3514. The processor 3514 may be configured to perform automated detection of presence of the multi-well culture dish 3512 and occupancy of micro-wells included in the multi-well culture dish 3512 (described with reference to FIGS. 18 through 25). The processor 3514 may also be configured to analyze images generated by the imaging camera included in the time-lapse microscope. Other functions performed by the controller 3210 and the computer 3212 (described with reference to FIGS. 32 and 36) may be performed by the processor 3514.

In one embodiment, the apparatus 3500 also includes control circuitry 3516. The control circuitry 3516 may include an electronic watchdog circuit configured to measure a time duration that a light source has been on, and to shut off the light source if the time duration is longer than a threshold, such as in the range from 5 seconds to 15 seconds. The control circuitry 3516 may also implement other monitoring functionality described with reference to FIG. 32.

In one embodiment, the apparatus 3500 may be implemented as a compact, benchtop-size device. This is facilitated by integration of functions performed by the controller 3210 and the computer 3212 (described with reference to FIGS. 32 and 36) onto the processor 3514 and the control circuitry 3516 in the common housing 3520. This is also facilitated by integration of the culture chamber 3502, the microscope illumination subassembly 3520, and the microscope imaging subassembly 3510 into the common housing 3520.

Figure 36:
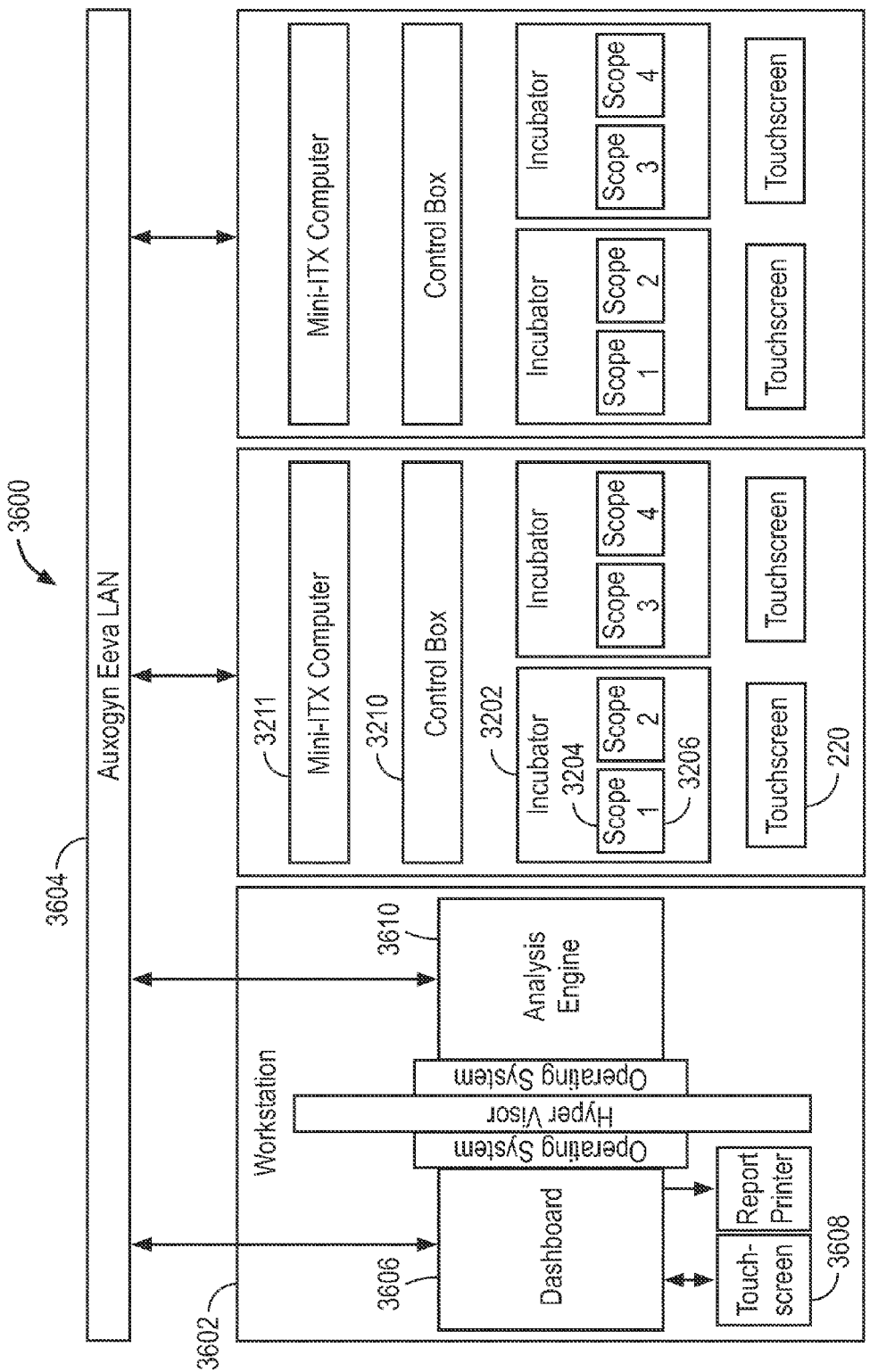
FIG. 36 illustrates a system for automated imaging and evaluation of human embryos, oocytes, or pluripotent cells, according to an embodiment of the invention.

FIG. 36 illustrates a system 3600 for automated imaging and evaluation of human embryos, oocytes, or pluripotent cells, according to an embodiment of the invention. Referring to FIGS. 32 and 36, the system 3600 includes the time-lapse microscopes 3204, each located in the corresponding housing 3206. One or more housings 3206 are located inside the incubator 3202. Each incubator 3202 has an associated touch-screen 220. The controller 3210 is configured to control one or more time-lapse microscopes 3204 located inside one or more incubators 3202. The controller 3210 may be associated with a computer 3211 electrically connected to the plurality of time-lapse microscopes 3204. The computer 3211 may be co-located with the incubators 3202, and may have a mini-ITX form factor.

Multiple computers 3211 at different locations may be connected to a server 3602 over a network 3604, such as a local area network or a wide area network. The network may be a wireline network, or may be a wireless network. The server 3602 may include a dashboard 3606 that is configured to display a graphical user interface that provides status information and parameters based on analysis of images of a human embryo or pluripotent cell, and an analysis engine 3610 that performs the analysis. The status information is associated with each of the time-lapse microscopes 3204, and at least one of the images is generated by each of the plurality of time-lapse microscopes 3204. The graphical user interface may be displayed on a touch-screen 3608, or on a conventional display.

In one embodiment, each controller 3210 may provide functions including patient information entry and display, control of loading of a multi-well culture dish including embryos or pluripotent cells to be imaged, control of focusing and exposure of the multi-well culture dish, detection of the multi-well culture dish, determination of occupancy of micro-wells included in the multi-well culture dish, image capture, buffering of the current session (if active) or the latest session (if inactive), and display of the latest image (including zoom on specific micro-wells).

In one embodiment, the dashboard 3606 may provide functions including display of status information associated with the time-lapse microscopes 3204, display of images generated by the time-lapse microscopes 3204, other graphical user interface functions related to monitoring of the time-lapse microscopes 3204 and review of analysis results, generation of prediction and image reports based on analysis by the analysis engine 3610, and export of time-lapse movies showing changes in a human embryo or pluripotent cell (within a given micro-well) over time. The dashboard may also support generation of billing reports related to functions performed by the various components of the system 3600.

In one embodiment, the analysis engine 3610 may perform functions including analysis of streams of images generated by the time-lapse microscopes 3204, generation of analysis results, and generation of time-lapse movies showing changes in a human embryo or pluripotent cell (within a given micro-well) over time.

In one embodiment, the server 3602 may also support archiving of image data, analysis data, billing data, and other data related to functions performed by the various components of the system 3600.

Figure 37:
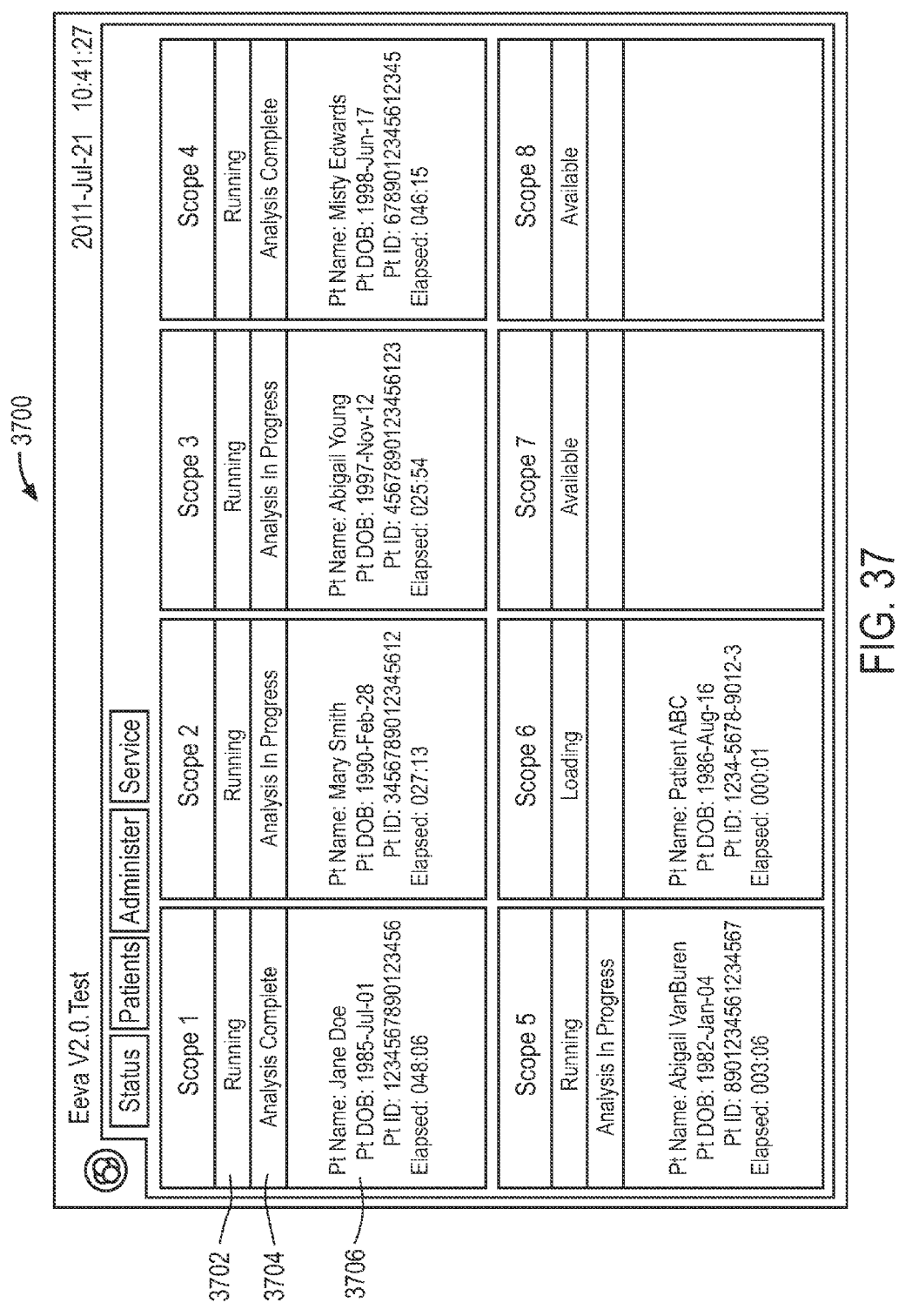

FIGS. 37-40 illustrate various display screens of a GUI for use with the dashboard 3606 of FIG. 36, according to an embodiment of the invention. FIG. 37 shows a display 3700 concurrently displaying patient information 3706 associated with multiple multi-well culture dishes, where each of the multi-well culture dishes is being imaged by a corresponding one of multiple time-lapse microscopes 3204 (see FIGS. 32 and 36). For each time-lapse microscope 3204, a first status 3702 is shown of image collection from the time-lapse microscope 3204, and a second status 3704 is shown of analysis of images, such as images previously collected from the time-lapse microscope 3204. The status information displayed for each time-lapse microscope may be the same, or may be different.

Figure 38:
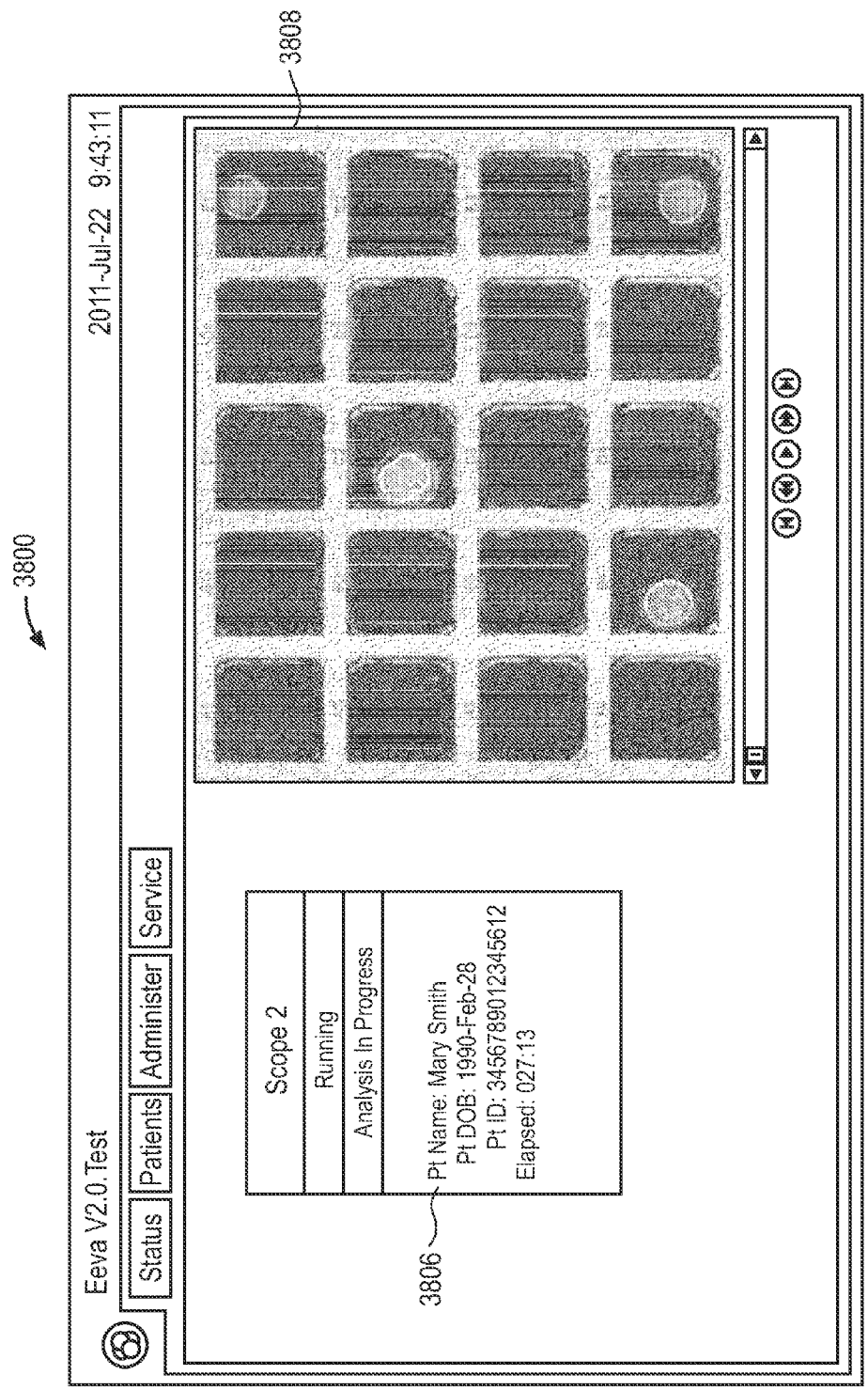

FIG. 38 shows a display 3800 that can be displayed upon receiving a selection associated with one of the multi-well culture dishes. The display 3800 shows patient information 3806 associated with that multi-well culture dish. An image 3808 of micro-wells included in that multi-well culture dish may also be displayed.

Figure 39:
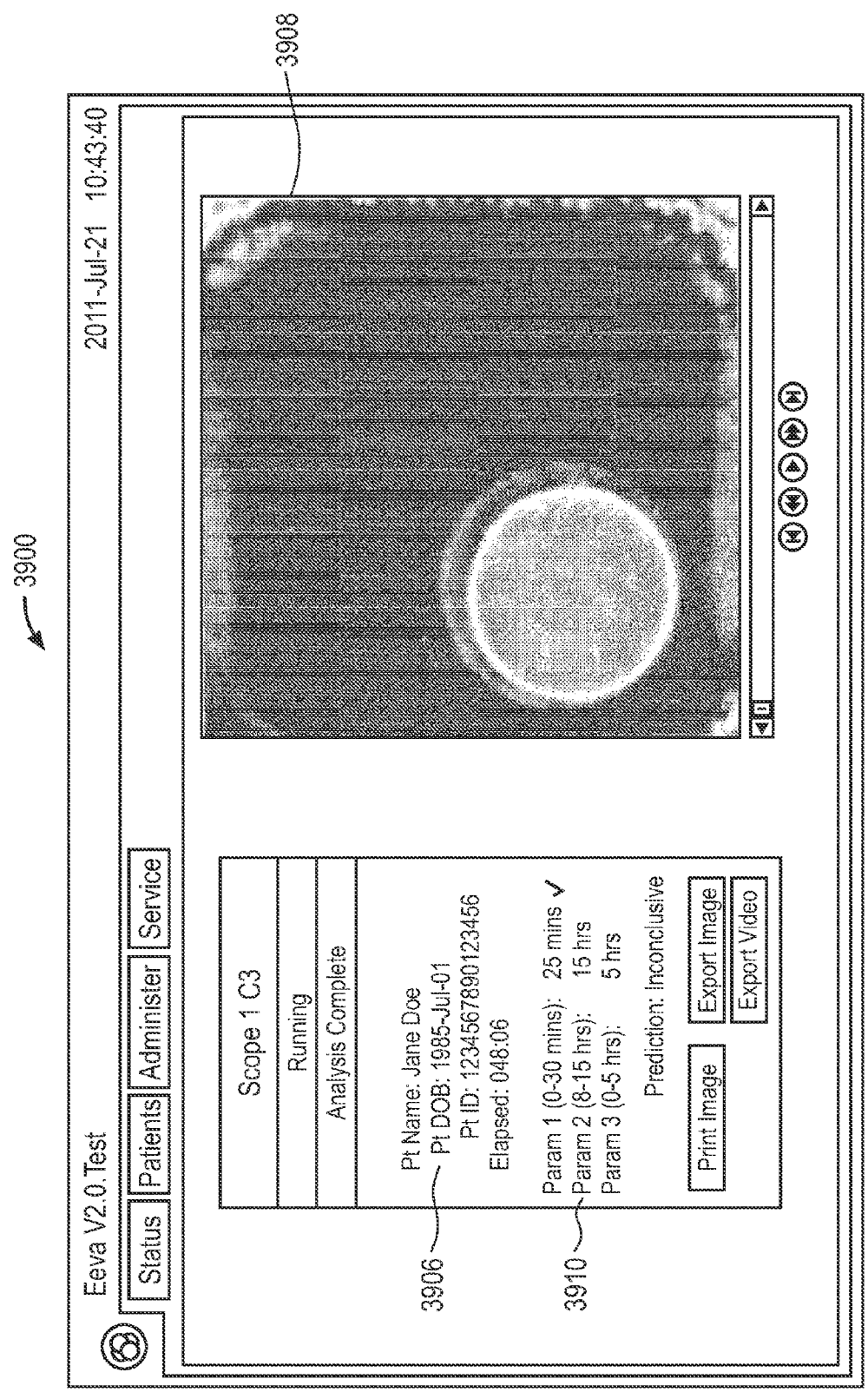

FIG. 39 shows a display 3900 that can be displayed upon receiving a selection associated with one of the micro-wells included in one of the multi-well culture dishes. The display 3900 shows patient information 3906 associated with that micro-well, an image 3908 of the micro-well, and parameters 3910 determined based on analysis of an embryo contained in the micro-well. Parameter 1 is a duration of first cytokinesis, parameter 2 is a time interval between cytokinesis 1 and cytokinesis 2, and parameter 3 is a time interval between cytokinesis 2 and cytokinesis 3.

FIG. 40 shows a display 4000 that shows a summary of patient information and image collection status for both patients (such as patient 4002) for whom images are currently being collected, and for patients (such as patient 4004) for whom images have previously been collected.

An embodiment of the invention relates to a computer storage product with a computer-readable medium having computer code thereon for performing various computer-implemented operations. The term "computer-readable medium" is used herein to include any medium that is capable of storing or encoding a sequence of instructions or computer codes for performing the operations described herein. The media and computer code may be those specially designed and constructed for the purposes of the invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

The preceding merely illustrates the principles of the invention. It is appreciated that those skilled in the art may be able to devise various arrangements which, although not explicitly described or shown herein, embody the principles of the invention and are included within its spirit and scope. The illustrations may not necessarily be drawn to scale, and manufacturing tolerances may result in departure from the artistic renditions herein. There may be other embodiments of the present invention which are not specifically illustrated. Thus, the specification and the drawings are to be regarded as illustrative rather than restrictive. Additionally, the drawings illustrating the embodiments of the present invention may focus on certain major characteristic features for clarity. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims. In addition, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A method for automated imaging and evaluation of human embryos, oocytes, or pluripotent cells with an imaging system, the method comprising:
  receiving a multi-well culture dish comprising a plurality of micro-wells on a stage of the imaging system, wherein the plurality of micro-wells contain a plurality of human embryos or pluripotent cells, wherein the imaging system comprises-at least one time-lapse microscope inside a housing;
  initializing the imaging system, wherein initializing the imaging system comprises:
    generating an initial image of the multi-well culture dish with the imaging system;
    detecting the presence of the multi-well culture dish on the stage of the imaging system;
  generating an estimate of a position and an orientation of the plurality of micro-wells, wherein generating the estimate of the position and the orientation of the plurality of micro-wells comprises:
    generating an initial estimate of micro-well position and orientation;
    generating a refined estimate of micro-well position and orientation; and
    determining the position and orientation of the micro-wells in a rotated coordinate system;
  providing an alignment indication, wherein the alignment indication comprises a first indication if the multi-well culture dish is properly aligned and a second indication if the multi-well culture dish is improperly aligned;
  automatically illuminating the multi-well culture dish with an illumination source of the at least one time-lapse microscope when the multi-well culture dish is properly aligned; and
  automatically focusing the at least one time-lapse microscope configured to capture time-lapse images of the multi-well culture dish when the multi-well culture dish is properly aligned;
  acquiring time-lapse images of the multi-well culture dish with a camera of the at least one time-lapse microscope; and
  analyzing the time-lapse images of the multi-well culture dish to determine a development potential of at least one human embryo or pluripotent cell.

2. The method of claim 1, wherein initializing the imaging system further comprises determining occupancy of a plurality of micro-wells in the multi-well culture dish.

3. The method of claim 1, further comprising determining parameters related to the development potential of the at least one human embryo or pluripotent cell; and displaying the images captured by the at least one time-lapse microscope in a graphical user interface accessible by a touchscreen panel.

4. The method of claim 3, wherein the parameters include a duration of first cytokinesis.

5. The method of claim 1, wherein the alignment indication comprises a visual feedback comprising a color coded LED.

6. The method of claim 1, wherein generating the initial estimate of micro-well position and orientation comprises:
  retrieving a template, wherein the template represents at least a portion of the plurality of micro-wells included in the multi-well culture dish;
  rotating the template through a series of predetermined positions;
  generating a normalized cross-correlation between the initial image and the template in each of the series of predetermined positions;
  identifying one of the series of predetermined positions of the template with the highest normalized cross-correlation score; and
  identifying the initial estimate of the micro-well position and orientation as the position and orientation of the template in the one of the series of predetermined positions of the template with the highest normalized cross-correlation score.

7. The method of claim 1, wherein generating the refined estimate of micro-well position and orientation comprises:
  selecting a first set of features from the initial image, wherein the first set of features from the initial image correspond to a set of features of the multi-well culture dish;
  generating vectors between adjacent pairs of features of the first set of features from the initial image; and
  combining the vectors to determine the orientation of the multi-well culture dish.

8. The method of claim 1, wherein providing an alignment indication comprises determining an initial alignment of the multi-well culture dish by detecting the relative position of an indexing feature of the multi-well culture dish with respect to a feature of the stage of the imaging system.

9. A method for automated imaging and evaluation of human embryos, oocytes, or pluripotent cells with an imaging system, the method comprising:
  receiving a multi-well culture dish comprising a plurality of micro-wells on a stage of the imaging system, wherein the plurality of micro-wells contain a plurality of human embryos or pluripotent cells, wherein the imaging system comprises-at least one time-lapse microscope inside a housing;
  initializing the imaging system, wherein initializing the imaging system comprises:
    generating an initial image of the multi-well culture dish with the imaging system;
    detecting the presence of the multi-well culture dish on the stage of the imaging system;
    determining occupancy of a plurality of micro-wells in the multi-well culture dish, wherein determining occupancy of a plurality of micro-wells included in the multi-well culture dish comprises:
      selecting at least one of the plurality of micro-wells;
      identifying pixels located in the selected at least one of the plurality of micro-wells;
      determining the intensity of the identified pixels;
      comparing the intensity of the identified pixels to a brightness threshold;
      determining a percent of pixels in the at least one of the plurality of micro-wells that exceed the brightness threshold; and
      identifying the at least one of the plurality of micro-wells as occupied if the percent of pixels is greater than a threshold value;

providing an alignment indication, wherein the alignment indication comprises a first indication if the multi-well culture dish is properly aligned and a second indication if the multi-well culture dish is improperly aligned;

automatically illuminating the multi-well culture dish with an illumination source of the at least one time-lapse microscope when the multi-well culture dish is properly aligned; and automatically focusing the at least one time-lapse microscope configured to capture time-lapse images of the multi-well culture dish when the multi-well culture dish is properly aligned;

acquiring time-lapse images of the multi-well culture dish with a camera of the at least one time-lapse microscope; and analyzing the time-lapse images of the multi-well culture dish to determine a development potential of at least one human embryo or pluripotent cell.

\* \* \* \* \*